(12) United States Patent
Bell et al.

(10) Patent No.: US 7,943,628 B2
(45) Date of Patent: May 17, 2011

(54) PYRIMIDINE DERIVATIVES

(75) Inventors: Andrew Simon Bell, Sandwich (GB); Charlotte Alice Louise Lane, Sandwich (GB); Charles Eric Mowbray, Sandwich (GB)

(73) Assignee: Pfizer Limited, Sandwich (GB)

( * ) Notice: Subject to any disclaimer, the term of this patent is extended or adjusted under 35 U.S.C. 154(b) by 1095 days.

(21) Appl. No.: 11/640,071

(22) Filed: Dec. 15, 2006

(65) Prior Publication Data

US 2007/0185075 A1    Aug. 9, 2007

Related U.S. Application Data

(60) Provisional application No. 60/752,612, filed on Dec. 20, 2005.

(51) Int. Cl.
*C07D 239/48* (2006.01)
*C07D 239/50* (2006.01)
*A61K 31/505* (2006.01)

(52) U.S. Cl. ...................... 514/275; 544/323
(58) Field of Classification Search ............... 544/323; 514/275
See application file for complete search history.

(56) References Cited

U.S. PATENT DOCUMENTS

2004/0002508 A1    1/2004    Nagarathnam et al. ....... 514/275

FOREIGN PATENT DOCUMENTS

| EP | 1505064 | | 2/2005 |
|---|---|---|---|
| EP | 1571146 | | 9/2005 |
| WO | WO8808424 | | 11/1988 |
| WO | WO9106542 | | 5/1991 |
| WO | WO9325539 | | 12/1993 |
| WO | WO0147921 | | 7/2001 |
| WO | WO02/072548 A2 | | 9/2002 |
| WO | WO 03/106450 | * | 12/2003 |
| WO | WO2004/022537 | | 3/2004 |
| WO | WO 2004/039796 | * | 5/2004 |
| WO | WO2004089286 | | 10/2004 |
| WO | WO2005054239 | | 6/2005 |
| WO | WO 2007/031529 | * | 3/2007 |
| WO | WO2007039467 | | 4/2007 |
| WO | WO 2007/072163 | * | 6/2007 |

OTHER PUBLICATIONS

Robinson, Medical Therapy of Inflammatory Bowel Disease for the 21$^{st}$ Century, Eur J Suppl 582, pp. 90-98, 1998.*
Singh et al., Immune Therapy in inflammatory bowel disease and models of colitis, British Journal of Surgery, 88, pp. 1558-1569, 2001.*
Esch et al., The Histamine H4 receptor as a new therapeutic target for inflammation, TRENDS in Pharmacological Sciences, vol. 26, No. 9, pp. 462-469, Sep. 2005.*
Gantner et al., Histamine H4 and H2 Receptors Control Histamine-Induced Interleukin-16 Release from Human CD8+ T Cells, The Journal of Pharmacology and Experimental Therapeutics, vol. 303, No. 1, pp. 300-307, 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, pp. 1-7, Aug. 2002.*
Simone, Oncology: Introduction, Cecil Textbook of Medicine, 20$^{th}$ Edition, vol. 1, pp. 1004-1010, 1996.*
Stark, H., *Recent Advances in Histamine $H_3/H_4$ Receptor Ligands*, Expert Opin. Ther. Patents 13(6), pp. 851-865, 2003.
Terzioglu, N.,et al., *Synthesis and Structure-Activity Relationships of Indole and Benzimidazole Piperazines as Histamine $H_4$ Receptor Antagonists*, Bioorganic & Medicinal Chemistry Letters 14, pp. 5251-5256, 2004.

* cited by examiner

*Primary Examiner* — Deepak Rao
(74) *Attorney, Agent, or Firm* — Jennifer A. Kispert; Robert T. Ronau

(57) ABSTRACT

A compound of Formula (I):

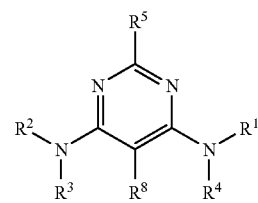

or a pharmaceutically and/or veterinarily acceptable derivative thereof, wherein $R^1$, $R^2$, $R^3$, $R^4$, $R^5$, and $R^8$ are as defined above.

11 Claims, No Drawings

PYRIMIDINE DERIVATIVES

CROSS REFERENCE TO RELATED APPLICATIONS

Priority is claimed to U.S. provisional application Ser. No. 60/752,612, filed 20 Dec. 2005, incorporated herein by reference.

BACKGROUND OF THE INVENTION

The histamine $H_4$ receptor is a 390 amino-acid, seven-transmembrane G protein coupled receptor with approximately 40% homology to the histamine $H_3$ receptor. In contrast to the $H_3$ receptor, which is primarily located in the brain, the $H_4$ receptor is expressed at greater levels in eosinophils and mast cells, among other inflammatory cells. $H_4$ receptor ligands should thus be suitable for the treatment of various inflammatory disorders. Examples of diseases where treatment with $H_4$ ligands is particularly appropriate are inflammatory bowel disease, Crohn's disease, colitis ulcerosa, dermatitis, psoriasis, conjunctivitis, rheumatoid arthritis, respiratory diseases such as adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy-induced airway responses, allergic rhinitis, viral rhinitis, non-allergic rhinitis, perennial and seasonal rhinitis, nasal congestion and allergic congestion.

Recently some histamine $H_4$ receptor ligands have been developed. An overview of the current advance in $H_4$ ligand research and patenting is given in *Expert Opin. Ther. Patents* (2003) 13(6). Examples of Histamine $H_4$ receptor ligands can be found in WO 02/072548, WO 04/022537 and in Terzioglu et al., *J. Bioorg. Med. Chem. Lett.* 14 (2004), 5251-5256.

Although $H_4$ ligands are known there is still a need to further provide new $H_4$ ligands that are good drug candidates. In particular, preferred compounds should bind potently to the histamine $H_4$ receptor whilst showing little affinity for other receptors. They should be well absorbed from the gastrointestinal tract, be metabolically stable and possess favourable pharmacokinetic properties. They should be non-toxic and demonstrate few side-effects.

SUMMARY OF THE INVENTION

The present invention thus relates to pyrimidine derivatives of formula (I):

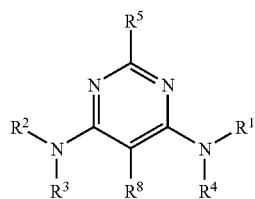

or a pharmaceutically and/or veterinarily acceptable derivative thereof, wherein:
$R^1$ is $C_{1-8}$alkyl, $C_{3-7}$cycloalkyl-$C_{0-6}$alkyl- optionally substituted with methyl, alkoxyalkyl containing 3 to 8 carbon atoms, het-$C_{0-6}$alkyl-, $CF_3$-$C_{1-6}$alkyl-, $CF_3OC_{2-3}$alkyl-, aryl-$C_{0-6}$alkyl- or $C_{1-6}$hydroxyalkyl;

$R^2$ is het, provided that the het group contains at least one nitrogen atom or is substituted by a group which contains at least one nitrogen atom; or $R^2$ is $(CH_2)_2NH_2$, $(CH_2)_2NHCH_3$, or $(CH_2)_2N(CH_3)_2$.

$R^3$ is H, $C_{1-8}$alkyl, $(CH_2)_pC_{3-7}$cycloalkyl, alkoxyalkyl containing 3 to 8 carbon atoms, $(CH_2)_nCF_3$, $(CH_2)_xOCF_3$ or $C_{1-6}$hydroxyalkyl; or $R^3$ and $R^2$ together with the nitrogen atom to which they are bound form a 4 to 8 membered non-aromatic heterocyclic group which optionally contains one or more further heteroatoms or groups independently selected from N, O, S, S(O) and S(O)$_2$, wherein the heterocyclic group is optionally a bridged bicyclic group, a spiro bicyclic group or is optionally fused to a 3-, 4-, 5- or 6-membered carbocyclic group or a 4-, 5- or 6-membered heterocyclic group which contains at least one ring member independently selected from N, O, S, S(O) and S(O)$_2$, and wherein the ring system as a whole is optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl, provided that the ring system as a whole contains at least two nitrogen atoms or contains one nitrogen atom and is substituted by a group which contains at least one nitrogen atom;

$R^4$ is H; or $R^1$ and $R^4$ together with the nitrogen atom to which they are bound form a 4 to 8 membered non-aromatic heterocyclic group which optionally contains one or more further heteroatoms or groups independently selected from N, O, S, S(O) and S(O)$_2$, wherein the heterocyclic group is optionally a bridged bicyclic group or is optionally fused to a 3-, 4-, 5- or 6- membered carbocyclic group or a 4-, 5- or 6-membered heterocyclic group which contains at least one ring member independently selected from N, O, S, S(O) and S(O)$_2$, and wherein the ring system as a whole is optionally substituted by one or more substituents independently selected from $C_{1-6}$alkyl, fluoro, $NR^9R^{10}$, $(CH_2)_eC_{3-7}$cycloalkyl, alkoxyalkyl containing 2 to 8 carbon atoms, $(CH_2)_f$het$^1$, $(CH_2)_gCF_3$, $(CH_2)_zOCF_3$, $(CH_2)_h$aryl and $C_{1-6}$hydroxyalkyl;

$R^5$ is H or $NR^{11}R^{12}$;

$R^6$ and $R^7$ are each independently selected from H, $C_{1-6}$alkyl and $(CH_2)_jC_{3-7}$cycloalkyl; or $R^6$ and $R^7$, together with the nitrogen atom to which they are bound, form a 4, 5 or 6 membered heterocyclic group;

$R^8$ is H or $C_{1-3}$alkyl;

$R^9$ and $R^{10}$ are each independently selected from H, $C_{1-6}$alkyl and $(CH_2)_kC_{3-7}$cycloalkyl; or $R^9$ and $R^{10}$, together with the nitrogen atom to which they are bound, form a 4, 5 or 6 membered heterocyclic group;

$R^{11}$ and $R^{12}$ are each independently selected from H, $C_{1-6}$alkyl and $(CH_2)_lC_{3-7}$cycloalkyl; or $R^{11}$ and $R^{12}$, together with the nitrogen atom to which they are bound, form a 4, 5 or 6 membered heterocyclic group;

$R^{13}$ and $R^{14}$ are each independently selected from H, $C_{1-6}$alkyl and $(CH_2)_mC_{3-7}$cycloalkyl; or $R^{13}$ and $R^{14}$, together with the nitrogen atom to which they are bound, form a 4, 5 or 6 membered heterocyclic group;

a, b, c, d, e, f, g, h, j, k, l, m and p are each independently selected from 0, 1, 2 and 3;

n is 1, 2 or 3;

x is 2 or 3, wherein if x is 3, then the $(CH_2)_3$ group may be replaced with a branched alkyl group containing 3 carbon atoms;

y and z are each independently selected from 1, 2 and 3 aryl is phenyl, naphthyl, anthracyl or phenanthryl, each optionally substituted by one or more groups independently selected from $C_{1-8}$alkyl, $C_{1-8}$-alkoxy, OH, halo, $CF_3$, $CHF_2$, $OCF_3$, $OCHF_2$, $SCF_3$, hydroxy-$C_{1-6}$alkyl, $C_{1-4}$alkoxy-$C_{1-6}$alkyl, $C_{1-4}$alkyl-S—$C_{1-4}$alkyl, aryl$^1$, het$^1$, Oaryl$^1$, Ohet$^1$, Saryl$^1$, Shet$^1$, $CF_2CF_3$, $CH_2CF_3$, $CF_2CH_3$, $C(O)NR^{13}R^{14}$, $C_{3-8}$cycloalkyl, $C_{3-7}$cycloalkyl-$C_{1-4}$alkyl, $C_{3-7}$cycloalkyl-$C_{1-4}$alkoxy, $C_{3-7}$cycloalkyl-O—$C_{1-4}$alkyl, $C_{3-7}$cycloalkyl-$C_{1-4}$alkoxy-$C_{1-4}$alkyl, $OC_{3-7}$cycloalkyl and $SC_{3-7}$cycloalkyl, wherein the aryl$^1$ and het$^1$ groups are optionally substituted by at least one group selected from $C_{1-6}$alkyl, $C_{3-7}$cycloalkyl, $C_{1-6}$alkoxy, $OC_{3-7}$cycloalkyl, halo, CN, OH, $CF_3$, $CHF_2$, $OCF_3$, $OCHF_2$, hydroxy$C_{1-6}$-alkyl, $C_{1-4}$alkoxy-$C_{1-4}$alkyl, $SC_{1-6}$alkyl and $SCF_3$;

het is 4 to 8 membered non-aromatic heterocyclic group which contains at least one heteroatom or group independently selected from N, O, S, S(O) and $S(O)_2$, wherein the heterocyclic group is optionally a bridged bicyclic group or is optionally fused to a 3-, 4-, 5- or 6- membered carbocyclic group or a 4-, 5- or 6-membered heterocyclic group which contains at least one ring member independently selected from N, O, S, S(O) and $S(O)_2$, and wherein the ring system as a whole is optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl;

aryl$^1$ is phenyl, naphthyl, anthracyl or phenanthryl; and het$^1$ is an aromatic or non-aromatic 4-, 5- or 6- membered heterocycle which contains at least one N, O or S heteroatom, optionally fused to a 4-, 5- or 6-membered carbocyclic group or a second 4-, 5- or 6-membered heterocycle which contains at least one N, O or S heteroatom.

Preferably aryl is phenyl.

For embodiments in which the groups "aryl", "aryl$^1$", "het" and "het$^1$" may be a substituent on more than one part of the compound, it is to be understood that each separate substituent may be the same or different to the other substituent(s) defined by the same term. For example, if $R^1$ and $R^2$ both comprise a "het" group, then the two het groups may be the same or different.

It has been found that the compounds defined above are ligands of the Histamine $H_4$ receptor.

In an embodiment of the invention $R^1$, $R^2$, $R^3$, $R^4$ and $R^5$ are as defined above, and $R^8$ is hydrogen.

In a further embodiment, $R^1$, $R^2$, $R^3$, $R^5$ and $R^8$ are as defined above, and $R^4$ is hydrogen.

In a further embodiment, $R^2$, $R^3$, $R^5$ and $R^8$ are as defined above, $R^4$ is hydrogen and $R^1$ is $C_{3-7}$cycloalkyl-$C_{0-6}$alkyl-optionally substituted with methyl.

In a further embodiment, $R^2$, $R^3$, $R^5$ and $R^8$ are as defined above, $R^4$ is hydrogen and $R^1$ is $C_{3-5}$cycloalkyl-$C_{0-1}$alkyl-optionally substituted with methyl.

In a further embodiment, $R^2$, $R^3$, $R^5$ and $R^8$ are as defined above, $R^4$ is hydrogen and $R^1$ is cyclopropyl, cyclopropylmethyl or methyl-cyclopropyl.

In a further embodiment, $R^2$, $R^3$, $R^5$ and $R^8$ are as defined above, $R^4$ is hydrogen and $R^1$ is $C_1$-$C_8$ alkyl.

In a further embodiment, $R^2$, $R^3$, $R^5$ and $R^8$ are as defined above, $R^4$ is hydrogen and $R^1$ is $C_1$-$C_6$ alkyl.

In a further embodiment, $R^2$, $R^3$, $R^5$ and $R^8$ are as defined above, $R^4$ is hydrogen and $R^1$ is ethyl, propyl, butyl, 1-methyl-propyl, 2-methyl-propyl, 2,2-dimethyl-propyl, 2-methyl-butyl, ter-butyl, 1-methyl-butyl, 3-methyl-butyl, 3,3-dimethyl-butyl, 1,2-dimethyl-propyl or isopropyl.

In a further embodiment, $R^1$, $R^4$, $R^5$ and R8 are as defined above, and $R^2$ is het, provided that the het group contains at least one nitrogen atom or is substituted by a group which contains at least one nitrogen atom and $R^3$ is H, $C_{1-8}$alkyl, $(CH_2)_pC_{3-7}$cycloalkyl, alkoxyalkyl containing 3 to 8 carbon atoms, $(CH_2)_nCF_3$, $(CH_2)_xOCF_3$ or $C_{1-6}$hydroxyalkyl; or $R^3$ and $R^2$ together with the nitrogen atom to which they are bound form a 4 to 8 membered non-aromatic heterocyclic group which optionally contains one or more further heteroatoms or groups independently selected from N, O, S, S(O) and $S(O)_2$, wherein the heterocyclic group is optionally a bridged bicyclic group, a spiro bicyclic group or is optionally fused to a 3-, 4-, 5- or 6-membered carbocyclic group or a 4-, 5- or 6-membered heterocyclic group which contains at least one ring member independently selected from N, O, S, S(O) and $S(O)_2$, and wherein the ring system as a whole is optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl, provided that the ring system as a whole contains at least two nitrogen atoms or contains one nitrogen atom and is substituted by a group which contains at least one nitrogen atom;

In a still further embodiment, $R^1$, $R^4$, $R^5$ and $R^8$ are as defined above, and $R^2$ and $R^3$, together with the nitrogen atom to which they are bound, form a 4 to 8 membered non-aromatic heterocyclic group which optionally contains one or more further heteroatoms or groups independently selected from N, O, S, S(O) and $S(O)_2$, wherein the heterocyclic group is optionally a bridged bicyclic group or is optionally fused to a 3-, 4-, 5- or 6- membered carbocyclic group or a 4-, 5- or 6-membered heterocyclic group which contains at least one ring member independently selected from N, O, S, S(O) and $S(O)_2$, and wherein the ring system as a whole is optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl, provided that the ring system as a whole contains at least two nitrogen atoms or contains one nitrogen atom and is substituted by a group which contains at least one nitrogen atom.

In a further embodiment, $R^1$, $R^4$, $R^5$ and $R^8$ are as defined above, and $R^2$ and $R^3$, together with the nitrogen atom to which they are bound, form a 4 to 8 membered non-aromatic heterocyclic group which optionally contains one or more further nitrogen atoms, wherein the heterocyclic group is optionally a bridged bicyclic group or is optionally fused to a 3-, 4-, 5- or 6- membered carbocyclic group or a 4-, 5- or 6-membered heterocyclic group which contains at least one nitrogen atom, and wherein the ring system as a whole is optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl, provided that the ring system as a whole contains at least two nitrogen atoms or contains one nitrogen atom and is substituted by a group which contains at least one nitrogen atom.

In a yet still further embodiment, $R^1$, $R^4$, $R^5$ and $R^8$ are as defined above, and $R^2$ is $(CH_2)_2NH_2$, $(CH_2)_2NHCH_3$ or$(CH_2)_2 N(CH_3)_2$ and $R^3$ is H.

In a yet still further embodiment, $R^1$, $R^4$, $R^5$ and $R^8$ are as defined above, and $R^2$ and $R^3$, together with the nitrogen atom to which they are bound, form a 4 to 8 membered non-aromatic heterocyclic group selected from the following ring systems:

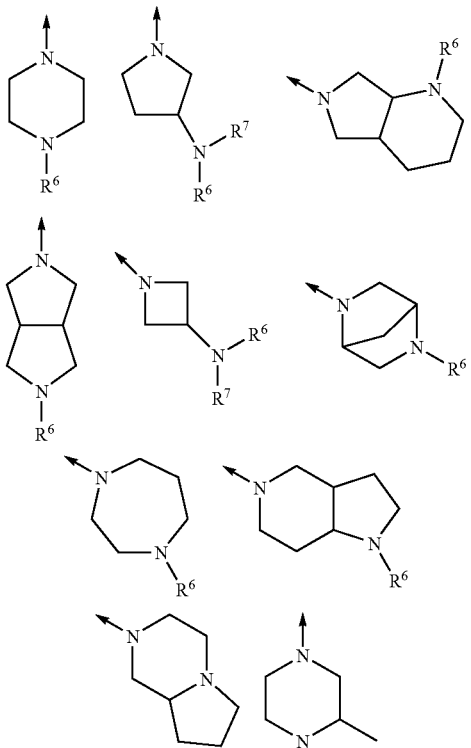

wherein the ring system as a whole may be substituted by one or more $C_{1-6}$alkyl or $(CH_2)_a C_{3-6}$cycloalkyl groups.

In a yet still further embodiment, $R^1$, $R^4$, $R^5$ and $R^8$ are as defined above, and $R^2$ and $R^3$, together with the nitrogen atom to which they are bound, form a 4 to 8 membered non-aromatic heterocyclic group selected from the following ring systems:

wherein $R^6$ and $R^7$ are independently selected from H or $CH_3$.

In a further embodiment, $R^1$, $R^4$, $R^5$ and $R^8$ are as defined above, $R^2$ is H and $R^2$ is a pyrrolidinyl group, optionally substituted by one or more substituents independently selected from $C_{1-6}$alkyl, $NR^6R^7$, $(CH_2)_a C_{3-7}$cycloalkyl, alkoxyalkyl containing 2 to 8 carbon atoms, $(CH_2)_b het^1$, $(CH_2)_c CF_3$, $(CH_2)_y OCF_3$, $(CH_2)_d aryl$ and $C_{1-6}$hydroxyalkyl.

In a further embodiment, $R^1$, $R^4$, $R^5$ and $R^8$ are as defined above, $R^3$ is H and $R^2$ is a pyrrolidinyl group optionally substituted by one or more substituents independently selected from $C_{1-6}$alkyl, $NR^6R^7$, $(CH_2)_a C_{3-7}$cycloalkyl and alkoxyalkyl containing 2 to 8 carbon atoms.

In a further embodiment, $R^1$, $R^2$, $R^3$, $R^4$ and $R^8$ are as defined above, and $R^5$ is H or $NH_2$.

DETAILED DESCRIPTION OF THE INVENTION

In the here above formula "halo" denotes a halogen atom selected from the group consisting of fluoro, chloro, bromo and iodo, in particular fluoro or chloro.

The term "alkyl" includes both straight-chain and branched chain groups. This also applies if they carry substituents such as a hydroxy substitutent or occur as substituents of other radicals, for example alkoxy groups. For example, the term $C_{1-4}$alkyl includes methyl, ethyl, n-propyl, iso-propyl, n-butyl, iso-butyl, sec-butyl and tertbutyl moieties. Examples of the corresponding alkoxy moieties are methoxy, ethoxy, n-propyloxy, iso-propyloxy, n-butyloxy, iso-butyloxy, secbutyloxy and tert-butyloxy. Furthermore, examples of suitable $C_{1-4}$alkyl moieties substituted by an hydroxyl group are hydroxymethyl, 1-hydroxyethyl, 2-hydroxyethyl, 1-hydroxypropyl, 2-hydroxypropyl, 3-hydroxypropyl, etc.

The term $C_3$-$C_7$ cycloalkyl includes bridged bicyclic cycloalkyl such as bicyclo[1.1.1]pentyl. Preferred cycloalkyl groups are cyclopropyl, cyclobutyl, cyclopentyl, cyclohexyl and bicyclo[1.1.1]pentyl.

Preferred "4 to 8 membered heterocyclic group which optionally contains one or more further heteroatoms or groups independently selected from N, O, S, S(O) and $S(O)_2$, wherein the heterocyclic group is a spiro bicyclic group" are 2,8-diaza-spiro[4.5]dec-2-yl and 2,7-diaza-spiro[4.4]non-2-yl.

The skilled person will of course appreciate that it is not possible to substitute some of the defined heterocyclic ring groups of Formula I in all positions with some of the optional substituents defined above. It is to be understood that such substitutions do not form part of the invention.

Example compounds that fall within the above definition of the invention include:

N-(3,3-Dimethylbutyl)-6-(4-methylpiperazin-1-yl)pyrimidin-4-amine,
6-[3-(Dimethylamino)pyrrolidin-1-yl]-N-(3,3-dimethylbutyl)pyrimidin-4-amine,
N-(3,3-Dimethylbutyl)-6-[(5-methylhexahydropyrrolo[3,4-c]pyrrol-2(1H)-yl]pyrimidin-4-amine,
6-[3-(Dimethylamino)azetidin-1-yl]-N-(3,3-dimethylbutyl)pyrimidin-4-amine, N-(3,3-Dimethylbutyl)-6-[5-methyl-2,5-diazabicyclo[2.2.1]hept-2-yl]pyrimidin-4-amine,
N-(3,3-Dimethylbutyl)-N'-[pyrrolidin-3-yl]pyrimidine-4,6-diamine,
N-(3,3-Dimethylbutyl)-N'-[1-methylpyrrolidin-3-yl]pyrimidine-4,6-diamine,
$N^4$-(Cyclopropylmethyl)-6-[3-(methylamino)pyrrolidin-1-yl]pyrimidine-2,4-diamine,
$N^4$-Isobutyl-6-[3-(methylamino)pyrrolidin-1-yl]pyrimidine-2,4-diamine,
$N^4$-(2,2-Dimethylpropyl)-6-[3-(methylamino)pyrrolidin-1-yl]pyrimidine-2,4-diamine,
$N^4$-Ethyl-6-[3-(methylamino)pyrrolidin-1-yl]pyrimidine-2,4-diamine,
N-Ethyl-6-[3-(methylamino)pyrrolidin-1-yl]pyrimidin-4-amine,
N-Isobutyl-6-[3-(methylamino)pyrrolidin-1-yl]pyrimidin-4-amine,
N-(Cyclopropylmethyl)-6-[3-(methylamino)pyrrolidin-1-yl]pyrimidin-4-amine,
N-(3,3-Dimethylbutyl)-6-[3-(methylamino)pyrrolidin-1-yl]pyrimidin-4-amine,
6-[3-(Dimethylamino)pyrrolidin-1-yl]-N-(3,3-dimethylbutyl)pyrimidin-4-amine,
N-(Cyclopropylrmethyl)-6-[3-(dimethylamino)pyrrolidin-1-yl]pyrimidin-4-amine,
6-[3-(Dimethylamino)pyrrolidin-1-yl]-N-isobutylpyrimidin-4-amine,
6-[3-(Dimethylamino)pyrrolidin-1-yl]-N-ethylpyrimidin-4-amine,
6-[3-(Dimethylamino)pyrrolidin-1-yl]-N-(2,2-dimethylpropyl)pyrimidin-4-amine,
$N^4$-(3,3-Dimethylbutyl)-6-[octahydro-6H-pyrrolo[3,4-b]pyridin-6-yl]pyrimidine-2,4-diamine,
$N^4$-Isopropyl-6-[octahydro-6H-pyrrolo[3,4-b]pyridin-6-yl]pyrimidine-2,4-diamine,
$N^4$-Methyl-6-[octahydro-6H-pyrrolo[3,4-b]pyridin-6-yl]pyrimidine-2,4-diamine,
$N^4$-Ethyl-6-[octahydro-6H-pyrrolo[3,4-b]pyridin-6-yl]pyrimidine-2,4-diamine,
$N^4$-Isobutyl-6-[octahydro-6H-pyrrolo[3,4-b]pyridin-6-yl]pyrimidine-2,4-diamine,
$N^4$-(Cyclopropylmethyl)-6-[octahydro-6H-pyrrolo[3,4-b]pyridin-6-yl]pyrimidine-2,4-diamine,
$N^4$-(3-Methylbutyl)-6-[octahydro-6H-pyrrolo[3,4-b]pyridin-6-yl]pyrimidine-2,4-diamine,
$N^4$-(2,2-Dimethylpropyl)-6-[octahydro-6H-pyrrolo[3,4-b]pyridin-6-yl]pyrimidine-2,4-diamine,
$N^4$-Cyclopropyl-6-[octahydro-6H-pyrrolo[3,4-b]pyridin-6-yl]pyrimidine-2,4-diamine,
$N^4$-Cyclobutyl-6-[octahydro-6H-pyrrolo[3,4-b]pyridin-6-yl]pyrimidine-2,4-diamine,
$N^4$-(Cyclopentylmethyl)-6-[octahydro-6H-pyrrolo[3,4-b]pyridin-6-yl]pyrimidine-2,4-diamine,
6-[5-Methylhexahydropyrrolo[3,4-c]pyrrol-2(1H)-yl]-$N^4$-propylpyrimidine-2,4-diamine,
$N^4$-Methyl-6-[5-methylhexahydropyrrolo[3,4-c]pyrrol-2(1H)-yl]pyrimidine-2,4-diamine,
$N^4$-Ethyl-6-[5-methylhexahydropyrrolo[3,4-c]pyrrol-2(1H)-yl]pyrimidine-2,4-diamine,
$N^4$-Isobutyl-6-[5-methylhexahydropyrrolo[3,4-c]pyrrol-2(1H)-yl]pyrimidine-2,4-diamine,
$N^4$-(Cyclopropylmethyl)-6-[5-methylhexahydropyrrolo[3,4-c]pyrrol-2(1H)-yl]pyrimidine-2,4-diamine,
$N^4$-(2,2-Dimethylpropyl)-6-[5-methylhexahydropyrrolo[3,4-c]pyrrol-2(1H)-yl]pyrimidine-2,4-diamine,
$N^4$-(3,3-Dimethylbutyl)-6-[5-methylhexahydropyrrolo[3,4-c]pyrrol-2(1H)-yl]pyrimidine-2,4-diamine,
$N^4$-(3-Methylbutyl)-6-[5-methylhexahydropyrrolo[3,4-c]pyrrol-2(1H)-yl]pyrimidine-2,4-diamine,
$N^4$-Cyclopropyl-6-[5-methylhexahydropyrrolo[3,4-c]pyrrol-2(1H)-yl]pyrimidine-2,4diamine,
$N^4$-Cyclobutyl-6-[5-methylhexahydropyrrolo[3,4-c]pyrrol-2(1H)-yl]pyrimidine-2,4-diamine,
Cyclopropylmethyl-[6-(3-methylamino-azetidin-1-yl)-pyrimidin-4-yl]-amine,
(3-Fluoro-benzyl)-[6-(3-methylamino-azetidin-1-yl)-pyrimidin-4-yl]-amine,
N-Isopropyl-6-[3-(methylamino)azetidin-1-yl]pyrimidin-4-amine,
N-(4-Fluorobenzyl)-6-[3-(methylamino)azetidin-1-yl]pyrimidin-4-amine,
N-Ethyl-6-[3-(methylamino)azetidin-1-yl]pyrimidin-4-amine,
N-Isobutyl-6-[3-(methylamino)azetidin-1-yl]pyrimidin-4-amine,
2-({6-[3-(Methylamino)azetidin-1-yl]pyrimidin-4-yl}amino)ethanol,
N-Benzyl-6-[3-(methylamino)azetidin-1-yl]pyrimidin-4-amine,
N-(2-Chlorobenzyl)-6-[3-(methylamino)azetidin-1-yl]pyrimidin-4-amine,
N-Methyl-1-[6-(4-methylpiperidin-1-yl)pyrimidin-4-yl]azetidin-3-amine,
N-(2-Methoxyethyl)-6-[3-(methylamino)azetidin-1-yl]pyrimidin-4-amine,
6-[3-(Methylamino)azetidin-1-yl]-N-(3-methylbutyl)pyrimidin-4-amine,
N-Methyl-1-(6-piperidin-1-ylpyrimidin-4-yl)azetidin-3-amine,
N-(2,2-Dimethylpropyl)-6-[3-(methylamino)azetidin-1-yl]pyrimidin-4-amine,
N-Methyl-6-[3-(methylamino)azetidin-1-yl]pyrimidin-4-amine,
N-(3,3-Dimethylbutyl)-6-[3-(methylamino)azetidin-1-yl]pyrimidin-4-amine,
$N^4$-Isopropyl-6-(3-methylamino-azetidin-1-yl)-pyrimidine-2,4-diamine,
$N^4$-(2,2-Dimethylpropyl)-6-[3-(methylamino)azetidin-1-yl]pyrimidine-2,4-diamine,
6-(3-Methylamino-azetidin-1-yl)-$N^4$-(3,3,3-trifluoro-propyl)-pyrimidine-2,4-diamine,
$N^4$-Cyclopropylmethyl-6-(3-methylamino-azetidin-1-yl)-pyrimidine-2,4-diamine,
$N^4$-(3,3-Dimethyl-butyl)-6-(3-methylamino-azetidin-1-yl)-pyrimidine-2,4-diamine,
$N^4$-(3-Fluoro-benzyl)-6-(3-methylamino-azetidin-1-yl)-pyrimidine-2,4-diamine,
$N^4$-(3-Methoxy-benzyl)-6-(3-methylamino-azetidin-1-yl)-pyrimidine-2,4-diamine,
$N^4$-Cyclobutylmethyl-6-(3-methylamino-azetidin-1-yl)-pyrimidine-2,4-diamine,
$N^4$-Cyclopentylmethyl-6-(3-methylamino-azetidin-1-yl)-pyrimidine-2,4-diamine,
$N^4$-Methyl-6-[3-(methylamino)azetidin-1-yl]pyrimidine-2,4-diamine,
$N^4$-Ethyl-6-[3-(methylamino)azetidin-1-yl]pyrimidine-2,4-diamine,
$N^4$-Isobutyl-6-[3-(methylamino)azetidin-1-yl]pyrimidine-2,4-diamine,
$N^4$-Cyclopropyl-6-[3-(methylamino)azetidin-1-yl]pyrimidine-2,4-diamine, 6-[3-(Methylamino)azetidin-1-yl]-N$^4$-propylpyrimidine-2,4-diamine,
6-[3-(Methylamino)azetidin-1-yl]-N$^4$-(3-methylbutyl)pyrimidine-2,4-diamine,
N$^4$-Cyclobutyl-6-[3-(methylamino)azetidin-1-yl]pyrimidine-2,4-diamine,
6-[3-(Methylamino)azetidin-1-yl]-N$^4$-[4-(trifluoromethoxy)benzyl]pyrimidine-2,4-diamine,
4-[({2-Amino-6-[3-(methylamino)azetidin-1-yl]pyrimidin-4-yl}amino)methyl]benzonitrile,
N$^4$-(2-Fluorobenzyl)-6-[3-(methylamino)azetidin-1-yl]pyrimidine-2,4-diamine,
N$^4$-Benzyl-6-[3-(methylamino)azetidin-1-yl]pyrimidine-2,4-diamine,
6-[3-(Methylamino)azetidin-1-yl]-N$^4$-[3-(trifluoromethyl)benzyl]pyrimidine-2,4-diamine,
N$^4$-(4-Chlorobenzyl)-6-[3-(methylamino)azetidin-1-yl]pyrimidine-2,4-diamine,
6-[3-(Methylamino)azetidin-1-yl]-N$^4$-(2-methylbenzyl)pyrimidine-2,4-diamine,
6-[3-(Methylamino)azetidin-1-yl]-N$^4$-(3-methylbenzyl)pyrimidine-2,4-diamine,
6-[3-(Methylamino)azetidin-1-yl]-N$^4$-[2-(trifluoromethyl)benzyl]pyrimidine-2,4-diamine,
6-[3-(Methylamino)azetidin-1-yl]-N$^4$-[4-(trifluoromethyl)benzyl]pyrimidine-2,4-diamine,
N$^4$-(3-Chlorobenzyl)-6-[3-(methylamino)azetidin-1-yl]pyrimidine-2,4-diamine,
N$^4$-(2-Methoxybenzyl)-6-[3-(methylamino)azetidin-1-yl]pyrimidine-2,4-diamine,
6-[3-(Methylamino)azetidin-1-yl]-N$^4$-(4-methylbenzyl)pyrimidine-2,4-diamine,
N$^4$-(2-Chlorobenzyl)-6-[3-(methylamino)azetidin-1-yl]pyrimidine-2,4-diamine,
N$^4$-(4-Fluorobenzyl)-6-[3-(methylamino)azetidin-1-yl]pyrimidine-2,4-diamine,
N$^4$-(3-Fluorobenzyl)-6-(4-methylpiperazin-1-yl)pyrimidine-2,4-diamine,
N$^4$-(3-Fluorobenzyl)-6-[5-methylhexahydropyrrolo[3,4-c]pyrrol-2(1H)-yl]pyrimidine-2,4-diamine,
N$^4$-(3,3-Dimethylbutyl)-6-[3-methylpiperazin-1-yl]pyrimidine-2,4-diamine,
N$^4$-(2,2-Dimethylpropyl)-6-[3-methylpiperazin-1-yl]pyrimidine-2,4-diamine,
N$^4$-Ethyl-6-[3-methylpiperazin-1-yl]pyrimidine-2,4-diamine,
N-(2,2-Dimethylpropyl)-6-(4-methylpiperazin-1-yl)pyrimidin-4-amine,
N-(3-Methylbutyl)-6-(4-methylpiperazin-1-yl)pyrimidin-4-amine,
N$^4$-(3,3-Dimethylbutyl)-N$^6$-[pyrrolidin-3-yl]pyrimidine-2,4,6-triamine,
N$^4$-(3,3-Dimethylbutyl)-6-(4-methylpiperazin-1-yl)pyrimidine-2,4-diamine,
N-Ethyl-6-(4-methylpiperazin-1-yl)pyrimidin-4-amine,
N-Isopropyl-6-(4-methylpiperazin-1-yl)pyrimidin-4-amine,
N-Isobutyl-6-(4-methylpiperazin-1-yl)pyrimidin-4-amine,
N-(Cyclopropylmethyl)-6-(4-methylpiperazin-1-yl)pyrimidin-4-amine,
N-(3-Methylbutyl)-N'-[pyrrolidin-3-yl]pyrimidine-4,6-diamine,
N$^4$-(3-Methylbutyl)-6-(4-methylpiperazin-1-yl)pyrimidine-2,4-diamine,
N-(2-Methoxyethyl)-6-(4-methylpiperazin-1-yl)pyrimidin-4-amine,
N-(3,3-Dimethylbutyl)-6-piperazin-1-ylpyrimidin-4-amine,
6-(4-Methylpiperazin-1-yl)-N-[tetrahydrofuran-2-ylmethyl]pyrimidin-4-amine,
4-(4-Methylpiperazin-1-yl)-6-pyrrolidin-1-ylpyrimidine,
6-(4-Methylpiperazin-1-yl)-N-(3,3,3-trifluoropropyl)pyrimidin-4-amine,
N-Isobutyl-5-methyl-6-(4-methylpiperazin-1-yl)pyrimidin-4-amine,
N-Ethyl-6-[5-methylhexahydropyrrolo[3,4-c]pyrrol-2(1H)-yl]pyrimidin-4-amine,
6-(3-Aminoazetidin-1-yl)-N-(3,3-dimethylbutyl)pyrimidin-4-amine,
N$^4$-Isopropyl-6-(4-methylpiperazin-1-yl)pyrimidine-2,4-diamine,
N$^4$-Ethyl-6-(4-methylpiperazin-1-yl)pyrimidine-2,4-diamine,
N$^4$-Isobutyl-6-(4-methylpiperazin-1-yl)pyrimidine-2,4-diamine,
N$^4$-(Cyclopropylmethyl)-6-(4-methylpiperazin-1-yl)pyrimidine-2,4-diamine,
N-(Cyclopropylmethyl)-6-[octahydro-6H-pyrrolo[3,4-b]pyridin-6-yl]pyrimidin-4-amine,
N$^4$-(3,3-Dimethylbutyl)-6-[3,4-dimethylpiperazin-1-yl]pyrimidine-2,4-diamine,
N-Isobutyl-6-[octahydro-6H-pyrrolo[3,4-b]pyridin-6-yl]pyrimidin-4-amine,
6-[6-Amino-3-azabicyclo[3.1.0]hex-3-yl]-N$^4$-(2,2-dimethylpropyl)pyrimidine-2,4-diamine,
N-(2,2-Dimethylpropyl)-6-[octahydro-6H-pyrrolo[3,4-b]pyridin-6-yl]pyrimidin-4-amine,
6-[3-(Methylamino)azetidin-1-yl]-N$^4$-(2-methylbutyl)pyrimidine-2,4-diamine,
N$^4$-[(1S)-1,2-Dimethylpropyl]-6-[3-(methylamino)azetidin-1-yl]pyrimidine-2,4-diamine,
N$^4$-(2,5-Difluorobenzyl)-6-[3-(methylamino)azetidin-1-yl]pyrimidine-2,4-diamine,
N$^4$-(2,3-Difluorobenzyl)-6-[3-(methylamino)azetidin-1-yl]pyrimidine-2,4-diamine,
N$^4$-Butyl-6-[3-(methylamino)azetidin-1-yl]pyrimidine-2,4-diamine,
6-(1,4-Diazepan-1-yl)-N$^4$-isobutylpyrimidine-2,4-diamine,
6-[(3R)-3-(Methylamino)pyrrolidin-1-yl]-N$^4$-(2-methylcyclopropyl)pyrimidine-2,4-diamine,
N$^4$-Isobutyl-6-(4-methyl-1,4-diazepan-1-yl)pyrimidine-2,4-diamine,
N$^4$-(Cyclopropylmethyl)-6-(3-pyrrolidin-1-ylazetidin-1-yl)pyrimidine-2,4-diamine,
N$^4$-Isopropyl-6-[(3aR*,7aS*)-octahydro-5H-pyrrolo[3,2-c]pyridin-5-yl]pyrimidine-2,4-diamine,
N$^4$-Bicyclo[1.1.1]pent-1-yl-6-[(3R)-3-(methylamino)pyrrolidin-1-yl]pyrimidine-2,4-diamine,
6-(4-Aminopiperidin-1-yl)-N$^4$-ethylpyrimidine-2,4-diamine,
6-[3-Methyl-3-(methylamino)azetidin-1-yl]-N$^4$-propylpyrimidine-2,4-diamine,
N$^4$-(2,2-Dimethylpropyl)-6-(hexahydropyrrolo[1,2-a]pyrazin-2(1H)-yl)pyrimidine-2,4-diamine,
N$^4$-(2,2-Dimethylpropyl)-6-(3-pyrrolidin-1-ylazetidin-1-yl)pyrimidine-2,4-diamine,
N$^4$-(2,2-Dimethylpropyl )-N$^6$-[2-(methylamino)ethyl]pyrimidine-2,4,6-triamine,
N$^4$-[2-(Dimethylamino)ethyl]-N$^6$-(2,2-dimethylpropyl)pyrimidine-2,4,6-triamine,
N$^4$-(2,2-Dimethylpropyl)-6-[3-(isopropylamino)azetidin-1-yl]pyrimidine-2,4-diamine,
6-[(3R)-3-(Methylamino)pyrrolidin-1-yl]-N-[(1R)-1-methylpropyl]pyrimidin-4-amine, N-Butyl-6-[(3R)-3-(methylamino)pyrrolidin-1-yl]pyrimidin-4-amine,
$N^4$-(tert-Butyl)-6-[(3R)-3-(methylamino)pyrrolidin-1-yl]pyrimidine-2,4-diamine,
6-[(3R)-3-(Methylamino)pyrrolidin-1-yl]-$N^4$-(1-methylcyclopropyl)pyrimidine-2,4-diamine,
$N^4$-(tert-Butyl)-6-[(4aS*,7aS*)-octahydro-6H-pyrrolo[3,4-b]pyridin-6-yl]pyrimidine-2,4-diamine,
6-[(3R)-3-(Methylamino)pyrrolidin-1-yl]-$N^4$-[(1S)-1-methylpropyl]pyrimidine-2,4-diamine,
6-[(3R)-3-(Methylamino)pyrrolidin-1-yl]-$N^4$-[(1R)-1-methylpropyl]pyrimidine-2,4-diamine, and,
N-(sec-Butyl)-6-[3-(methylamino)azetidin-1-yl]pyrimidin-4-amine, or a pharmaceutically and/or veterinarily acceptable derivative thereof.

An embodiment of the invention provides the following compounds:
$N^4$-(Cyclopropylmethyl)-6-[(3R)-3-(methylamino)pyrrolidin-1-yl]pyrimidine-2,4-diamine,
$N^4$-(Cyclopropylmethyl)-6-[(3R)-3-(methylamino)pyrrolidin-1-yl]pyrimidine-2,4-diamine tartrate,
$N^4$-Isobutyl-6-[(3R)-3-(methylamino)pyrrolidin-1-yl]pyrimidine-2,4-diamine,
$N^4$-(2,2-Dimethylpropyl)-6-[(3R)-3-(methylamino)pyrrolidin-1-yl]pyrimidine-2,4-diamine, N-Isobutyl-6-[(3R)-3-(methylamino)pyrrolidin-1-yl]pyrimidin-4-amine,
N-(Cyclopropylmethyl)-6-[(3R)-3-(methylamino)pyrrolidin-1-yl]pyrimidin-4-amine,
$N^4$-(2,2-Dimethylpropyl)-6-[(4aR*,7aR*)-octahydro-6H-pyrrolo[3,4-b]pyridin-6-yl]pyrimidine-2,4-diamine,
$N^4$-Cyclopropyl-6-[(4aR*,7aR*)-octahydro-6H-pyrrolo[3,4-b]pyridin-6-yl]pyrimidine-2,4-diamine,
$N^4$-Cyclobutyl-6-[(4aR*,7aR*)-octahydro-6H-pyrrolo[3,4-b]pyridin-6-yl]pyrimidine-2,4-diamine,
$N^4$-(2,2-Dimethylpropyl)-6-[3-(methylamino)azetidin-1-yl]pyrimidine-2,4-diamine,
6-(3-Methylamino-azetidin-1-yl)-$N^4$-(3,3,3-trifluoro-propyl)-pyrimidine-2,4-diamine,
$N^4$-Cyclopropylmethyl-6-(3-methylamino-azetidin-1-yl)-pyrimidine-2,4-diamine,
$N^4$-(3,3-Dimethyl-butyl)-6-(3-methylamino-azetidin-1-yl)-pyrimidine-2,4-diamine,
$N^4$-(3-Fluoro-benzyl)-6-(3-methylamino-azetidin-1-yl)-pyrimidine-2,4-diamine,
$N^4$-Cyclopentylmethyl-6-(3-methylamino-azetidin-1-yl)-pyrimidine-2,4-diamine,
$N^4$-Isobutyl-6-[3-(methylamino)azetidin-1-yl]pyrimidine-2,4-diamine,
6-[3-(Methylamino)azetidin-1-yl]-$N^4$-propylpyrimidine-2,4-diamine,
$N^4$-(2-Methoxybenzyl)-6-[3-(methylamino)azetidin-1-yl]pyrimidine-2,4-diamine,
$N^4$-(2,2-Dimethylpropyl)-6-[(3R)-3-methylpiperazin-1-yl]pyrimidine-2,4-diamine,
$N^4$-Ethyl-6-(4-methylpiperazin-1-yl)pyrimidine-2,4-diamine,
$N^4$-(Cyclopropylmethyl)-6-(4-methylpiperazin-1-yl)pyrimidine-2,4-diamine,
6-[3-(Methylamino)azetidin-1-yl]-$N^4$-(2-methylbutyl)pyrimidine-2,4-diamine,
$N^4$-(2,5-Difluorobenzyl)-6-[3-(methylamino)azetidin-1-yl]pyrimidine-2,4-diamine,
$N^4$-(2,3-Difluorobenzyl)-6-[3-(methylamino)azetidin-1-yl]pyrimidine-2,4-diamine,
$N^4$-Butyl-6-[3-(methylamino)azetidin-1-yl]pyrimidine-2,4-diamine,
6-[(3R)-3-(Methylamino)pyrrolidin-1-yl]-$N^4$-(2-methylcyclopropyl)pyrimidine-2,4-diamine,
$N^4$-Isobutyl-6-(4-methyl-1,4-diazepan-1-yl)pyrimidine-2,4-diamine,
$N^4$-(Cyclopropylmethyl)-6-(3-pyrrolidin-1-ylazetidin-1-yl)pyrimidine-2,4-diamine,
$N^4$-Bicyclo[1.1.1]pent-1-yl-6-[(3R)-3-(methylamino)pyrrolidin-1-yl]pyrimidine-2,4-dimine,
6-[3-Methyl-3-(methylamino)azetidin-1-yl]-$N^4$-propylpyrimidine-2,4-diamine,
$N^4$-(2,2-Dimethylpropyl)-6-(hexahydropyrrolo[1,2-a]pyrazin-2(1H)-yl)pyrimidine-2,4-diamine,
$N^4$-(2,2-Dimethylpropyl)-6-(3-pyrrolidin-1-ylazetidin-1-yl)pyrimidine-2,4-diamine,
$N^4$-(2,2-Dimethylpropyl)-6-[3-(isopropylamino)azetidin-1-yl]pyrimidine-2,4-diamine,
$N^4$-(tert-Butyl)-6-[(3R)-3-(methylamino)pyrrolidin-1-yl]pyrimidine-2,4-diamine,
6-[(3R)-3-(Methylamino)pyrrolidin-1-yl]-$N^4$-(1-methylcyclopropyl)pyrimidine-2,4-diamine,
$N^4$(tert-Butyl)-6-[(4aS*,7aS*)-octahydro-6H-pyrrolo[3,4-b]pyridin-6-yl]pyrimidine-2,4-diamine,
$N^4$-(2,2-Dimethylpropyl)-6-piperazin-1-ylpyrimidine-2,4-diamine,
$N^4$-(2,2-Dimethylpropyl)-6-[3-(methylamino)azetidin-1-yl]pyrimidine-2,4-diamine hydrochloride,
$N^4$-(2,2-Dimethylpropyl)-6-[(3aR*,7aS*)-octahydro-5H-pyrrolo[3,2-c]pyridin-5-yl]pyrimidine-2,4-diamine,
6-Piperazin-1-yl-$N^4$-propylpyrimidine-2,4-diamine,
$N^4$-(Cyclopropylmethyl)-6-[(4aR,7aR)-octahydro-6H-pyrrolo[3,4-b]pyridin-6-yl]pyrimidine-2,4-diamine,
$N^4$-(2,2-Dimethylpropyl)-6-[(4aS,7aS)-octahydro-6H-pyrrolo[3,4-b]pyridin-6-yl]pyrimidine-2,4-diamine,
$N^4$-(Cyclopropylmethyl)-6-[(3R)-3-(methylamino)pyrrolidin-1-yl]pyrimidine-2,4-diamine,
$N^4$-Isopropyl-6-[(4aS,7aS)-octahydro-6H-pyrrolo[3,4-b]pyridin-6-yl]pyrimidine-2,4-diamine,
4-[3-(Methylamino)azetidin-1-yl]-6-(4-methylpiperidin-1-yl)pyrimidin-2-amine,
$N^4$-(Cyclopentylmethyl)-6-[(3R)-3-(methylamino)pyrrolidin-1-yl]pyrimidine-2,4-diamine,
$N^4$-Cyclobutyl-6-[(4aS,7aS)-octahydro-6H-pyrrolo[3,4-b]pyridin-6-yl]pyrimidine-2,4-diamine,
6-[(3R)-3-(Methylamino)pyrrolidin-1-yl]-$N^4$-propylpyrimidine-2,4-diamine, and,
$N^4$-Ethyl-6-(4-methyl-1,4-diazepan-1-yl)pyrimidine-2,4-diamine, or a pharmaceutically and/or veterinarily acceptable derivative thereof.

A further embodiment of the invention provides the following compounds:
$N^4$-(Cyclopropylmethyl)-6-[(3R)-3-(methylamino)pyrrolidin-1-yl]pyrimidine-2,4-diamine,
$N^4$-(Cyclopropylmethyl)-6-[(3R)-3-(methylamino)pyrrolidin-1-yl]pyrimidine-2,4-diamine tartrate
$N^4$-(2,2-Dimethylpropyl)-6-[3-(methylamino)azetidin-1-yl]pyrimidine-2,4-diamine, and,
$N^4$-(2,2-Dimethylpropyl)-6-[3-(methylamino)azetidin-1-yl]pyrimidine-2,4-diamine hydrochloride, or a pharmaceutically and/or veterinarily acceptable derivative thereof.

By pharmaceutically and/or veterinarily acceptable derivative it is meant any pharmaceutically or veterinarily acceptable salt, solvate, ester or amide, or salt or solvate of such ester or amide, of the compounds of formula (I) or any other compound which upon administration to the recipient is capable of providing (directly or indirectly) a compound of formula (I) or an active metabolite or residue thereof. Preferably, pharmaceutically and/or veterinarily acceptable derivative means any pharmaceutically or veterinarily acceptable salt or solvate of the compounds of formula (I)

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties. Selection, and Use* by Stahl and Wermuth (Wiley-VCH, Weinheim, Germany, 2002).

Pharmaceutically acceptable salts of the compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

Hereinafter all references to compounds of formula (I) include derivatives thereof and complexes of the compound or derivatives thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Desicn*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include:
(i) where the compound of formula (I) contains a carboxylic acid functionality (—COOH), an ester thereof, for example, a compound wherein the hydrogen of the carboxylic acid functionality of the compound of formula (I) is replaced by $(C_1-C_8)$alkyl;
(ii) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and
(iii) where the compound of formula (I) contains a primary or secondary amino functionality (—NH$_2$ or —NHR where R is not H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include:
(i) where the compound of formula (I) contains a methyl group, an hydroxymethyl derivative thereof (—CH$_3$→—CH$_2$OH):
(ii) where the compound of formula (I) contains an alkoxy group, an hydroxy derivative thereof (—OR→—OH);
(iii) where the compound of formula (I) contains a tertiary amino group, a secondary amino derivative thereof (—NR$^a$R$^b$→—NHR$^a$ or —NHR$^b$);
(iv) where the compound of formula (I) contains a secondary amino group, a primary derivative thereof (—NHR$^a$→—NH$_2$);
(v) where the compound of formula (I) contains a phenyl moiety, a phenol derivative thereof (—Ph→—PhOH); and
(vi) where the compound of formula (I) contains an amide group, a carboxylic acid derivative thereof (—CONR$^c$R$^d$→COOH).

Compounds of formula (I) containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate, l-tartrate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically labelled compounds of formula (I) can generally be prepared by conventional techniques known to those skilled in the art or by processes analogous to those described in the accompanying Examples and Preparations using an appropriate isotopically labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of formula (I) may be prepared according to scheme 1 that follows.

Scheme 1

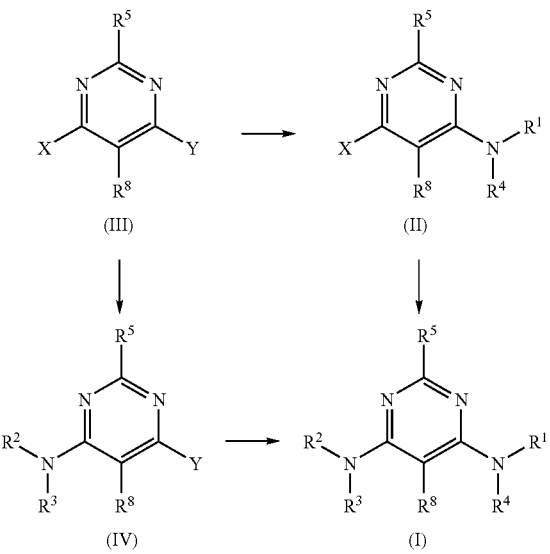

wherein $R^1$, $R^2$, $R^3$, $R^4$, $R^5$ and $R^8$ are as defined above, and X and Y are leaving groups.

According to scheme 1, compounds of formula (I) may be prepared by the reaction of a compound of formula (II) with a suitable amine. Conveniently reaction is effected by using an excess of the amine or stoichiometric quantity of the amine in the presence of a base such as a tertiary amine base (e.g. triethylamine or N-ethyl-N-isopropylpropan-2-amine); optionally in the presence of a suitable solvent (e.g. dimethyl sulphoxide or 1-methylpyrrolidin-2-one); optionally in the presence of a catalyst (such as caesium fluoride); and at elevated temperature, such as 120° C. to 150° C.

Compounds of formula (II) may be prepared by reaction of a compound of formula (III) with a suitable amine. Conveniently reaction is effected by using an excess of the amine or stoichiometric quantity of the amine in the presence of a base such as a tertiary amine base (e.g. triethylamine or N-ethyl-N-isopropylpropan-2-amine); in the presence of a suitable solvent (e.g. ethanol, 2-propanol or 1-methylpyrrolidin-2-one); and at ambient or elevated temperature, such as ambient temperature to 85° C.

According to scheme 1, the groups X and Y represent a halogen atom (e.g. chlorine) or an alternative leaving group such as a sulphonate ester (e.g. 4-methylphenyl sulphonate) or a sulphonyl group (e.g. methane sulphonyl or phenyl sulphonyl) or a sulphinyl group (e.g. methane sulphinyl).

It will be appreciated by those skilled in the art that the transformations described may be carried out in a manner that does not require the isolation or purification of the intermediate compound of formula (II) but that requires sequential addition of suitable amines, with or without additional base (e.g. triethylamine or N-ethyl-N-isopropylpropan-2-amine) or solvent, to a compound or formula (III) in the presence of a suitable solvent (e.g. 1-methylpyrrolidin-2-one or dimethyl sulphoxide) with or without heating the reaction mixture between the addition of the two amines, and with or without the addition of a catalyst (such as caesium fluoride).

It will be further appreciated by those skilled in the art that it may be necessary or desirable to carry out the transformations described in the schemes in a different order from that described, or to modify one or more of the transformations, to provide the desired compound of formula (I).

It will be appreciated by those skilled in the art that, as illustrated in the schemes above, it may be necessary or desirable at any stage in the synthesis of compounds of formula (I) to protect one or more sensitive groups in the molecule so as to prevent undesirable side reactions. In particular, it may be necessary or desirable to protect amino groups. The protecting groups used in the preparation of compounds of formula (I) may be used in conventional manner. See, for example, those described in 'Protective Groups in Organic Synthesis' by Theodora W Green and Peter G M Wuts, third edition, (John Wiley and Sons, 1999), in particular chapter 7, pages 494-653 ("Protection for the Amino Group"), incorporated herein by reference, which also describes methods for the removal of such groups.

Compounds of formula (III) are known in the literature or easily prepared by methods well known to those skilled in the art.

The compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semisolid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropyl-methylcellulose), blisters and cartridges for use in an inhaler or insufflator may be formulated to contain a powder mix of the compound of the invention, a suitable powder base such as lactose or starch and a performance modifier such as/-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount or the drug product is packaged as discrete single dose units for use in the inhaler device. Units in accordance with the invention are typically arranged to administer a metered dose or "puff" containing from 1 µg to 4000 µg of the compound of formula (I). The overall daily dose will typically be in the range 1 µg to 20 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 2000 mg depending, of course, on the mode of administration. For example, oral administration may require a total daily dose of from 0.1 mg to 2000 mg, while an intravenous dose may only require from 0.01 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the invention can also be used as a combination with one or more additional therapeutic agents to be co-administered to a patient to obtain some particularly desired therapeutic end result. The second and more additional therapeutic agents may also be a compound of the formula (I) or a pharmaceutically and/or veterinarily acceptable derivative thereof, or one or more histamine $H_4$ receptor ligands known in the art. More typically, the second and more therapeutic agents will be selected from a different class of therapeutic agents.

As used herein, the terms "co-administration", "co-administered" and "in combination with", referring to the compounds of the invention and one or more other therapeutic agents, is intended to mean, and does refer to and include the following:

simultaneous administration of such combination of compound(s) of formula (I) and therapeutic agent(s) to a patient in need of treatment, when such components are formulated together into a single dosage form which releases said components at substantially the same time to said patient, substantially simultaneous administration of such combination of compound(s) of formula (I) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (I) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of the invention or compositions thereof, include, but are by no means limited to:

Histamine $H_1$ receptor antagonists, in particular loratidine, desloratidine, fexofenadine and cetirizine Histamine $H_3$ receptor antagonists Histamine $H_2$ receptor antagonists Leukotriene antagonists, including antagonists of $LTB_4$, $LTC_4$, $LTD_4$, and $LTE_4$; for example Montelukast Phosphodiesterase inhibitors, including PDE3 inhibitors, PDE4 inhibitors, PDE5 inhibitors, PDE7 inhibitors and inhibitors of two or more phosphodiesterases, such as dual PDE3/PDE4 inhibitors neurotransmitter re-uptake inhibitors, in particular fluoxetine, sertraline, paroxetine, ziprasidone 5-Lipoxygenase (5-LO) inhibitors or 5-lipoxygenase activating protein (FLAP) antagonists $\alpha_1$- and $\alpha_2$-adrenoceptor agonist vasoconstrictor sympathomimetic agents for decongestant use Muscarinic M3 receptor antagonists or anticholinergic agents $\beta_2$-adrenoceptor agonists Dual acting $\beta_2$/M3 agents Xanthines, such as theophylline and aminophylline Non-steroidal anti-inflammatories, such as sodium cromoglycate and nedocromil sodium Ketotifen COX-1 inhibitors (NSAIDs) and COX-2 selective inhibitors Oral or inhaled Glucocorticosteroids Monoclonal antibodies active against endogenous inflammatory entities Anti-tumor necrosis factor (anti-TNF-$\alpha$) agents Adhesion molecule inhibitors including VLA-4 antagonists Kinin-$B_1$- and $B_2$-receptor antagonists Immunosuppressive agents Inhibitors of matrix metalloproteases (MMPs)

Tachykinin $NK_1$, $NK_2$ and $NK_3$ receptor antagonists

Elastase inhibitors

Adenosine A2a receptor agonists

Inhibitors of urokinase

Compounds that act on dopamine receptors, e.g. D2 agonists

Modulators of the NF$\kappa$b pathway, e.g. IKK inhibitors

Agents that can be classed as mucolytics or anti-tussive

Antibiotics

Modulators of cytokine signaling pathways, such as p38 MAP kinase inhibitors, syk tyrosine kinase inhibitors or JAK kinase inhibitors Modulators of the prostaglandin pathways, including inhibitors of H-PDGS and antagonists of DP-1 and CRTH2

Antagonists of chemokine receptors CXCR1 and CXCR2

Antagonists of chemokine receptors CCR3, CCR4 and CCR5

Inhibitors of cytosolic and soluble phospholipase $A_2$ ($cPLA_2$ and $sPLA_2$)

Prostaglandin D2 receptor antagonists (DP1 and CRTH2)

Inhibitors of Prostaglandin D synthase (PGDS)

Inhibitors of phosphoinositide-3-kinase,

HDAC inhibitors, p38 inhibitors and/or

CXCR2 antagonists.

According to the present invention, combination of the compounds of formula (I) with:

Histamine $H_1$ receptor antagonists, in particular loratidine, desloratidine, fexofenadine and cetirizine, Histamine $H_3$ receptor antagonists, Histamine $H_2$ receptor antagonists, Leukotriene antagonists, including antagonists of $LTB_4$, $LTC_4$, $LTD_4$, and $LTE_4$, for example Montelukast, and/or, Phosphodiesterase PDE4 inhibitors form a further embodiment of the invention.

The compounds of formula (I) have the ability to interact with the $H_4$ receptor and thereby have a wide range of therapeutic applications, as described further below, because of the essential role, which the $H_4$ receptor plays in the physiology of all mammals. According to this invention $H_4$ ligands are meant to include $H_4$ receptor antagonists, agonists and inverse agonists. For the preferred indications to be treated according to the invention, $H_4$ antagonists are believed to be most suitable.

Therefore, a further aspect of the present invention relates to the compounds of formula (I) or pharmaceutically acceptable salts, derived forms or compositions thereof, for use as medicaments, more particularly in the treatment of diseases, disorders, and conditions in which the $H_4$ receptor is involved. More specifically, the present invention also concerns the compounds of the invention for use in the treatment of diseases, disorders, and conditions selected from the group consisting of:

inflammatory diseases;

respiratory diseases (e.g. adult respiratory distress syndrome, acute respiratory distress syndrome, bronchitis, chronic bronchitis, chronic obstructive pulmonary disease, cystic fibrosis, asthma, emphysema, rhinitis, chronic sinusitis), allergy, allergy-induced airway responses, allergic rhinitis, viral rhinitis, non-allergic rhinitis, perennial and seasonal rhinitis, nasal congestion, allergic congestion;

female and male sexual dysfunction;

skin diseases such as dermatitis and psoriasis;

cardiac dysfunctions such as myocardial ischaemia and arrythmia;

diseases of the gastrointestinal tract such as inflammatory bowel disease, Crohn's disease and colitis ulcerosa;

cancer;

rheumatoid arthritis;

hypotension;

inflammatory pain and overactive bladder conditions.

The compounds of formula (I) according to the present invention are particularly suitable for the treatment of asthma, allergy, allergy-induced airway responses, allergic rhinitis, viral rhinitis, non-allergic rhinitis, perennial and seasonal rhinitis, nasal congestion and allergic congestion.

A still further aspect of the present invention also relates to the use of the compounds of the invention for the manufacture of a drug being a $H_4$ ligand. In particular, the present inventions concerns the use of the compounds of formula (I), or pharmaceutically and/or veterinarily acceptable derivatives thereof, for the manufacture of a drug for the treatment of $H_4$ mediated diseases and/or conditions, in particular the diseases and/or conditions listed above.

As a consequence, the present invention provides a particularly interesting method to treat a mammal, including a human being, with an effective amount of a compound of formula (I), or a pharmaceutically and/or veterinarily acceptable derivative thereof. More precisely, the present invention provides a particularly interesting method for the treatment of a $H_4$ mediated diseases and/or conditions in a mammal, including a human being, in particular the diseases and/or conditions listed above, comprising administering to said mammal an effective amount of a compound of the invention.

The compounds of the invention may have the advantage that they are more potent, have a longer duration of action, have a broader range of activity, are more stable, are easier and/or safer to prepare, have fewer side effects or are more selective, or have other more useful properties than the compounds of the prior art.

The following examples illustrate the preparation of compounds of formula (I) according to the present invention $^1$H Nuclear magnetic resonance (NMR) spectra were in all cases consistent with the proposed structures. Characteristic chemical shifts (δ) are given in parts-per-million (ppm) downfield from tetramethylsilane using conventional abbreviations for designation of major peaks: e.g. s (singlet), d (doublet), t (triplet), q (quartet) m (multiplet) and br (broad). The mass spectra (m/z) were recorded using either electrospray ionisation (ESI) or atmospheric pressure chemical ionisation (APCI). Purfication by SCX indicates use of strong cation exchange resin.

In the examples section, the following abbreviations are used:

| | |
|---|---|
| DCM | dichloromethane |
| DIPEA | N-ethyl-N-isopropylpropan-2-amine |
| DMSO | dimethyl sulphoxide |
| IPA | 2-propanol |
| NMP | 1-methylpyrrolidin-2-one |
| SCX | strong cation exchange |
| TEA | triethylamine |
| THF | tetrahydrofuran |
| TLC | thin-layer chromatography |

EXAMPLES

Preparation 1: tert-Butyl [1-(6-chloro-pyrimidin-4-yl)-azetidin-3-yl]-methyl-carbamate

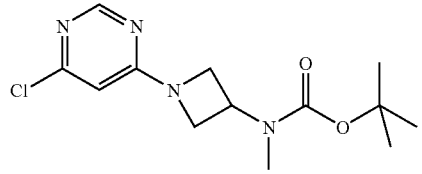

Azetidin-3-yl-methyl-carbamic acid tert-butyl ester (1.97 g, 11 mmol) in IPA (5 mL) was added dropwise to a stirred solution of 4,6-dichloropyrimidine (1.49 g, 10 mmol) in IPA (20 mL) followed by dropwise addition of TEA (2.11 mL, 15.1 mmol) at ambient temperature under $N_2$. The resulting milky yellow solution was heated to 80° C. and maintained at 80° C. for 2 hours. The solution was allowed to cool and evaporated to give a yellow oil. The crude material was partitioned between DCM (70 mL) and water (30 aqueous extract was re-extracted with DCM (70 mL). The combined organic extract was washed with saturated aqueous sodium bicarbonate (30 mL), dried ($MgSO_4$), filtered and evaporated to give a coloured oil. The crude oil was purified by flash column chromatography on silica gel eluting with DCM: MeOH (99:1 changing to 96:4 by volume) to yield the title compound as a solid (1.93 g, 64%).

$^1$H NMR (400 MHz, $CD_3OD$): δ 8.25 (1H, d), 6.47 (1H, s), 4.9 (1H, br s), 4.31 (2H, t), 4.21 (2H, m), 2.94 (3H, s), 1.45 (9H, s) ppm.

MS (ESI) m/z 299 [M+H]$^+$

Preparations 2 to 11

The following compounds of the general formula shown below were prepared by a method similar to that described for preparation 1 using the appropriate starting material and 4,6-dichloropyrimidine. The reactions were monitored by TLC analysis and were heated to reflux for 3 to 18 hours.

| No. | NRR' | Name | Yield | LRMS m/z |
|---|---|---|---|---|
| 2 | 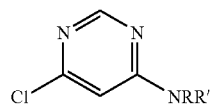 | (3R)-1-(6-Chloropyrimidin-4-yl)-N,N-dimethylpyrrolidin-3-amine | 66% | 227 |

-continued

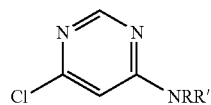

| No. | NRR' | Name | Yield | LRMS m/z |
|---|---|---|---|---|
| 3 | | (3S)-1-(6-Chloropyrimidin-4-yl)-N,N-dimethylpyrrolidin-3-amine | 81% | 227 |
| 4 | | (3aR*,6aS*)-2-(6-Chloropyrimidin-4-yl)-5-methyloctahydropyrrolo[3,4-c]pyrrole | 77% | 239 |
| 5 | | 1-(6-Chloropyrimidin-4-yl)-N,N-dimethylazetidin-3-amine | 55% | 213 |
| 6 | | 4-Chloro-6-(4-methylpiperazin-1-yl)pyrimidine | 77% | 213 |
| 7 | | (1S,4S)-2-(6-Chloropyrimidin-4-yl)-5-methyl-2,5-diazabicyclo[2.2.1]heptane | 97% | 225 |
| 8 | | N-[(3R)-1-Benzylpyrrolidin-3-yl]-6-chloropyrimidin-4-amine | 64% | 289 |
| 9 | | N-[(3S)-1-Benzylpyrrolidin-3-yl]-6-chloropyrimidin-4-amine | 49% | 289 |
| 10 | | tert-Butyl [(3R)-1-(6-chloropyrimidin-4-yl)pyrrolidin-3-yl]methylcarbamate | 86% | 313 |
| 11 | | tert-Butyl [(3S)-1-(6-chloropyrimidin-4-yl)pyrrolidin-3-yl]methylcarbamate | 95% | 313 |

Preparation 12: tert-Butyl [1-(2-amino-6-chloro-pyrimidin-4-yl)-azetidin-3-yl]-methyl-carbamate

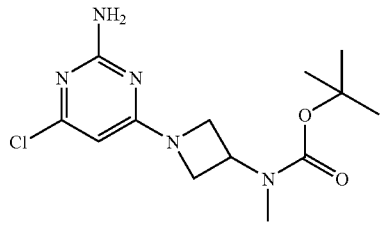

2-Amino-4,6-dichloropyrimidine (26.2 g, 160 mmol) was added portionwise to a stirred solution of azetidin-3-methyl-carbamic acid tert-butyl ester HCl salt (37.4 g, 168 mmol) in absolute EtOH (400 mL) followed by TEA (55.6 mL, 400 mmol) dropwise at ambient temperature. The resulting suspension was warmed to reflux (initially a clear solution was observed on warming) which resulted in the gradual formation of a precipitate. The mixture was refluxed for a total of 2 hours. The mixture was allowed to cool and diluted with water (200 mL) dropwise over 30 min and stirring continued for 45 min. The resulting solid was filtered, washed with water (150 mL) and dried under suction to yield the title compound as a white solid (42.74 g, 85%).

hu 1H NMR (400 MHz, $CDCl_3$): δ 5.66 (1H, s), 5.02 (1H, br s), 4.86 (2H, br s), 4.20 (2H, t), 4.04 (2H, m), 2.91 (3H, s), 1.47 (9H, s) ppm.

MS (APCI) m/z 314 $[M+H]^+$

Preparation 13: 4-Chloro-6-[(3aR,6aS)-5-methyl-hexahydropyrrolo[3,4-c]pyrrol-2(1H)-yl]pyrimidin-2-amine

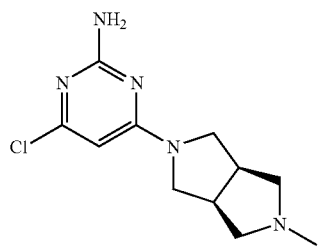

2-Amino-4,6-dichloropyrimidine (1.64 g, 10 mmol) was added portionwise to a stirred solution (3aR,6aS)-2-methyl-loctahydropyrrolo[3,4-c]pyrrole (1.6 g, 12.5 mmol) in absolute EtOH (10 mL) followed by TEA (1.8 mL, 12.5 mmol) dropwise at ambient temperature. The resulting suspension was warmed to reflux (initially a clear solution was observed on warming) and resulted in the gradual formation of a tan coloured precipitate. The mixture was refluxed for a total of 3 hours. The mixture was allowed to cool, EtOH (30 mL) was added to the mixture and heated to give a solution and was left to cool to ambient temperature. The resulting solid was collected by filtration, washed with cold EtOH (50 mL) and dried under suction to yield the title compound as a solid (2.07 g, 82%).

1H NMR (400 MHz, $CD_3OD$): δ 5.88 (1H, s), 3.62 (2H, m), 3.41 (2H, m), 3.0 (2H, m), 2.47 (2H, dd), 2.33 (3H, s) ppm.

MS (APCI) m/z 254, 256 $[M+H]^+$

Preparation 14: tert-Butyl (4aR*,7aR*)-6-(2-amino-6-chloropyrimidin-4-yl)octahydro-1H-pyrrolo[3,4-b]pyridine-1-carboxylate

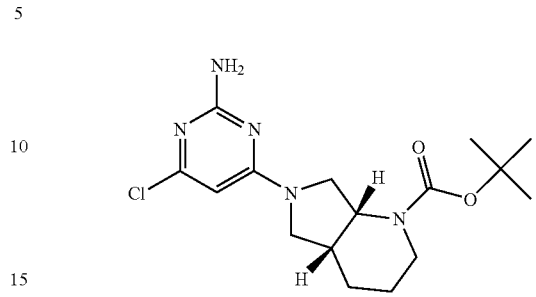

To a solution of racemic tert-butyl (4aR*,7aR*)-octahydro-1H-pyrrolo[3,4-b]pyridine-1-carboxylate (460 mg, 2.03 mmol) in EtOH (1 mL) containing DIPEA (590 µL, 3.39 mmol) was added a solution of 2-amino-4,6-dichloropyrimidine (277 mg, 169 mmol) in EtOH (9 mL) with stirring and the solution was heated to reflux for 24 hours. The solution was cooled and diluted with water (10 mL) and the resulting solid was collected by filtration, washed with water (20 mL) and dried in vacuo at 60° C. to yield the title compound as a white solid (558 mg, 93%).

1H NMR (400 MHz, $CD_3OD$): δ 5.85 (1H, s), 4.7 (1H, m), 3.98 (1H, m), 3.8-3.55 (1H, m), 3.45-3.15 (1H, m), 2.85 (1H, m), 2.25 (1H, m), 1.85-1.65 (2H, m), 1.5-1.15 (12H, m)

MS (APCI) m/z 354, 356 $[M+H]^+$

Preparations 15 to 19

The following compounds of the general formula shown below were prepared by a method similar to that described for preparation 1 using the appropriate amine and 2-amino-4,6-dichloropyrimidine. The reactions were monitored by TLC analysis and were heated to reflux for 3 to 18 hours.

| No. | NRR' | Name | Yield | LRMS m/z |
|---|---|---|---|---|
| 15 | (structure) | tert-Butyl [(3R)-1-(2-amino-6-chloropyrimidin-4-yl)pyrrolidin-3-yl]methyl-carbamate | 100% | 328 |
| 16 | (structure) | 6-Chloro-$N^4$-(3,3-dimethylbutyl)-pyrimidine-2,4-diamine | 99% | 229 |
| 17 | (structure) | 6-Chloro-$N^4$-ethylpyrimidine-2,4-diamine | 73% | 173 |

-continued

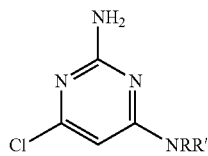

| No. | NRR' | Name | Yield | LRMS m/z |
|---|---|---|---|---|
| 18 | (3-fluorobenzyl)NH | 6-Chloro-N⁴-(3-fluorobenzyl)pyrimidine-2,4-diamine | 75% | 253 |
| 19 | (2,2-dimethylpropyl)NH | 6-Chloro-N⁴-(2,2-dimethylpropyl)pyrimidine-2,4-diamine | 66% | 213 |

Alternative method for preparation 15: tert-Butyl [(3R)-1-(2-amino-6-chloropyrimidin-4-yl)pyrrolidin-3-yl]methylcarbamate

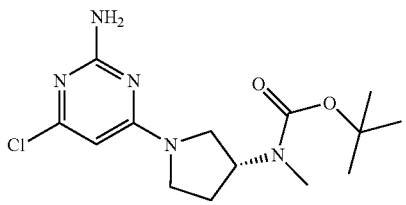

A suspension of 2-amino-4,6-dichloropyrimidine (3.62 g, 22.1 mmol) and the amine of preparation. 47 (5.40 g, 27.0 mmol) in ethanol (45 ml) was treated with TEA (4.62 ml, 33.1 mmol) and the resulting mixture heated at 80° C. for 1 hour. The reaction was cooled to room temperature and partitioned between ethyl acetate and water. The organic phase was separated and the aqueous extracted with further ethyl acteate. The combined organic extracts were dried (magnesium sulphate) and the solvent removed in vacuo to give an orange oil. Trituration with di-isopropyl ether gave a pale yellow solid which was filtered and dried in vacuo to give the title compound (7.0 g, 87%).

$^1$H NMR (400 MHz, DMSO$_{d6}$): δ 5.77 (1H, s), 4.60 (1H, br m), 3.27 (4H, br m), 2.70 (3H, s), 2.02 (2H, br m), 1.39 (9H, s) ppm.

MS (ESI) m/z 327 [M+H]$^+$

Preparation 20: N-[(3S)-1-Benzylpyrrolidin-3-yl]-N'-(3,3-dimethylbutyl)pyrimidine4,6-diamine

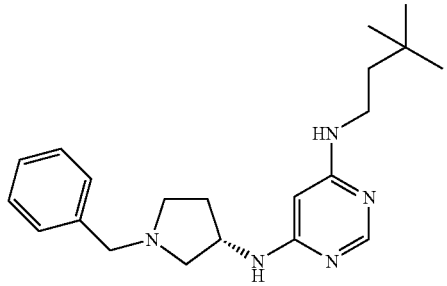

A solution of the title compound of preparation 9 (2.7 g, 9.4 mmol), 3,3-dimethylbutan-1-amine (6.3 mL, 46 mmol) and DIPEA (1.63 mL, 9.4 mmol) in NMP (100 mL) was heated to 150° C. in a sealed vessel for 24 hours. The reaction mixture was diluted with water (500 mL) and extracted with ethyl acetate (3×250 mL). The combined organic layers were washed with water (2×400 mL) followed by saturated aqueous sodium chloride (500 mL), dried (MgSO$_4$) and concentrated in vacuo. The residue was triturated with diethyl ether and the resulting solid collected by filtration to yield the title compound as a white powder (2.15 g, 65%).

MS (APCI) m/z 354 [M+H]$^+$

Preparation 21: N-[(3R)-1-Benzylpyrrolidin-3-yl]-N'-(3,3-dimethylbutyl)pyrimidine4,6-diamine

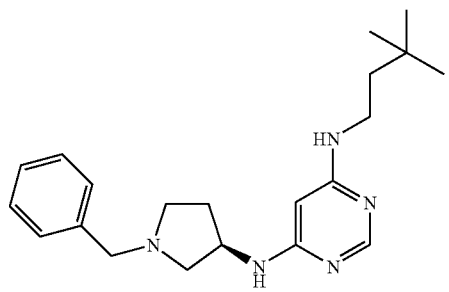

The title compound was prepared by a method similar to that described for preparation 20, using the title compound of preparation 8, in 48% yield.

MS (APCI) m/z 354 [M+H]$^+$

Preparation 22: tert-Butyl {1-[6-(cyclopropylmethyl-amino)-primidin-4-yl]-azetidin-3-yl}-methyl-carbamate

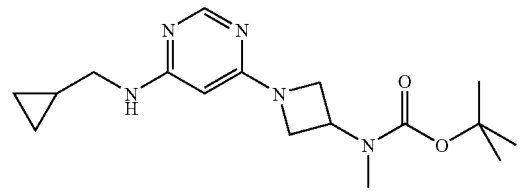

To a 5 mL reacti-vial™ containing the title compound of preparation 1 (100 mg, 0.33 mmol) and cyclopropylmethylamine (50 mg, 0.68 mmol) in DMSO (3 mL) was added TEA (94 μL, 0.68 mmol) and the solution was heated at 140° C. for 18 hours. The reaction was allowed to cool to ambient temperature, loaded onto a 5 g SCX column, eluted with MeOH (100 mL) followed by 2M ammonia in MeOH (100 mL). Fractions containing product (as judged by TLC) were combined and evaporate to give a crude orange oil. The crude product was purified by flash column chromatography on silica gel eluting with DCM:MeOH (99:1 changing to 96:4 by volume) to yield the title compound as a colourless oil (75 mg, 67%).

$^1$H NMR (400MHz, CDCl$_3$): δ 8.13 (1H, s), 5.08 (1H, s), 4.79 (1H, br s), 4.20 (2H, t), 4.01 (2H, m), 3.04 (2H, t), 2.93 (3H, s), 1.46 (9H, s), 1.05 (1H, m), 0.55 (2H, m), 0.24 (2H, m) ppm.

MS (APCI) m/z 334 [M+H]$^+$

Preparation 23: tert-Butyl {1-[6-(3-fluoro-benzylamino)-pyrimidin4-yl]-azetidin-3-yl}-methyl-carbamate

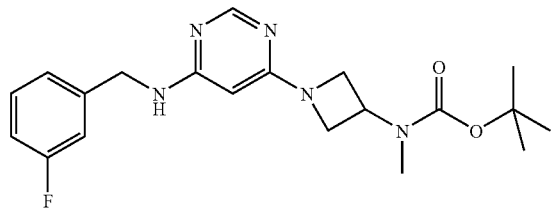

To a 5 ml reacti-vial™ containing the title compound of preparation 1 (100 mg, 0.33 mmol) and 3-fluorobenzylamine (76 μL, 0.68 mmol) in DMSO (3 mL) was added TEA (9 μL, 0.68 mmol) and the solution was heated at 140° C. for 18 hours. The reaction was allowed to cool to ambient temperature and concentrated in vacuo to obtain crude product as a viscous orange oil. The crude product was purified by flash column chromatography on silica gel eluting with DCM:MeOH (99:1 changing to 97:3 by volume) to yield the title compound as a light beige coloured solid (49 mg, 38%).

$^1$H NMR (400 MHz, CDCl$_3$): δ 8.18 (1H, s), 7.30 (1H, m), 7.09 (1H, m), 7.02 (1H, d), 6.97 (1H, m), 5.90 (1H, s), 5.0 (1H, br d), 4.46 (2H, d), 4.17 (2H, t), 3.98 (2H, m), 2.92 (3H, s), 1.47 (9H, s) ppm.

MS (APCI) m/z 388 [M+H]$^+$

Preparation 24: tert-Butyl (4aR*,7aR*)-6-{(2-amino-6-[(3,3-dimethylbutyl)amino]pyrimidin-4yl}octahydro-1H-pyrrolo[3,4-b]pyridine-1-carboxylate

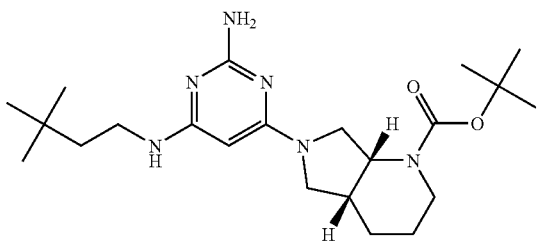

To a solution of the title compound of preparation 14 (60 mg, 0.17 mmol) in DMSO (150 μL) was added 3,3-dimethylbutan-1-amine (229 μL, 1.7 mmol) and the reaction mixture was heated to 120° C. in a sealed vessel for 48 hours. The reaction mixture was diluted with water (4 mL) and extracted with ethyl acetate (4 mL). The organic extract was dried (MgSO$_4$) and concentrated in vacuo. The residue was dissolved in MeOH (0.5 ml) and purified using a phenomomnex HPLC C-18 column eluting with acetonitrile:water (5:95 changing to 95:5 by volume containing 0.1% TFA by volume) to yield the title compound as a gum (45 mg, 63%).

$^1$H NMR (400MHz, CDCl$_3$): δ 8.41-8.33 (1H, m), 7.6-7.3 (1H, m), 6.15 (1H, br s) 4.92-4.69 (1H, m), 4.65 (1H, s), 4.05 (1H, d), 3.89-3.19 (5H, m), 3.17-3.09 (2H, m), 2.77 (1H, t), 2.39-2.19 (1H, m), 1.88-1.65 (2H, m), 1.62-1.51 (2H, m), 1.49 (9H, s), 1.44-1.17 (1H, m) 0.97 (9H, s) ppm.

MS (ESI) m/z 419 [M+H]hu +

Preparation 25: tert-Butyl (1-{2-amino-6-[(2,2-dimethylproyl)amino]pyrimidin-4-yl}azetidin-3-yl)methyl-carbamate

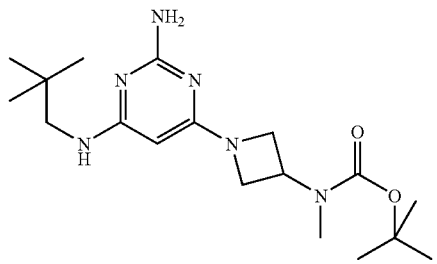

To a solution of the title compound of preparation 12 (40 mg, 0.13 mmol) in DMSO (150 μL) was added isopropylamine (150 μL, 1.7 mmol) and the resulting mixture was heated to 120° C. in a sealed vessel for 48 hours. The reaction mixture was concentrated in vacuo to give a brown gum. The residual gum was purified by flash column chromatography on silica gel eluting with DCM:MeOH:0.880 ammonia (990:10:1 changing to 190:10:1 by volume) to yield the title compound as a gum (20 mg, 42%).

$^1$H NMR (400 MHz, CD$_3$OD): δ 4.83 (1H, s), 4.13 (2H, t), 3.97 (2H, dd), 3.01 (2H, s), 2.93 (3H, s), 1.46 (9H, s), 0.94 (9H, s) ppm.

MS (ESI) m/z 365 [M+H]$^+$

Preparation 26: tert-Butyl [1-(2-amino-6-isopropylamino-pyrimidin4-yl)-azetidin-3-yl]-methyl-carbamate

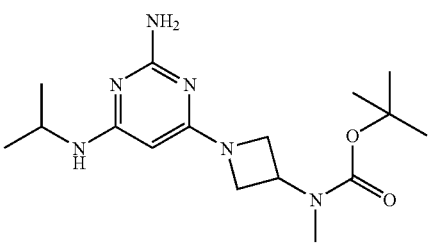

To a solution of the title compound of preparation 12 (40 mg, 0.13 mmol) in DMSO (150 μL) was added isopropylamine (150 μL, 1.7 mmol) and the resulting mixture was heated to 120° C. in a sealed vessel for 48 hours. The reaction mixture was concentrated in vacuo to give a brown gum. The residual gum was purified by flash column chromatography on silica gel eluting with DCM:MeOH:0.880 ammonia (990:10:1 changing to 190:10:1 by volume) to yield the title compound as a gum (22 mg, 50%).

$^1$H NMR (400MHz, CDCl$_3$): δ 4.95 (1H, br s), 4.67 (1H, s), 4.48 (2H, br s), 4.33 (1H, br d), 4.16 (2H, br t), 3.95 (2H, dd), 3.72 (1H, m), 2.92 (3H, s), 1.46 (9H, s) 1.19 (6H, d) ppm.

MS (APCI) m/z 337 [M+H]$^+$

Preparation 27: tert-Butyl {1-[2-amino-6-(3,3,3-trifluoro-propylamino)-pyrimidin-4-yl]-azetidin-3-yl}-methyl-carbamate

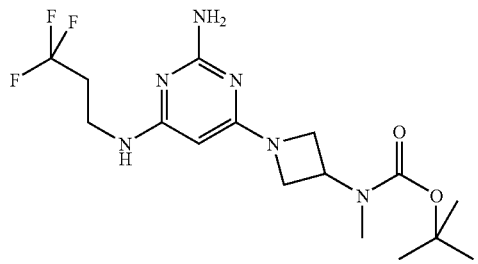

To a solution of the title compound of preparation 12 (30 mg, 0.1 mmol) in EtOH (200 μL) was added 3,3,3 trifluoropropylamine hydrochloride (48 mg, 0.3 mmol) followed by TEA (100 μL, 0.7 mmol) and the resulting mixture was heated under microwave irradiation to 130° C. in a sealed vessel for 90 min. The reaction mixture was concentrated in vacuo to give a brown gum. The residual gum was purified by flash column chromatography eluting with DCM:MeOH:880 ammonia (99:1:0.1 changing to 95:5:0.5, by volume) to yield the title compound as a gum (15 mg, 38%).

$^1$H NMR (400MHz, CD$_3$COCD$_3$): δ 5.71 (1H, br t), 5.13 (2H, br s), 4.87 (1H, br s), 4.04 (2H, t), 3.88 (2H, dd), 3.54 (2H, q), 2.91 (3H, s), 2.52 (2H, m), 1.44 (9H, s) ppm.

MS (APCI) m/z 391 [M+H]$^+$

Preparation 28: tert-Butyl {1-[2-amino-6-(cyclopropylmethyl-amino)-pyrimidin-4-yl]-azetidin-3-yl}-methyl-carbamate

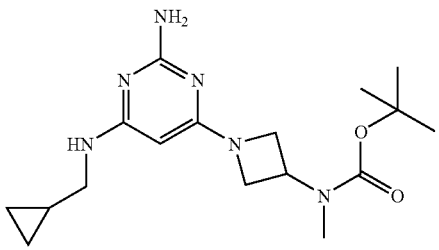

The title compound was prepared by a method similar to that described for preparation 26, using the title compound of preparation 12 and cyclopropylmethylamine, in 48% yield.

$^1$H NMR (400 MHz, CD$_3$COCD$_3$): δ 5.51 (1H, m), 5.08 (2H, br s), 4.87 (1H, br s), 4.79 (1H, s), 4.03 (2H, t), 3.87 (2H, dd), 3.08 (2H, t), 2.90 (3H, s), 1.43 (9H, s), 1.02 (1H, m), 0.42 (2H, m), 0.19 (2H, m) ppm.

MS (APCI) m/z 349 [M+H]$^+$

Preparation 29: tert-Butyl {1-[2-amino-6-(3,3-dimethyl-butylamino)-pyrimidin-4-yl]-azetidin-3-yl}-methyl-carbamate

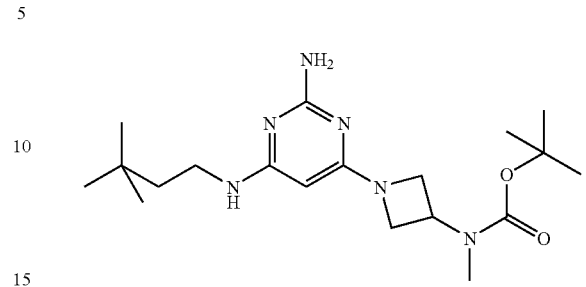

The title compound was prepared by a method similar to that described for preparation 26, using the title compound of preparation 12 and 3,3-dimethylbutan-1-amine, in 58% yield.

$^1$H NMR (400MHz, CDCl$_3$): δ 5.0 (1H, br s), 4.67 (1H, s), 4.52 (2H, br s), 4.36 (1H br t), 4.16 (2H, t), 3.96 (2H, m), 3.13 (2H, m), 2.92 (3H, s), 1.50-1.45 (11H, m), 0.95 (9H, s) ppm.

MS (APCI) m/z 379 [M+H]$^+$

Preparation 30: tert-Butyl {1-[2-amino-6-(3-fluoro-benzylamino)-pyrimidin-4-yl]-azetidin-3-yl}-methyl-carbamate

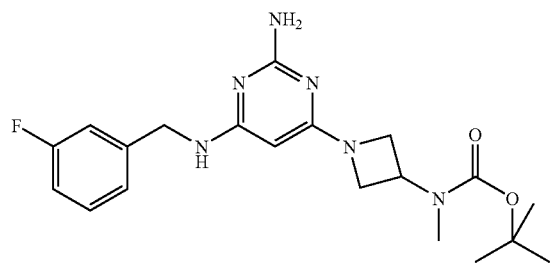

The title compound was prepared by a method similar to that described for preparation 26, using the title compound of preparation 12 and 3-fluorobenzylamine using 1,2-diethoxyethane as reaction solvent, in 53% yield.

$^1$H NMR (400 MHz, CDCl$_3$): δ 7.28 (1H, m), 7.08 (1H, d), 7.01(1H, br d), 6.95 (1H, br t), 5.15 (1H, br t), 5.00 (1H, br s), 4.80 (2H, br s), 4.64 (1H, s), 4.41 (2H, br d), 4.13 (2H, t), 3.96 (2H, dd), 2.90 (3H, s), 1.45 (9H, s) ppm.

MS (ESI) m/z 403 [M+H]$^+$

Preparation 31: tert-Butyl {1-[2-amino-6-(3-methoxy-benzylamino)-pyrimidin-4-yl]-azetidin-3-yl}-methyl-carbamate

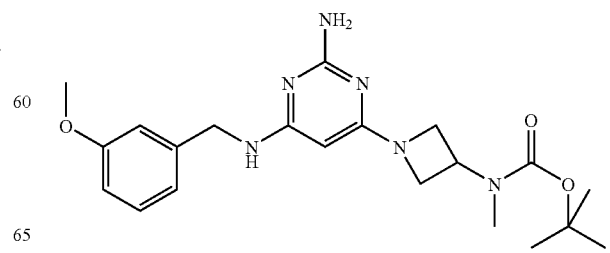

The title compound was prepared by a method similar to that described for preparation 26, using the title compound of preparation 12 and 3-methoxy-benzylamine, in 17% yield.

$^1$H NMR (400 MHz, CD$_3$COCD$_3$): δ 7.20 (1H, t), 6.93-6.89 (2H, m), 6.78 (1H, dd), 5.96 (1H, br t), 5.12 (2H, br s), 5.00-4.70 (2H, m), 4.46 (2H, d), 4.01 (2H, t), 3.86 (2H, m), 3.76 (3H, s), 2.90 (3H, s), 1.44 (9H, s) ppm.

Preparation 32: tert-Butyl {1-[2-amino-6-(cyclobutylmethyl-amino)-pyrimidin-4-yl]-azetidin-3-yl}-methyl-carbamate

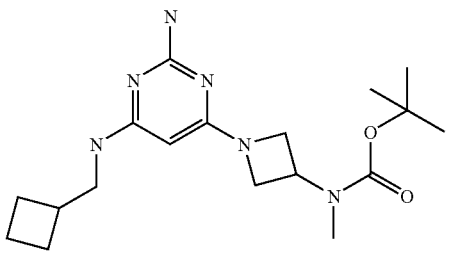

To a solution of the title compound of preparation 1 (30 mg, 0.10 mmol) in DMSO (150 μL) was added cyclobutylmethylamine hydrogen chloride (127 mg, 1 mmol) followed by DIPEA (300 μL, 1.76 mmol) and the resulting mixture was heated to 120° C. in a sealed vessel for 48 hours. The reaction mixture was concentrated in vacuo to give a gum. The residual gum was purified by flash column chromatography on silica gel eluting with DCM:MeOH:0.880 ammonia (990: 10:1 changing to 190:10:1 by volume) to yield the title compound as a gum (12 mg, 33%).

$^1$H NMR (400 MHz, CD$_3$COCD$_3$): δ 5.52 (1H, m), 5.13 (2H, br s), 4.87 (1H, brs), 4.79 (1H, s), 4.05 (2H, t), 3.86 (2H, dd), 3.25 (2H, t), 2.91 (3H, s), 2.56 (1H, m), 2.05-1.97 (H, m), 1.89-1.80 (2H, m), 1.77-1.69 (2H, m), 1.44 (9H, s) ppm.
MS (ESI) m/z 363 [M+H]$^+$ Preparation 33: tert-Butyl {1-[2-amino-6-(cyclopentylmethyl-amino)-pyrimidin-4-yl]-azetidin-3-yl}-methyl-carbamate

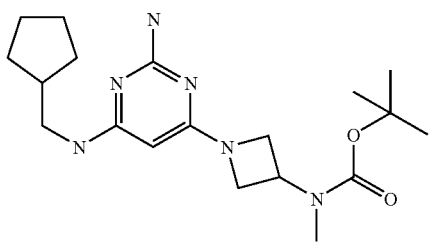

The title compound was prepared by a method similar to that described for preparation 26, using the title compound of preparation 12 and cyclopentylmethylamine hydrogen chloride, in 16% yield.

$^1$H NMR (400 MHz, CD$_3$OD): δ 4.79 (1H, s), 4.15 (2H, t), 4.00 (2H, dd), 3.10 (2H, d), 2.93 (3H, s), 2.14 (1H, m), 1.83-1.75 (2H, m), 1.69-1.53 (4H, m), 1.46 (9H, s), 1.30-1.22 (2H, m) ppm.
MS (APCI) m/z 77 [M+H]$^+$ Preparations 34 to 42

The following compounds of the general formula shown below were prepared by a method similar to that described for preparation 1 using the appropriate amine and 2-amino-4,6-dichloropyrimidine. Reactions were monitored by TLC analysis.

| No. | NRR' | Name | LRMS m/z |
|---|---|---|---|
| 34 | | tert-Butyl 4-(2-amino-6-chloro-pyrimidin-4-yl)-1,4-diazepane-1-carboxylate | 328 |
| 35 | | 6-Chloro-N$^4$-(2-methylcyclopropyl)pyrimidine-2,4-diamine | 199 |
| 36 | | 4-Chloro-6-(4-methyl-1,4-diazepan-1-yl)pyrimidin-2-amine | 242 |
| 37 | | 6-Chloro-N$^4$-(cyclopropylmethyl)pyrimidine-2,4-diamine | 254 |
| 38 | | tert-Butyl (3aR*, 7aS*)-5-(2-amino-6-chloropyrimidin-4-yl)octahydro-1H-pyrrolo[3,2-c]pyridine-1-carboxylate | 354 |
| 39 | | N$^4$-Bicyclo[1.1.1]pent-1-yl-6-chloro-pyrimidine-2,4-diamine | 211 |
| 40 | | tert-Butyl [1-(2-amino-6-chloro-pyrimidin-4-yl)piperidin-4-yl] carbamate | 328 |
| 41 | | tert-Butyl [1-(2-amino-6-chloro-pyrimidin-4-yl)-3-methylazetidin-3-yl] methylcarbamate | 328 |
| 42 | | 4-Chloro-6-(hexahydropyrrolo[1,2-a]pyrazin-2(1H)-yl)pyrimidin-2-amine | 254 |

Preparation 43: N⁴-(tert-Butyl)-6-choropyrimidine-2,4-diamine

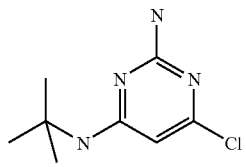

A solution of 2-amino-4,6-dichloropyrimidine (400 mg, 2.44 mmol) and t-butylamine (2.6 ml, 25.0 mmol) in NMP (1 ml) was heated in a microwave at 150° C. for 60 minutes. The reaction mixture was partitioned between water (10 ml) and ethyl acetate (10 ml), the organic phase separated, dried and reduced in vacuo. Purification by flash column chromatography on silica gel eluting with ethyl acetate:pentane (30:70 changing to 80:20 by volume) to yield the title compound as a colourless solid (494 mg, 100%).

¹H NMR (400 MHz, CDCl₃): δ 5.80 (1H, s), 4.78 (2H, bs), 1.42 (9H, s) ppm.

MS (ESI) m/z 201 [M+H]⁺

Preparation 44: 6-Chloro-N⁴-(1-methylcyclopropyl)pyrimidine-2,4-diamine

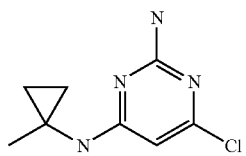

2-amino-4,6-dichloropyrimidine (508 mg, 3.1 mmol) was added to a suspension of 1-methylcyclopropylamine hydrochloride (1.0 g, 9.3 mmol) and sodium methoxide (502mg, 9.30 mmol) in NMP (3 ml). The resulting mixture was heated at 90° C. for 16 hours and then cooled to room temperature. The reaction mixture was diluted with water (20 ml) and the resulting precipitate filtered off, washed with further water (20 ml) and dried in vacuo to give the title compound as a colourless solid (280 mg, 15%).

¹H NMR (400 MHz, CDCl₃): δ 6.71 (1H, s), 1.37 (3H, s), 0.83-0.79 (2H, m), 0.72-0.65 (2H, m) ppm.

MS (ESI) m/z 199 [M+H]⁺

Preparation 45: Benzyl (3R)-3-[(tert-butoxycarbonyl)amino]pyrrolidine-1-carboxylate

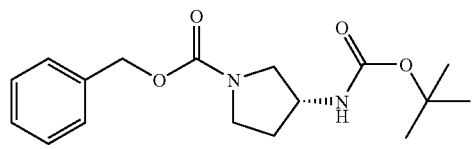

A solution of tert-Butyl (3S)-pyrrolidin-3-ylcarbamate (10.0 g, 53.7 mmol) in DCM (40 ml) was treated with TEA (14.9ml, 107 mmol) and cooled to 0° C. Benzyl chloroformate (7.6 ml, 53.7 mmol) was added dropwise and the resulting suspension was allowed to warm gradually to room temperature over a period of 18 hours. The reaction mixture was diluted with water (100 ml) and the organic phase separated. The aqueous phase was extracted with further DCM (2×50 ml) and the combined organic extracts dried (sodium sulphate) and concentrated in vacuo to give a pale yellow solid (14.6 g, 85%)

¹H NMR (400 MHz, CDCl₃): δ 7.39-7.29 (5H, m), 5.13 (2H, s), 4.58 (1H, m), 4.19 (1H, m), 3.66 (1H, m), 3.49 (1H, m), 3.25 (1H, m), 2.14 (1H, m), 1.82 (1H, m), 1.44 (9H, s) ppm.

MS (ESI) m/z 321 [M+H]⁺

Preparation 46: Benzyl (3R)-3-[(tert-butoxycarbonyl)amino]pyrrolidine-1-carboxylate

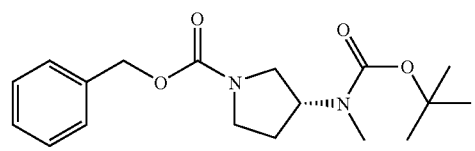

A solution of the carbamate of preparation 45 (14.6 g, 45.6 mmol) in THF (85 ml) was cooled to 0° C. and treated with potassium tert-butoxide (4.38 g, 59.27 mmol). The reaction was left to stir for 30 minutes prior to the addition of methyl iodide (4.26 ml, 59.3 mmol) and then allowed to warm gradually to room temperature. The reaction mixture was partitioned between ethyl acetate (200 ml) and water (100 ml). The aqueous phase was separated and extracted with further ethyl acetate (100 ml). The combined organic extracts were washed with saturated aqueous sodium chloride (100 ml), dried (magnesium sulphate) and reduced in vacuo to give an orange oil. The oil was re-dissolved in THF (85 ml), cooled to 0° C. and treated with potassium tert-butoxide (3.00 g, 40.6 mmol). The reaction was left to stir for 30 minutes prior to the addition of methyl iodide (3.0 ml, 41.7 mmol) and then allowed to warm gradually to room temperature. The reaction mixture was partitioned between ethyl acetate (200 ml) and water (100 ml). The aqueous phase was separated and extracted with further ethyl acetate (100 ml). The combined organic extracts were washed with saturated aqueous sodium chloride (100 ml), dried (magnesium sulphate) and reduced in vacuo to give the title compound as an orange oil (15.3 g, 100%).

¹H NMR (400 MHz, CDCl₃): δ 7.35-7.26 (5H, m), 5.11 (2H, s), 4.70 (1H, m), 3.58 (2H, m), 3.34 (1H, m), 3.29 (1H, m), 2.74 (3H, s), 1.98 (2H, m), 1.43 (9H, s) ppm.

MS (ESI) m/z 335 [M+H]⁺

Preparation 47: tert-Butyl methyl[(3R)-pyrrolidin-3-yl]carbamate

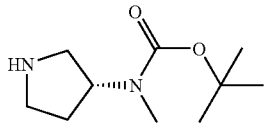

A solution of the carbamate of preparation 46 (15.58 g, 46.6 mmol) in ethanol (150 ml) was hydrogenated in the presence of 5% Pd/C (1 g) at 50 psi at room temperature for a period of 18 hours. Further Pd/C (500 mg) was added and the resulting mixture hydrogenated under the same conditions for a further 26 hours. The catalyst was filtered off and the filtrate concentrated in vacuo. Purification by chromatography (DCM:MeOH:0.880 ammonia (100:0:0 changing to 90:10:1 by volume) gave the title compounds as a pale yellow oil (5.85 g, 62%).

$^1$H NMR (400 MHz, CDCl$_3$): δ 4.56 (1H, m), 3.06 (2H, m), 2.87 (1H, m), 2.79 (1H, m), 2.78 (3H, s), 2.54 (1 H, s), 1.95 (1H, m), 1.73 (1H, m), 1.43 (9H, s) ppm.

MS (ESI) m/z 201 [M+H]$^+$

Example 1

N-(3,3-Dimethylbutyl)-6-(4-methylpiperazin-1-yl)pyrimidin-4-amine

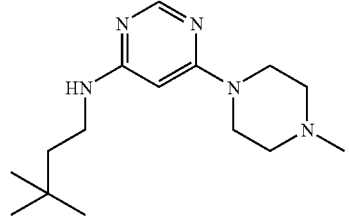

A solution of the title compound (110 mg, 0.52 mmol) of preparation 6 in NMP (2 mL) was treated with DIPEA (135 μL, 0.78 mmol) and 3,3-dimethylbutan-1-amine (347 μL, 2.6 mmol) and heated to 150° C. for 18 hours in a sealed vessel. The reaction mixture was cooled to ambient temperature and partitioned between ethyl acetate (20 mL) and water (20 mL). The organic fraction was washed with saturated aqueous sodium chloride (20 mL) dried (MgSO$_4$) and concentrated in vacuo. The residue was purified by flash column chromatography on silica gel eluting with DCM:MeOH:0.880 ammonia (90:10:1 by volume) to yield the title compound as a gum (57 mg, 40%).

$^1$H NMR (400 MHz, CD$_3$OD): δ 7.95 (1H, s), 5.56 (1H, s), 3.51 (4H, m), 3.23 (2H, m), 2.74 (4H, m), 2.30 (3H, s), 1.49 (2H, m), 0.95 (9H, s) ppm.

MS (APCI) m/z 278 [M+H]$^+$

Examples 2 to 5

The following compounds were prepared by a method similar to that described for example 1 using the appropriate starting material.

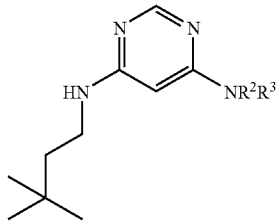

| No. | Preparation No. of Starting material. | NR$^2$R$^3$ | Name | Yield | LRMS m/z |
|---|---|---|---|---|---|
| 2 | 3 | | 6-[(3S)-3-(Dimethylamino)pyrrolidin-1-yl]-N-(3,3-dimethylbutyl)pyrimidin-4-amine | 20% | 292 |
| 3 | 4 | | N-(3,3-Dimethylbutyl)-6-[(3aR*,6aS*)-5-methylhexahydropyrrolo[3,4-c]pyrrol-2(1H)-yl]pyrimidin-4-amine | 24% | 304 |

-continued

| | Preparation No. of Starting | | | | LRMS |
|---|---|---|---|---|---|
| 4 | 5 | | 6-[3-(Dimethylamino)azetidin-1-yl]-N-(3,3-dimethylbutyl)pyrimidin-4-amine | 41% | 278 |
| 5 | 7 | | N-(3,3-Dimethylbutyl)-6-[(1S,4S)-5-methyl-2,5-diazabicyclo[2.2.1]hept-2-yl]pyrimidin-4-amine | 3% | 290 |

Example 6

N-(3,3-Dimethylbutyl)-N'-[(3S)-pyrrolidin-3-yl]pyrimidine-4,6-diamine

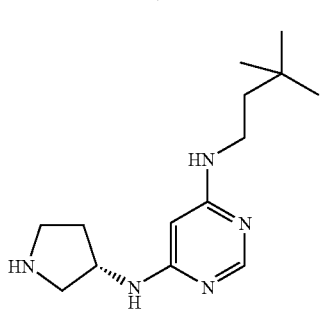

A solution of the compound of preparation 20 (2.15 g, 6.1 mmol) in EtOH (40 mL) and MeOH (20 mL) was cooled to 0° C. and treated with palladium hydroxide (20% on carbon 100 mg) followed by ammonium formate (5.8 g, 91 mmol) and heated to reflux for 2 hours. The reaction mixture was cooled to ambient temperature filtered and the filtrate concentrated in vacuo. The residue was purified directly by SCX resin, eluting non-basic compounds with MeOH and the basic compounds with 1N ammonia in MeOH.

The basic washings were concentrated in vacuo and purified by flash column chromatography on silica gel eluting with DCM:MeOH:0.880 ammonia (1:0:0 changing to 80:20:1, by volume) to yield the title compound as a white powdery solid (1.2 g, 75%).

$^1$H NMR (400 MHz, CD$_3$OD): δ 7.9 (1H, s), 5.4 (1H, s), 4.1 (1H, m), 3.2 (2H m), 3.1 (1H, m), 3.0 (1H, m), 2.9 (1H, m), 2.7 (1H, m), 2.1 (1H, m), 1.7 (1H, m), 1.5 (2H, m), 1.0 (9H, s) ppm.

Accurate mass: found 264.2181, C$_{14}$H$_{26}$N$_5$ requires 264.2183.

Example 7

N-(3,3-Dimethylbutyl)-N'-[(3R)-pyrrolidin-3-yl]pyrimidine-4,6-diamine

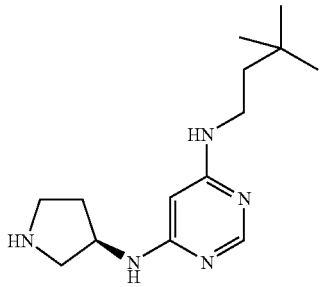

The title compound was prepared by a similar method to that described for example 6, using the title compound of preparation 21, in 70% yield.

$^1$H NMR (400 MHz, CD$_3$OD): δ 7.9 (1H, s), 5.4 (1H, s), 4.1 (1H, m), 3.2 (2H m), 3.1 (1H, m), 3.0 (1H, m), 2.9 (1H, m), 2.7 (1H, m), 2.1 (1H, m), 1.7 (1 H, m), 1.5 (2H, m), 1.0 (9H, s) ppm.

MS (APCI) m/z 264 [M+H]$^+$

Example 8

N-(3,3-Dimethylbutyl)-N'-[(3R)-1-methylpyrrolidin-3-yl]pyrimidine-4,6-diamine

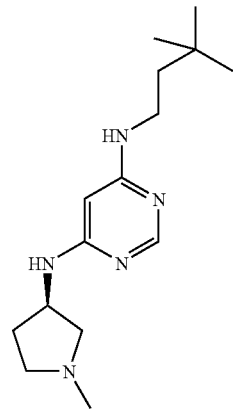

A suspension of the compound of example 7 (38 mg, 0.144 mmol) in THF (1.5 mL) containing aqueous formaldehyde (11 μL, 0.144 mmol, 37% in water) and acetic acid (8.3 μL, 0.144 mmol) was treated with sodium triacetoxyborohydride (37 mg, 0.173 mmol) and stirred at ambient temperature for 10 min. The reaction mixture was applied directly to SCX resin, eluting non-basic compounds with MeOH and the basic compounds with 1 N ammonia in MeOH. The basic washings were concentrated in vacuo and purified by flash column chromatography on silica gel eluting with DCM:MeOH: 0.880 ammonia (1:0:0 changing to 40:10:1, by volume) further purification on reverse phase silica eluting with water: acetonitrile (1:0 changing to 19:1 by volume) gave the title compound as a white solid (14 mg, 35%).

$^1$H NMR (400 MHz, CD$_3$OD): δ 7.9 (1H, s), 5.41H, s), 4.2 (1H, m), 3.2 (2H, m), 2.9 H, m), 2.8 (1H, m), 2.5 (2H, m), 2.4 (4H, m), 1.7 (1H, m), 1.5 (2H, m) 1.1 (9H, s) ppm.

MS (APCI) m/z 278 [M+H]$^+$, 276 [M-H]$^{31}$

Example 9

N$^4$-(Cyclopropylmethyl)-6-[(3R)-3-(methylamino) pyrrolidin-1-yl]pyrimidine-2,4-diamine

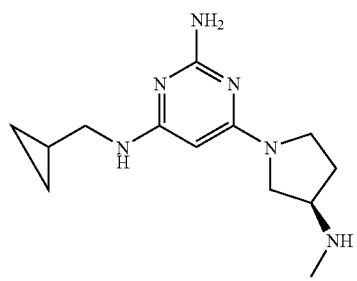

A solution of the compound of preparation 15 (120 mg, 0.38 mmol) in NMP (2 mL) was treated with DIPEA (191 μL, 1.1 mmol) and 1-cyclopropylmethylamine (99 μL, 1.15 mmol) and heated to 150° C. in a sealed vessel for 18 hours. The reaction mixture was diluted with ethyl acetate (50 mL) and washed with water (4×50 mL) and saturated aqueous sodium chloride (50 mL), dried (MgSO$_4$) and concentrated in vacuo to give the crude intermediate tert-butyloxycarbonyl-protected compound. This crude material was dissolved in DCM (2 mL), treated with trifluoroacetic acid (2 mL) and stirred at ambient temperature for 3 h after which time the reaction mixture was concentrated in vacuo. The residue was purified directly by SCX resin, eluting non-basic compounds with MeOH and the basic compounds with 2 N ammonia in MeOH. The basic washings were concentrated in vacuo and purified by flash column chromatography on silica gel eluting with DCM:MeOH:0.880 ammonia (1:0:0 changing to 170: 30:3, by volume) to yield the title compound as a white foam (16 mg, 17%).

$^1$H NMR (400 MHz, CD$_3$OD): δ 4.89 (1H, s), 3.63 (1H, m), 3.55 (1H, m), 3.47 (1H, m), 3.39 (1H, m), 3.23 (1H, m), 3.05 (2H, d), 2.42 (3H, s), 2.21 (1H, m), 1.88 (1H, m), 1.06 (1H, m), 0.52 (2H, q), 0.23 (2H, q) ppm.

MS (APCI) m/z 248 [M+H]$^+$

Alternative method for example 9

N$^4$-(Cyclopropylmethyl)-6-[(3R)-3-(methylamino) pyrrolidin-1-yl]pyrimidine-2,4-diamine

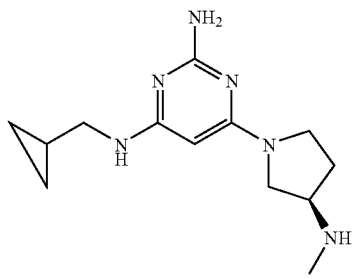

A suspension of the compound of preparation 15 (1.8 g, 5.5 mmol) in cyclopropylmethanamine (5.4 ml, 62.3 mmol) and TEA (1.53 ml, 11 mmol) was heated in a sealed pressure vessel at 120° C. for 24 hours. The excess amine was removed in vacuo and the residue partitioned between water (100 ml) and DCM (100 ml). The aqueous phase was separated and extracted with further DCM (100 ml). The combined organic extracts were washed with saturated aqueous sodium chloride (100 ml) and the solvent removed in vacuo. Purification by flash column chromatography on silica gel eluting with DCM:MeOH:0.880 ammonia (98:2:0 changing to 95:5:0.2, by volume) gave the to give the intermediate tert-butyloxycarbonyl-protected compound (1.55 g, 77%).

$^1$H NMR (400 MHz, CD$_3$OD): δ 4.89 (1H, s), 4.71 (1H, m), 3.64 (2H, m), 3.32 (2H, m), 3.07 (2H, d), 2.80 (3H, s), 2.13 (2H, m), 1.46 (9H, s), 1.05 (1H, m), 0.52 (2H, m), 0.23 (2H, m) ppm.

MS (APCI) m/z 363 [M+H]$^+$

A solution of the intermediate tert-butyloxycarbonyl-protected compound (6.18 g, 16.6 mmol) in methanol (15 ml) was treated with 4 M HCl in 1,4-dioxan (42 ml, 168 mmol) and the resulting solution was left to stir at room temperature (exotherm observed on addition of the HCl) for 18 hours. The solvent was removed in vacuo and the residue partitioned between 0.880 ammonia (50 ml) and DCM (400 ml). The aqueous phase was separated and extracted with further DCM (200 ml). The combined organic extracts were dried (sodium sulphate) and the solvent removed in vacuo to give a pale yellow oil (4.00 g, 92%).

Example 9a

N$^4$-(Cyclopropylmethyl)-6-[(3R)-3-(methylamino) pyrrolidin-1-yl]pyrimidine-2,4-diamine L-tartrate

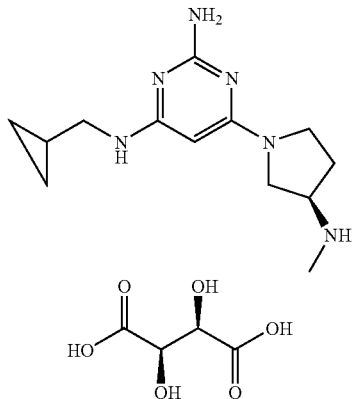

A solution of the compound of example 9 (10.14 g, 38.65 mmol) in methanol (340 ml) was treated with a solution of L(+) tartaric acid in (5.8 g, 38.65 mmol) in methanol (50 ml). The resulting suspension was stirred at room temperature for 30 minutes and the resulting solid filtered off and dried in vacuo. The solid was dissolved in the minimum volume of boiling water (22 ml) and then methanol was added until a permanent ppt was observed (102 ml). The resulting suspension was allowed to cool gradually to room temperature and the solid filtered and dried in vacuo for 50° C. for 3 days and then allowed to equilibrate at room temperature in air for a further 2 days to give the title compounds as a colourless solid (14.15 g, 89%)

$^1$H NMR (400 MHz, CD$_3$OD): δ 6.41 (1H, br s), 5.72 (2H, br s), 4.81(1H, s), 3.92 (2H, s), 3.58 (2H, m), 3.40 (1H, m), 3.32 (2H, m), 3.03 (2H, m), 2.48 (3H, s), 2.18 (1H, m), 1.95 (1H, m), 0.96 (1H, m), 0.39 (2H, m), 0.12 (2H, m) ppm.

MS (APCI) m/z 263 [M+H]$^+$

Examples 10 to 12

The following compounds were prepared by a method similar to that described for example 9 using the title compound of preparation 15 and the appropriate amine starting material.

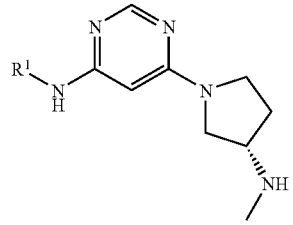

| No. | R$^1$ | Names | Yield | LRMS m/z |
|-----|-------|-------|-------|----------|
| 10 | isobutyl | N$^4$-Isobutyl-6-[(3R)-3-(methylamino)pyrrolidin-1-yl]pyrimidine-2,4-diamine | 24% | 265 |
| 11 | 2,2-dimethylpropyl | N$^4$-(2,2-Dimethylpropyl)-6-[(3R)-3-(methylamino)pyrrolidin-1-yl]pyrimidine-2,4-diamine | 34% | 279 |
| 12 | Et | N$^4$-Ethyl-6-[(3R)-3-(methylamino)pyrrolidin-1-yl]pyrimidine-2,4-diamine | 27% | 237 |

Examples 13 to 15

The following compounds were prepared by a method similar to that described for example 9, using the compound of preparation 10 and the appropriate amine starting material.

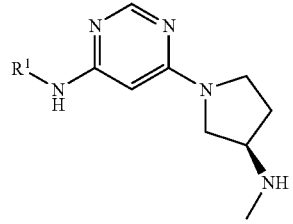

| No. | R$^1$ | Name | Yield | LRMS m/z |
|-----|-------|------|-------|----------|
| 13 | Et | N-Ethyl-6-[(3R)-3-(methylamino)pyrrolidin-1-yl]pyrimidin-4-amine | 64% | 222 |
| 14 | isobutyl | N-Isobutyl-6-[(3R)-3-(methylamino)pyrrolidin-1-yl]pyrimidin-4-amine | 32% | 250 |
| 15 | cyclopropylmethyl | N-(Cyclopropylmethyl)-6-[(3R)-3-(methylamino)pyrrolidin-1-yl]pyrimidin-4-amine | 17% | 248 |

Examples 16 to 17

The following compounds were prepared by a method similar to that described for example 9 using the compound of preparation 11 and the appropriate amine starting material.

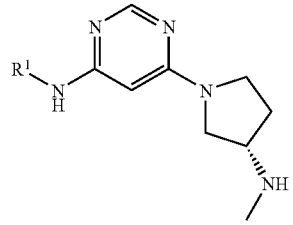

| No. | R$^1$ | Name | Yield | LRMS m/z |
|-----|-------|------|-------|----------|
| 16 | Et | N-Ethyl-6-[(3S)-3-(methylamino)pyrrolidin-1-yl]pyrimidin-4-amine | 28% | 222 |
| 17 | 3,3-dimethylbutyl | N-(3,3-Dimethylbutyl)-6-[(3S)-3-(methylamino)pyrrolidin-1-yl]pyrimidin-4-amine | 26% | 278 |

Example 18

6-[(3R)-3-(Dimethylamino)pyrrolidin-1-yl]-N-(3,3-dimethylbutyl)pyrimidin-4-amine

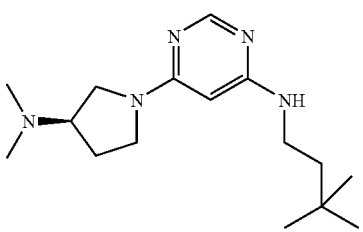

A solution of the title compound of preparation 2 (120 mg, 0.53 mmol) in NMP (2 mL) was treated with DIPEA (276 μL 1.59 mmol) 3,3-dimethylbutan-1-amine (213 μL, 1.59 mmol) and heated to 150° C. in a sealed vessel for 72 hours. The reaction mixture was cooled and purified directly by SCX resin, eluting non-basic compounds with MeOH and the basic compounds with 2 N ammonia in MeOH. The basic washings were concentrated in vacuo and purified by flash column chromatography on silica gel eluting with DCM:MeOH: 0.880 ammonia (1:0:0 changing to 40:10:1, by volume) to yield the title compound as a gum (72 mg, 47%).

$^1$H NMR (400 MHz, CD$_3$OD): δ 7.92 (1H, s), 5.30 (1H, s), 3.72 (1H, m), 3.61 (1H, m), 3.37 (1H, m), 3.24 (2H, m), 3.17 (1H, m), 2.89 (1H, m), 2.32 (6H, s), 2.25 (1H, m), 1.87 (1H, m) 1.52 (2H, m), 0.98 (9H, s), ppm.

MS (APCI) m/z 292 [M+H]$^+$

Examples 19 to 22

The following compounds were prepared by a method similar to that described for example 18 using the title compound of preparation 2.

| No. | R$^1$ | Name | Yield | LRMS m/z |
|---|---|---|---|---|
| 19 |  | N-(Cyclopropylmethyl)-6-[(3R)-3-(dimethylamino)pyrrolidin-1-yl]pyrimidin-4-amine | 64% | 262 |
| 20 |  | 6-[(3R)-3-(Dimethylamino)pyrrolidin-1-yl]-N-isobutyl-pyrimidin-4-amine | 60% | 264 |
| 21 | Et | 6-[(3R)-3-(Dimethylamino)pyrrolidin-1-yl]-N-ethyl-pyrimidin-4-amine | 55% | 236 |
| 22 |  | 6-[(3R)-3-(Dimethylamino)pyrrolidin-1-yl]-N-(2,2-dimethylpropyl)pyrimidin-4-amine | 41% | 278 |

Example 23

N$^4$-(3,3-Dimethylbutyl)-6-[(4aR*,7aR*)-octahydro-6H-pyrrolo[3,4-b]pyridin-6-yl]pyrimidine-2,4-diamine

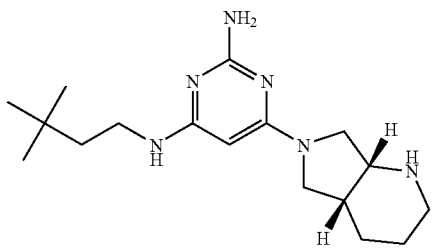

The title compound of preparation 24 (45 mg, 0.11 mmol) was dissolved in trifluoroacetic acid (2 mL) and stirred at ambient temperature for 1 hour after which time the reaction mixture was concentrated in vacuo. The residue was purified directly by SCX resin, eluting non-basic compounds with MeOH and the basic compounds with 1 N ammonia in MeOH taking 4 mL fractions to yield the title compound as a solid (25 mg, 71%).

$^1$H NMR (400 MHz, CD$_3$OD): δ 3.52-3.33 (5H, m), 3.22-3.14 (2H, m), 2.97-2.86 (1H, m), 2.66-2.57 (1H, m), 2.40-2.29 (1H, m), 1.80-1.72 (2H, m), 1.70-1.55 (1H, m), 1.53-1.43 (3H, m), 0.97 (9H, s) ppm.

MS (ESI) m/z 319 [M+H]$^+$

Example 24

N$^4$Isopropyl-6-[(4aR*,7aR*)-octahydro6H-pyrrolor[3,4-b]pyridin-6-yl]pyrimidine-2,4-diamine

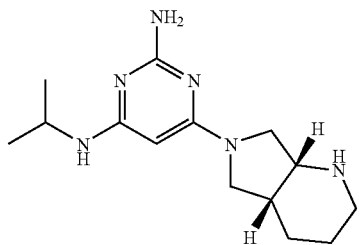

The compound was prepared by a method similar to that described for example 23 and preparation 24, reaction of the compound of preparation 14 with isopropyl amine and subsequent deprotection, in 28% yield.

$^1$H HMR (400 MHz, CD$_3$OD): δ 4.77 (1H, s), 3.86-3.74 (1H, m), 3.51-3.34 (5H, m) 2.96-2.86 (1H, m), 2.66-2.56 (1H, m), 2.40-2.26 (1H, m), 1.81-1.72 (2H, m), 1.70-1.57 (1H, m), 1.54-1.41 (1H, m), 1.18 (6H, d) ppm MS (ESI) m/z 277 [M+H]$^+$

Examples 25 to 33

The following compounds were prepared by a method similar to that described for example 23 and tion 24 by reaction of the compound of preparation 14 with an appropriate amine and subsequent deprotection.

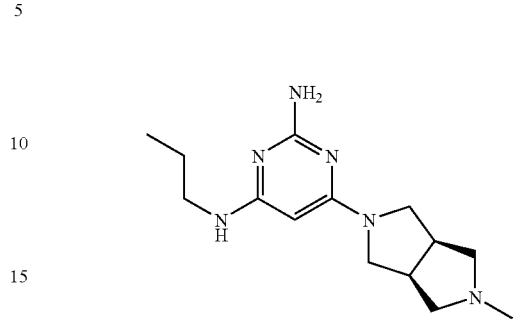

| No. | R¹ | Name | Yield | LRMS m/z |
|---|---|---|---|---|
| 25 | Me | N⁴-Methyl-6-[(4aR*,7aR*)-octahydro-6H-pyrrolo[3,4-b]pyridin-6-yl]pyrimidine-2,4-diamine | 36% | 249 |
| 26 | Et | N⁴-Ethyl-6-[(4aR*,7aR*)-octahydro-6H-pyrrolo[3,4-b]pyridin-6-yl]pyrimidine-2,4-diamine | 11% | 263 |
| 27 |  | N⁴-Isobutyl-6-[(4aR*,7aR*)-octahydro-6H-pyrrolo[3,4-b]pyridin-6-yl]pyrimidine-2,4-diamine | 32% | 291 |
| 28 |  | N⁴-(Cyclopropylmethyl)-6-[(4aR*,7aR*)-octahydro-6H-pyrrolo[3,4-b]pyridin-6-yl]pyrimidine-2,4-diamine | 39% | 289 |
| 29 |  | N⁴-(3-Methylbutyl)-6-[(4aR*,7aR*)-octahydro-6H-pyrrolo[3,4-b]pyridin-6-yl]pyrimidine-2,4-diamine | 62% | 305 |
| 30 |  | N⁴-(2,2-Dimethylpropyl)-6-[(4aR*,7aR*)-octahydro-6H-pyrrolo[3,4-b]pyridin-6-yl]pyrimidine-2,4-diamine | 29% | 305 |
| 31 |  | N⁴-Cyclopropyl-6-[(4aR*,7aR*)-octahydro-6H-pyrrolo[3,4-b]pyridin-6-yl]pyrimidine-2,4-diamine | 19% | 275 |
| 32 |  | N⁴-Cyclobutyl-6-[(4aR*,7aR*)-octahydro-6H-pyrrolo[3,4-b]pyridin-6-yl]pyrimidine-2,4-diamine | 43% | 289 |
| 33 |  | N⁴-(Cyclopentylmethyl)-6-[(4aR*,7aR*)-octahydro-6H-pyrrolo[3,4-b]pyridin-6-yl]pyrimidine-2,4-diamine | 11% | 317 |

Example 34

6-[(3aR*,6aS*)-5-Methylhexahydropyrrolo[3,4-c]pyrrol-2(1H)-yl]-N⁴-propylpyrimidine-2,4-diamine

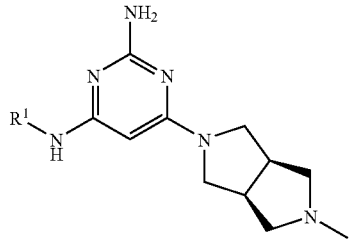

To a solution of the title compound of preparation 13 (20 mg, 0.08 mmol) in DMSO (75 µL) was added 1amine (75 µL, 1 mmol) and the mixture was heated to 120° C. in a sealed vessel for 48 hours. The reaction mixture was concentrated in vacuo to give a brown gum. The residual gum was purified by flash column chromatography on silica gel eluting with DCM:MeOH: 0.880 ammonia (990:10:1 changing to 90:10:1, by volume) to yield the title compound as a gum (10 mg, 45%).

¹H NMR (400 MHz, CD₃COCD₃): δ 5.28 (1H, br t), 4.97 (3H, m), 3.51 (2H, m), 3.20 (4H, m), 2.83 H, m), 2.51 (2H, m), 2.41 (2H, m), 2.22 (3H, s) 1.56 (2H, m), 0.92 (3H, t) ppm MS (ESI) m/z 277 [M+H]⁺

Examples 35 to 43

The following compounds were prepared by a method similar to that described for example 34 using the compound of preparation 13 and the appropriate amine starting material.

| No. | R¹ | Name | Yield | LRMS m/z |
|---|---|---|---|---|
| 35 | Me | N⁴-Methyl-6-[(3aR*,6aS*)-5-methylhexahydro-pyrrolo[3,4-c]pyrrol-2(1H)-yl]pyrimidine-2,4-diamine | 30% | 249 |
| 36 | Et | N⁴-Ethyl-6-[(3aR*,6aS*)-5-methylhexahydro-pyrrolo[3,4-c]pyrrol-2(1H)-yl]pyrimidine-2,4-diamine | 62% | 263 |
| 37 |  | N⁴-Isobutyl-6-[(3aR*,6aS*)-5-methylhexahydro-pyrrolo[3,4-c]pyrrol-2(1H)-yl]pyrimidine-2,4-diamine | 52% | 291 |

53
-continued

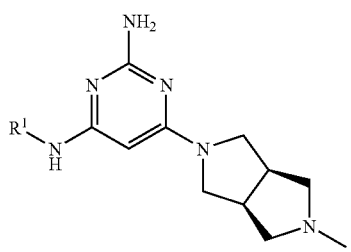

| No. | R¹ | Name | Yield | LRMS m/z |
|---|---|---|---|---|
| 38 | cyclopropylmethyl | N⁴-(Cyclopropylmethyl)-6-[(3aR*,6aS*)-5-methylhexahydro-pyrrolo[3,4-c]pyrrol-2(1H)-yl]pyrimidine-2,4-diamine | 78% | 289 |
| 39 | 2,2-dimethylpropyl | N⁴-(2,2-Dimethylpropyl)-6-[(3aR*,6aS*)-5-methylhexahydro-pyrrolo[3,4-c]pyrrol-2(1H)-yl]pyrimidine-2,4-diamine | 46% | 305 |
| 40 | 3,3-dimethylbutyl | N⁴-(3,3-Dimethylbutyl)-6-[(3aR*,6aS*)-5-methylhexahydro-pyrrolo[3,4-c]pyrrol-2(1H)-yl]pyrimidine-2,4-diamine | 48% | 319 |
| 41 | 3-methylbutyl | N⁴-(3-Methylbutyl)-6-[(3aR*,6aS*)-5-methylhexahydro-pyrrolo[3,4-c]pyrrol-2(1H)-yl]pyrimidine-2,4-diamine | 54% | 305 |
| 42 | cyclopropyl | N⁴-Cyclopropyl-6-[(3aR*,6aS*)-5-methylhexahydro-pyrrolo[3,4-c]pyrrol-2(1H)-yl]pyrimidine-2,4-diamine | 27% | 275 |
| 43 | cyclobutyl | N⁴-Cyclobutyl-6-[(3aR*,6aS*)-5-methylhexahydro-pyrrolo[3,4-c]pyrrol-2(1H)-yl]pyrimidine-2,4-diamine | 48% | 289 |

Example 44

Cyclopropylmethyl-[6-(3-methylamino-azetidin-1-yl)-pyrimidin-4-yl]-amine

A solution of the title compound of preparation 22 (70 mg, 0.21 mmol) in DCM (5 mL) was treated with trifluoroacetic acid (0.5 mL) and stirred at ambient temperature for 2 hours after which time the reaction mixture was concentrated in vacuo. The residue was purified directly by SCX resin, eluting non-basic compounds with MeOH and the basic compounds with 2 N ammonia in MeOH taking 20 mL fractions to yield the title compound (45 mg, 92%).

$^1$H NMR (400 MHz, CDCl$_3$): δ 8.12 (1H, s), 5.06 (1H, s), 4.89 (1H, br s), 4.20 (2H, m) 3.71 (3H, m), 3.30 (2H, m), 2.42 (3H, s), 1.05 (1H, m), 0.54 (2H, m), 0.24 (2H, m) ppm.

Accurate mass: found 234.1709, $C_{12}H_{20}N_5$ requires 234.1719.

Example 45

(3-Fluoro-benzyl)-[6-(3-methylamino-azetidin-1-yl)-pyrimidin-4-yl]-amine

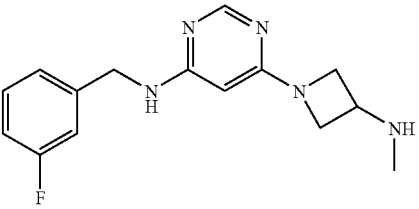

A solution of the title compound of preparation 23 (42 mg, 0.11 mmol) in DCM (5 mL) was treated with 15 trifluoroacetic acid (0.5 mL) and stirred at ambient temperature for 2 hours after which time the reaction mixture was concentrated in vacuo. The residual oil was purified by flash column chromatography on silica gel eluting with DCM:MeOH:0.880 ammonia (1:0:0 changing to 182:15:3, by volume) to yield the title compound as a solid (29 mg, 94%).

$^1$H NMR (400 MHz, CDCl$_3$): δ 8.17 (1H, s), 7.29 (1H, m), 7.09 (1H, d), 7.02 (1H, d), 6.97 (1H, m), 5.07 (1H, d), 5.02 (1H, br s), 4.45 (2H, d), 4.16 (2H, m), 3.69 (3H, m), 2.42 (3H, s) ppm.

MS (APCI) m/z 288 [M+H]⁺

Examples 46 to 59

The following compounds were prepared by a method similar to that described for example 44 and ration 22, by reaction of the compound of preparation 1 with an appropriate amine and subsequent deprotection.

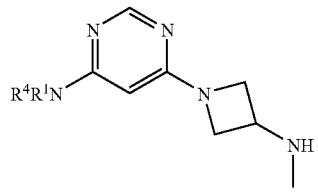

| No. | R⁴R¹N | Name | Yield | LRMS m/z |
| --- | --- | --- | --- | --- |
| 46 | iPrNH | N-Isopropyl-6-[3-(methylamino)azetidin-1-yl]pyrimidin-4-amine | 74% | 222 |
| 47 | 4-F-C₆H₄-CH₂-NH | N-(4-Fluorobenzyl)-6-[3-(methylamino)azetidin-1-yl]pyrimidin-4-amine | 38% | 288 |
| 48 | EtNH | N-Ethyl-6-[3-(methylamino)azetidin-1-yl]pyrimidin-4-amine | 92% | 208 |
| 49 | iBuNH | N-Isobutyl-6-[3-(methylamino)azetidin-1-yl]pyrimidin-4-amine | 12% | 236 |
| 50 | HOCH₂CH₂NH | 2-({6-[3-(Methylamino)azetidin-1-yl]pyrimidin-4-yl}amino)ethanol | 41% | 224 |
| 51 | PhCH₂NH | N-Benzyl-6-[3-(methylamino)azetidin-1-yl]pyrimidin-4-amine | 27% | 270 |
| 52 | 2-Cl-C₆H₄-CH₂-NH | N-(2-Chlorobenzyl)-6-[3-(methylamino)azetidin-1-yl]pyrimidin-4-amine | 42% | 304 |
| 53 | 4-methylpiperidin-1-yl | N-Methyl-1-[6-(4-methylpiperidin-1-yl)pyrimidin-4-yl]azetidin-3-amine | 46% | 262 |
| 54 | MeOCH₂CH₂NH | N-(2-Methoxyethyl)-6-[3-(methylamino)azetidin-1-yl]pyrimidin-4-amine | 77% | 238 |
| 55 | (CH₃)₂CHCH₂CH₂NH | 6-[3-(Methylamino)azetidin-1-yl]-N-(3-methylbutyl)pyrimidin-4-amine | 85% | 250 |
| 56 | piperidin-1-yl | N-Methyl-1-(6-piperidin-1-ylpyrimidin-4-yl)azetidin-3-amine | 45% | 248 |
| 57 | (CH₃)₃CCH₂NH | N-(2,2-Dimethylpropyl)-6-[3-(methylamino)azetidin-1-yl]pyrimidin-4-amine | 84% | 250 |
| 58 | MeNH | N-Methyl-6-[3-(methylamino)azetidin-1-yl]pyrimidin-4-amine | 88% | 195 |
| 59 | (CH₃)₃CCH₂CH₂N | N-(3,3-Dimethylbutyl)-6-[3-(methylamino)azetidin-1-yl]pyrimidin-4-amine | 81% | 264 |

Example 60

N[4]-Isopropyl-6-(3-methylamino-azetidin-1-yl)-pyrimidine-2,4-diamine

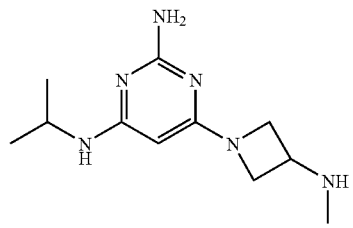

The title compound of preparation 26 (22 mg, 0.07 mmol) was dissolved in trifluoroacetic acid (1 mL) and stirred at ambient temperature for 2 hours after which time the reaction mixture was concentrated in vacuo. The residual gum was purified by flash column chromatography on silica gel eluting with DCM:MeOH:0.880 ammonia (98:2:0.2 changing to 90:10:1, by volume) to yield the title compound as a gum (12mg, 73%).

$^1$H NMR (400 MHz, CD$_3$OD): δ 4.74 (1H, s), 4.1 (2H, dd), 3.82 (1H, m), 3.67 (2H, m), 3.61 (1H, m), 2.33 (3H, s), 1.16 (6H, d) ppm.

MS (APCI) m/z 237 [M+H]$^+$

Example 61

N[4]-(2,2-Dimethylpropyl)-6-[3-(methylamino)azetidin-1-yl]pyrimidine-2,4-diamine

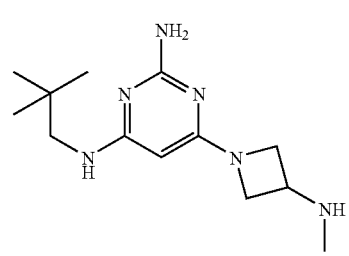

The title compound was prepared by a method similar to that described for example 60, using the compound of preparation 25, in 91% yield.

$^1$H NMR (400 MHz, CD$_3$COCD$_3$): δ 5.29 (1H, br t), 4.97 (2H, br s), 4.79 (1H, s), 3.97 (2H, t), 3.46-3.49 (3H, m), 3.08 (2H, br d), 2.32 (3H, s), 0.93 (9H, s) ppm MS (ESI) m/z 265 [M+H]$^+$

Example 62

6-(3-Methylamino-azetidin-1-yl)-N[4]-(3,3,3-trifluoropropyl)-pyrimidine-2,4-diamine

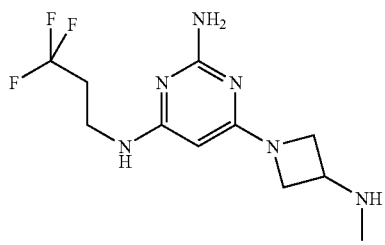

The title compound was prepared by a method similar to that described for example 60, using the compound of preparation 27, in 92% yield.

$^1$H NMR (400 MHz, CD$_3$OD): δ 4.78 (1H, s), 4.11 (2H, m), 3.68 (2H, dd), 3.62 (1H, m), 3.48 (2H, t), 2.42 (2H, m), 2.34 (3H, s) ppm MS (ESI) m/z 291 [M+H]$^+$

Example 63

N[4]-Cyclopropylmethyl-6-(3-methylamino-azetidin-1-yl)-pyrimidine-2,4-diamine

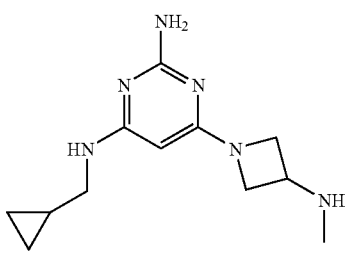

The title compound was prepared by a method similar to that described for example 60, using the compound of preparation 28, in 85% yield.

$^1$H NMR (400 MHz, CD$_3$OD): δ 4.17 (2H, m), 3.76 (2H, m), 3.70 (1H, m), 3.06 (2H, d), 2.39 (3H, s), 1.01 (1H, m), 0.52 (2H, m), 0.22 (2H, m) ppm.

MS (APCI) m/z 249 [M+H]$^+$

Example 64

N⁴-(3,3-Dimethyl-butyl)-6-(3-methylamino-azetidin-1-yl)-pyrimidine-2,4-diamine

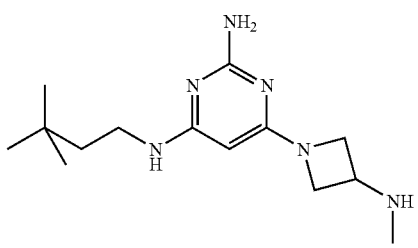

The title compound was prepared by a method similar to that described for example 60, using the compound of preparation 29, in 87% yield.

¹H NMR (400 MHz, CD₃OD): δ 4.73 (1H, s) 4.11 (2H, m), 3.68 (2H, m), 3.62 (1H, m), 3.18 (2H, m), 2.33 (3H, s), 1.48 (2H, m), 0.96 (9H, s) ppm.
MS (APCI) m/z 279 [M+H]⁺

Example 65

N⁴-(3-Fluoro-benzyl)-6-(3-methylamino-azetidin-1-yl)-pyrimidine-2,4-diamine

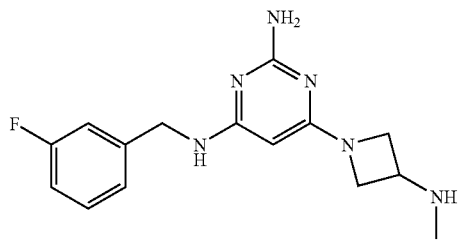

The title compound was prepared by a method similar to that described for example 60, using the compound of preparation 30, in 84% yield.

¹H NMR (400 MHz, CD₃COCD₃): δ 7.32 (1H, m), 7.16 (1H, d), 7.10 (1H, br d), 6.96 (1H, m), 6.01 (1H, m), 5.06 (2H, br s), 4.79 (1H, s), 4.51 (2H, d), 3.96 (2H, t), 3.57-3.48 (3H, m), 2.31 (3H, s) ppm.
MS (APCI) m/z 303 [M+H]⁺

Example 66

N⁴-(3-Methoxy-benzyl)-6-(3-methylamino-azetidin-1-yl)-pyrimidine-2,4-diamine

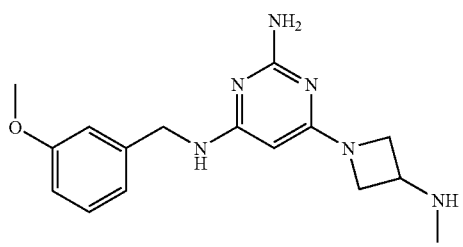

The title compound was prepared by a method similar to that described for example 60, using the compound of preparation 31, in 72% yield.

¹H NMR (400 MHz, CD₃OD): δ 7.20 (1H, t), 6.89-6.85 (2H, m), 6.78 (1H, dd), 4.73 (2H, s), 4.37 (2H, s), 4.07 (2H, t), 3.76 (3H, s), 3.65-3.55 (3H, m), 2.31 (3H, s) ppm.

MS (APCI) m/z 315 [M+H]⁺

Example 67

N⁴-Cyclobutylmethyl-6-(3-methylamino-azetidin-1-yl)-pyrimidine-2,4-diamine

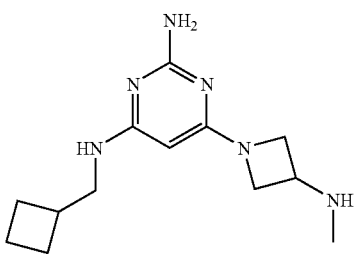

The title compound was prepared by a method similar to that described for example 60, using the compound of preparation 32, in 86% yield.

¹H NMR (400 MHz, CD₃COCD₃): δ 5.31 (1H, m), 4.99 (2H, br s), 4.73 (1H, s), 3.96 (2H, t), 3.58-3.50 (3H, m), 3.23 (2H, t), 2.55 (1H, m), 2.32 (3H, s), 2.05-1.97 (H, m), 1.90-1.82 (2H, m), 1.77-1.68 (2H, m) ppm.

MS (APCI) m/z 263 [M+H]⁺

Example 68

N⁴-Cyclopentylmethyl-6-(3-methylamino-azetidin-1-yl)-pyrimidine-2,4-diamine

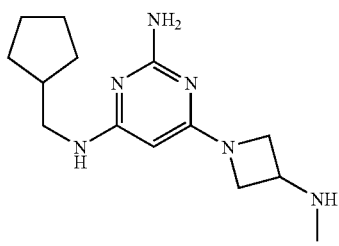

The title compound was prepared by a method similar to that described for example 60, using the compound of preparation 33, in 81% yield.

$^1$H NMR (400 MHz, CD$_3$OD): δ 4.75 (1H, s), 4.11 (2H, dd), 3.68 (2H, dd), 3.61 (1H, m), 3.09 (2H, d), 2.33 (3H, s), 2.13 (1H, m), 1.83-1.75 (2H, m), 1.70-1.53 (4H, m), 1.29-1.21 (2H, m) ppm.

MS (APCI) m/z 277 [M+H]$^+$

Examples 69 to 90

The following compounds were prepared by a method similar to that described for example 60 and preparation 26 by reaction of the compound of preparation 12 with an appropriate amine and subsequent deprotection.

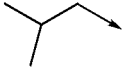

| No | R$^1$ | Name | Yield | LRMS m/z |
|---|---|---|---|---|
| 69 | Me | N$^4$-Methyl-6-[3-(methylamino)azetidin-1-yl]pyrimidine-2,4-diamine | 78% | 209 |
| 70 | Et | N$^4$-Ethyl-6-[3-(methylamino)azetidin-1-yl]pyrimidine-2,4-diamine | 83% | 223 |
| 71 |  | N$^4$-Isobutyl-6-[3-(methylamino)azetidin-1-yl]pyrimidine-2,4-diamine | 87% | 251 |
| 72 | 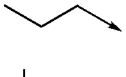 | N$^4$-Cyclopropyl-6-[3-(methylamino)azetidin-1-yl]pyrimidine-2,4-diamine | 74% | 235 |
| 73 | 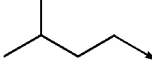 | 6-[3-(Methylamino)azetidin-1-yl]-N$^4$-propylpyrimidine-2,4-diamine | 85% | 237 |
| 74 |  | 6-[3-(Methylamino)azetidin-1-yl]-N$^4$-(3-methylbutyl)pyrimidine-2,4-diamine | 81% | 265 |
| 75 | 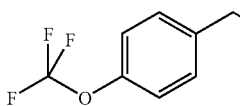 | N$^4$-Cyclobutyl-6-[3-(methylamino)azetidin-1-yl]pyrimidine-2,4-diamine | 72% | 249 |
| 76 | 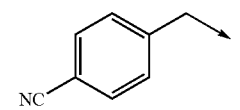 | 6-[3-(Methylamino)azetidin-1-yl]-N$^4$-[4-(trifluoromethoxy)benzyl]pyrimidine-2,4-diamine | 76% | 369 |
| 77 | 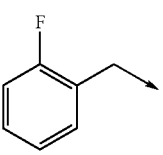 | 4-[({2-Amino-6-[3-(methylamino)azetidin-1-yl]pyrimidin-4-yl}amino)methyl]benzonitrile | 79% | 310 |
| 78 | 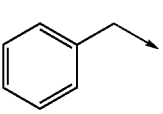 | N$^4$-(2-Fluorobenzyl)-6-[3-(methylamino)azetidin-1-yl]pyrimidine-2,4-diamine | 77% | 303 |
| 79 |  | N$^4$-Benzyl-6-[3-(methylamino)azetidin-1-yl]pyrimidine-2,4-diamine | 65% | 285 |

-continued

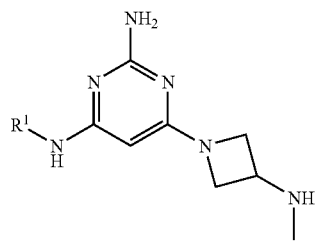

| No | R¹ | Name | Yield | LRMS m/z |
|---|---|---|---|---|
| 80 | 3-(trifluoromethyl)benzyl | 6-[3-(Methylamino)azetidin-1-yl]-$N^4$-[3-(trifluoromethyl)benzyl]pyrimidine-2,4-diamine | 81% | 353 |
| 81 | 4-chlorobenzyl | $N^4$-(4-Chlorobenzyl)-6-[3-(methylamino)azetidin-1-yl]pyrimidine-2,4-diamine | 73% | 319 |
| 82 | 2-methylbenzyl | 6-[3-(Methylamino)azetidin-1-yl]-$N^4$-(2-methylbenzyl)pyrimidine-2,4-diamine | 68% | 299 |
| 83 | 3-methylbenzyl | 6-[3-(Methylamino)azetidin-1-yl]-$N^4$-(3-methylbenzyl)pyrimidine-2,4-diamine | 79% | 299 |
| 84 | 2-(trifluoromethyl)benzyl | 6-[3-(Methylamino)azetidin-1-yl]-$N^4$-[2-(trifluoromethyl)benzyl]pyrimidine-2,4-diamine | 74% | 353 |
| 85 | 4-(trifluoromethyl)benzyl | 6-[3-(Methylamino)azetidin-1-yl]-$N^4$-[4-(trifluoromethyl)benzyl]pyrimidine-2,4-diamine | 77% | 353 |
| 86 | 3-chlorobenzyl | $N^4$-(3-Chlorobenzyl)-6-[3-(methylamino)azetidin-1-yl]pyrimidine-2,4-diamine | 71% | 319 |
| 87 | 2-methoxybenzyl | $N^4$-(2-Methoxybenzyl)-6-[3-(methylamino)azetidin-1-yl]pyrimidine-2,4-diamine | 68% | 315 |
| 88 | 4-methylbenzyl | 6-[3-(Methylamino)azetidin-1-yl]-$N^4$-(4-methylbenzyl)pyrimidine-2,4-diamine | 70% | 299 |

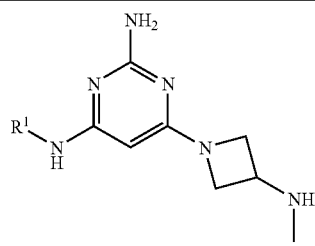

| No | R¹ | Name | Yield | LRMS m/z |
|---|---|---|---|---|
| 89 | 2-Cl-benzyl | N⁴-(2-Chlorobenzyl)-6-[3-(methylamino)azetidin-1-yl]pyrimidine-2,4-diamine | 72% | 319 |
| 90 | 4-F-benzyl | N⁴-(4-Fluorobenzyl)-6-[3-(methylamino)azetidin-1-yl]pyrimidine-2,4-diamine | 83% | 303 |

Example 91

N⁴-(3-Fluorobenzyl)-6-(4-methylpiperazin-1-yl)pyrimidine-2,4-diamine

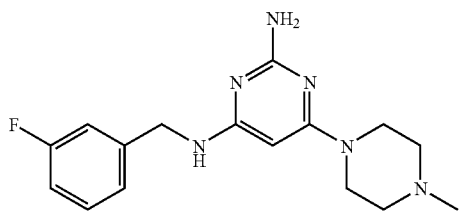

The title compound of preparation 18 (20 mg, 0.08 mmol) was treated with DMSO (150 μL) and N-methylpiperazine (88 μL, 0.79 mmol) and heated to 120° C. in a sealed vessel for 16 hours. The reaction mixture was cooled to ambient temperature, partitioned between water (2 mL) and ethyl acetate (2 mL) filtered through diatomaceous earth, washing with further ethyl acetate (15 mL). The organic fraction of the filtrate was concentrated in vacuo and purified by flash column chromatography on silica gel eluting with DCM:MeOH:0.880 ammonia (90:10:1 changing to 90:10:1, by volume) to yield the title compound as a gum (20 mg, 79%).

$^1$H NMR (400 MHz, CD$_3$OD): δ 7.34-7.27 (1H, m), 7.14-7.10 (1H, m), 7.08-7.01 (1H, m), 6.98-6.89 (1H, m), 5.11 (1H, s), 4.45 (2H, s), 3.51-3.42 (4H, m), 2.48-2.41 (4H, m), (2.30 (3H, s) ppm.

MS (APCI) m/z 208 [M-C$_7$H$_6$F$_1$+2H]$^+$

Examples 92 to 98

The following compounds were prepared by a method similar to that described for example 91 using the appropriate pyrimidine starting material and the appropriate amine starting material.

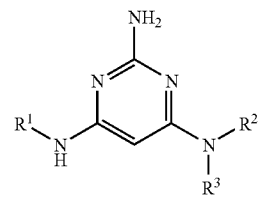

| No. | R¹NH | NR²R³ | Name | Yield | Preparation No. of Starting material | LRMS m/z |
|---|---|---|---|---|---|---|
| 92 | 3-F-benzyl-NH₂ | (3aR*,6aS*)-5-methylhexahydropyrrolo[3,4-c]pyrrol-2(1H)-yl | N⁴-(3-Fluorobenzyl)-6-[(3aR*,6aS*)-5-methylhexahydropyrrolo[3,4-c]pyrrol-2(1H)-yl]pyrimidine-2,4-diamine | 73% | 18 | 343 |

-continued

Common structure: 2-amino-4,6-bis(amino)pyrimidine with R¹NH- and -NR²R³ substituents.

| No. | R¹NH | NR²R³ | Name | Yield | Preparation No. of Starting material | LRMS m/z |
|---|---|---|---|---|---|---|
| 93 | 3,3-dimethylbutyl-NH | (3R)-3-methylpiperazin-1-yl | N⁴-(3,3-Dimethylbutyl)-6-[(3R)-3-methylpiperazin-1-yl]pyrimidine-2,4-diamine | 92% | 16 | 293 |
| 94 | 3,3-dimethylbutyl-NH | (3S)-3-methylpiperazin-1-yl | N⁴-(3,3-Dimethylbutyl)-6-[(3S)-3-methylpiperazin-1-yl]pyrimidine-2,4-diamine | 89% | 16 | 293 |
| 95 | 2,2-dimethylpropyl-NH | (3R)-3-methylpiperazin-1-yl | N⁴-(2,2-Dimethylpropyl)-6-[(3R)-3-methylpiperazin-1-yl]pyrimidine-2,4-diamine | 85% | 19 | 279 |
| 96 | 2,2-dimethylpropyl-NH | (3S)-3-methylpiperazin-1-yl | N⁴-(2,2-Dimethylpropyl)-6-[(3S)-3-methylpiperazin-1-yl]pyrimidine-2,4-diamine | 77% | 19 | 279 |
| 97 | EtNH | (3R)-3-methylpiperazin-1-yl | N⁴-Ethyl-6-[(3R)-3-methylpiperazin-1-yl]pyrimidine-2,4-diamine | 85% | 17 | 237 |
| 98 | EtNH | (3S)-3-methylpiperazin-1-yl | N⁴-Ethyl-6-[(3S)-3-methylpiperazin-1-yl]pyrimidine-2,4-diamine | 73% | 17 | 237 |

Examples 99 to 127

The following compounds were prepared by similar method to those used to prepare the compounds above.

| No. | Structure | Name | LRMS m/z |
|---|---|---|---|
| 99 | 6-(4-methylpiperazin-1-yl)-N-(2,2-dimethylpropyl)pyrimidin-4-amine | N-(2,2-Dimethylpropyl)-6-(4-methylpiperazin-1-yl)pyrimidin-4-amine | 264 |

-continued

| No. | Name | LRMS m/z |
|---|---|---|
| 100 | N-(3-Methylbutyl)-6-(4-methylpiperazin-1-yl)pyrimidin-4-amine | 264 |
| 101 | $N^4$-(3,3-Dimethylbutyl)-$N^6$-[(3S)-pyrrolidin-3-yl]pyrimidine-2,4,6-triamine | 279 |
| 102 | $N^4$-(3,3-Dimethylbutyl)-6-(4-methylpiperazin-1-yl)pyrimidine-2,4-diamine | 293 |
| 103 | N-Ethyl-6-(4-methylpiperazin-1-yl)pyrimidin-4-amine | 222 |
| 104 | N-Isopropyl-6-(4-methylpiperazin-1-yl)pyrimidin-4-amine | 236 |
| 105 | N-Isobutyl-6-(4-methylpiperazin-1-yl)pyrimidin-4-amine | 250 |
| 106 | N-(Cyclopropylmethyl)-6-(4-methylpiperazin-1-yl)pyrimidin-4-amine | 248 |

-continued

| No. | Structure | Name | LRMS m/z |
|---|---|---|---|
| 107 | 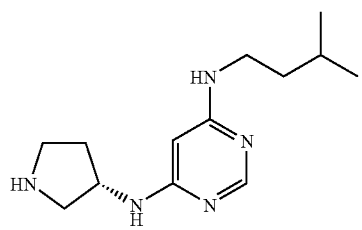 | N-(3-Methylbutyl)-N-[(3S)-pyrrolidin-3-yl]pyrimidine-4,6-diamine | 250 |
| 108 | 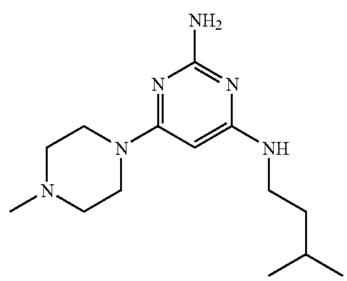 | N$^4$-(3-Methylbutyl)-6-(4-methylpiperazin-1-yl)pyrimidine-2,4-diamine | 279 |
| 109 | 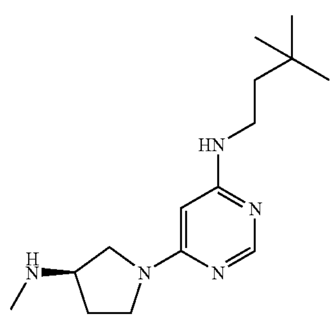 | N-(3,3-Dimethylbutyl)-6-[(3R)-3-(methylamino)pyrrolidin-1-yl]pyrimidin-4-amine | 278 |
| 110 | 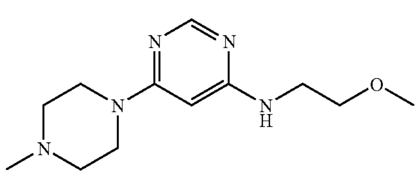 | N-(2-Methoxyethyl)-6-(4-methylpiperazin-1-yl)pyrimidin-4-amine | 252 |
| 111 | 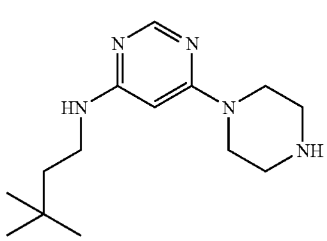 | N-(3,3-Dimethylbutyl)-6-piperazin-1-ylpyrimidin-4-amine | 264 |
| 112 | 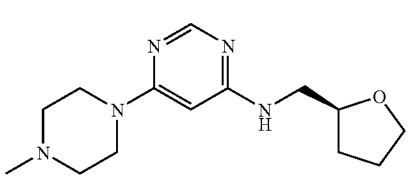 | 6-(4-Methylpiperazin-1-yl)-N-[(2S)-tetrahydrofuran-2-ylmethyl]pyrimidin-4-amine | 278 |

-continued

| No. | Structure | Name | LRMS m/z |
|---|---|---|---|
| 113 | 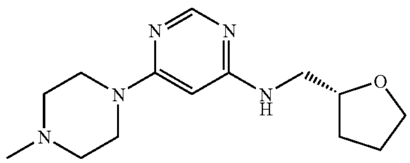 | 6-(4-Methylpiperazin-1-yl)-N-[(2R)-tetrahydrofuran-2-ylmethyl]pyrimidin-4-amine | 278 |
| 114 | 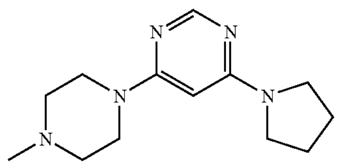 | 4-(4-Methylpiperazin-1-yl)-6-pyrrolidin-1-ylpyrimidine | 248 |
| 115 | 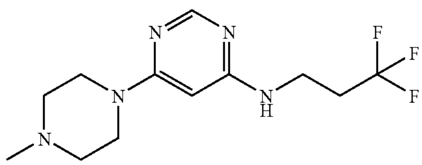 | 6-(4-Methylpiperazin-1-yl)-N-(3,3,3-trifluoropropyl)pyrimidin-4-amine | 290 |
| 116 | 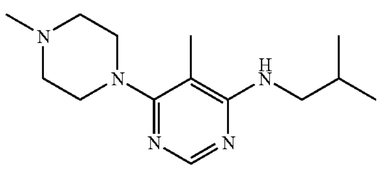 | N-Isobutyl-5-methyl-6-(4-methylpiperazin-1-yl)pyrimidin-4-amine | 263 |
| 117 | 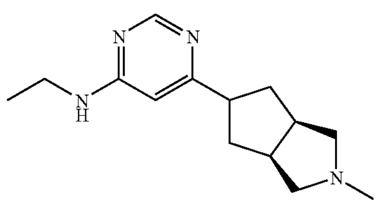 | N-Ethyl-6-[(3aR*,6aS*)-5-methylhexahydropyrrolo[3,4-c]pyrrol-2(1H)-yl]pyrimidin-4-amine | 248 |
| 118 | 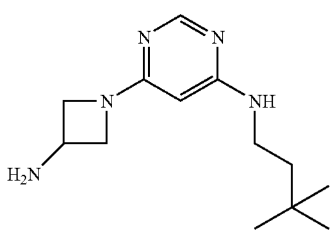 | 6-(3-Aminoazetidin-1-yl)-N-(3,3-dimethylbutyl)pyrimidin-4-amine | 250 |
| 119 | 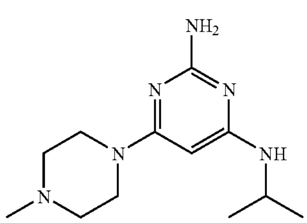 | $N^4$-Isopropyl-6-(4-methylpiperazin-1-yl)pyrimidine-2,4-diamine | 251 |
| 120 | 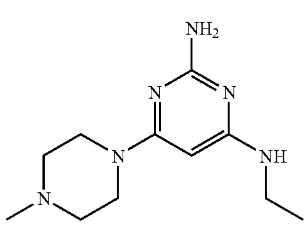 | $N^4$-Ethyl-6-(4-methylpiperazin-1-yl)pyrimidine-2,4-diamine | 237 |

| No. | Structure | Name | LRMS m/z |
|---|---|---|---|
| 121 | 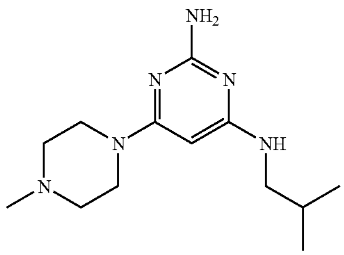 | $N^4$-Isobutyl-6-(4-methylpiperazin-1-yl)pyrimidine-2,4-diamine | 265 |
| 122 | 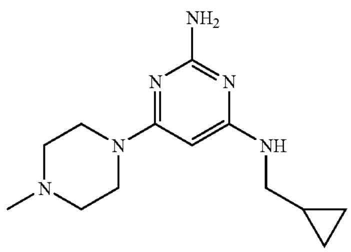 | $N^4$-(Cyclopropylmethyl)-6-(4-methylpiperazin-1-yl)pyrimidine-2,4-diamine | 263 |
| 123 | 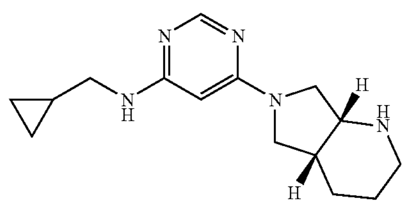 | N-(Cyclopropylmethyl)-6-[(4aR*,7aR*)-octahydro-6H-pyrrolo[3,4-b]pyridin-6-yl]pyrimidin-4-amine | 274 |
| 124 | 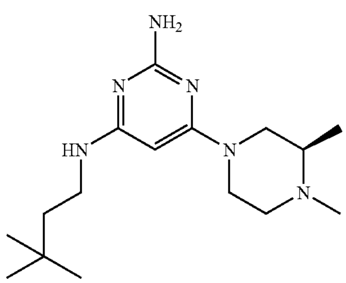 | $N^4$-(3,3-Dimethylbutyl)-6-[(3R)-3,4-dimethylpiperazin-1-yl]pyrimidine-2,4-diamine | 307 |
| 125 | 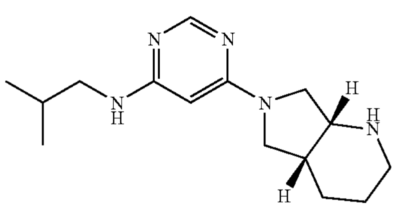 | N-Isobutyl-6-[(4aR*,7aR*)-octahydro-6H-pyrrolo[3,4-b]pyridin-6-yl]pyrimidin-4-amine | 276 |
| 126 | 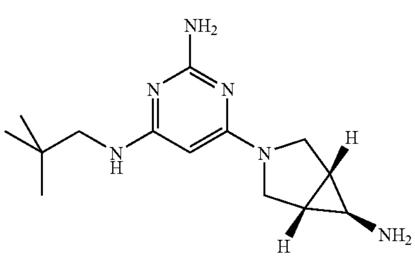 | 6-[(1R*,5S*,6s*)-6-Amino-3-azabicyclo[3.1.0]hex-3-yl]-$N^4$-(2,2-dimethylpropyl)pyrimidine-2,4-diamine | 277 |

| No. | Structure | Name | LRMS m/z |
|---|---|---|---|
| 127 | 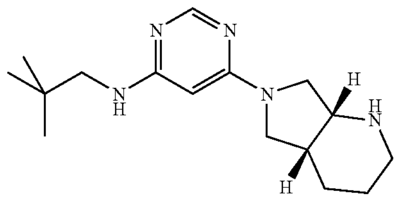 | N-(2,2-Dimethylpropyl)-6-[(4aR*,7aR*)-octahydro-6H-pyrrolo[3,4-b]pyridin-6-yl]pyrimidin-4-amine | 290 |

Examples 128 to 132

The following compounds were prepared by a method similar to that described for example 60 and preparation 26 by reaction of the compound of preparation 12 with an appropriate amine and subsequent deprotection.

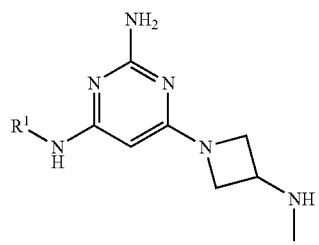

| No. | R¹ | Name | LRMS m/z |
|---|---|---|---|
| 128 | | 6-[3-(Methylamino)azetidin-1-yl]-N⁴-(2-methylbutyl)pyrimidine-2,4-diamine | 265 |
| 129 | | N⁴-[(1S)-1,2-Dimethylpropyl]-6-[3-(methylamino)azetidin-1-yl]pyrimidine-2,4-diamine | 265 |
| 130 | | N⁴-(2,5-Difluorobenzyl)-6-[3-(methylamino)azetidin-1-yl]pyrimidine-2,4-diamine | 321 |
| 131 | | N⁴-(2,3-Difluorobenzyl)-6-[3-(methylamino)azetidin-1-yl]pyrimidine-2,4-diamine | 321 |
| 132 | | N⁴-Butyl-6-[3-(methylamino)azetidin-1-yl]pyrimidine-2,4-diamine | 251 |

Examples 133 to 153

The following compounds were prepared by a method similar to that described for preparation 26 (solvent and temperature indicated in the table for a period between 10 and 72 hours) using the appropriate pyrimidine starting material and the appropriate amine. Deprotection (if necessary) was carried out using conditions described for example 60.

| No. | Structure | Name | Cond. | Prep. | Depr. | LRMS m/z |
|---|---|---|---|---|---|---|
| 133 | 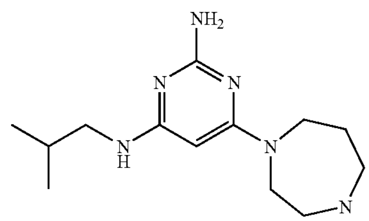 | 6-(1,4-Diazepan-1-yl)-N$^4$-isobutylpyrimidine-2,4-diamine | Neat/ 120° C. | 34 | Y | 265 |
| 134 | 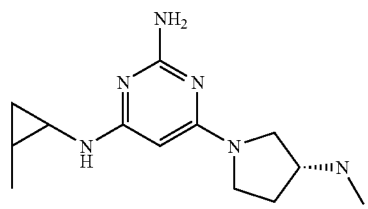 | 6-[(3R)-3-(Methylamino)pyrrolidin-1-yl]-N$^4$-(2-methylcyclopropyl)pyrimidine-2,4-diamine | DMSO/ 130° C. | 35 | Y | 263 |
| 135 | 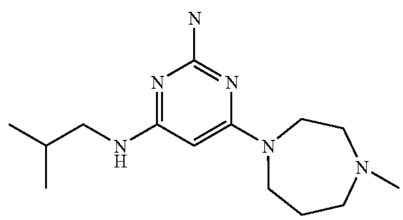 | N$^4$-Isobutyl-6-(4-methyl-1,4-diazepan-1-yl)pyrimidine-2,4-diamine | Neat/ 120° C. | 36 | N | 279 |
| 136 | 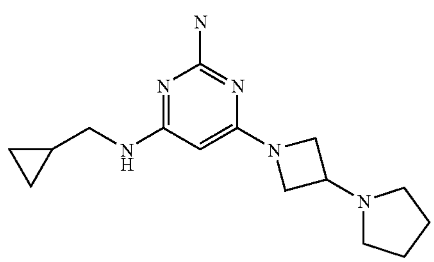 | N$^4$-(Cyclopropylmethyl)-6-(3-pyrrolidin-1-ylazetidin-1-yl)pyrimidine-2,4-diamine | NMP/ 150° C. | 37 | N | 289 |
| 137 | 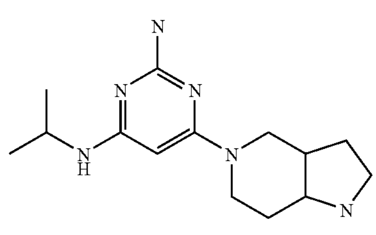 | N$^4$-Isopropyl-6-[(3aR*,7aS*)-octahydro-5H-pyrrolo[3,2-c]pyridin-5-yl]pyrimidine-2,4-diamine | DMSO/ 120° C. | 38 | Y | 277 |
| 138 | 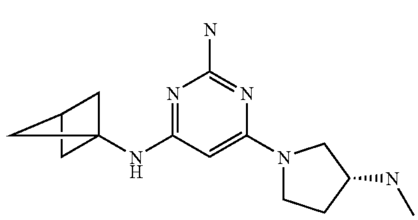 | N$^4$-Bicyclo[1.1.1]pent-1-yl-6-[(3R)-3-(methylamino)pyrrolidin-1-yl]pyrimidine-2,4-diamine | DMSO/ 120° C. | 39 | Y | 275 |

-continued

| No. | Structure | Name | Cond. | Prep. | Depr. | LRMS m/z |
|---|---|---|---|---|---|---|
| 139 | 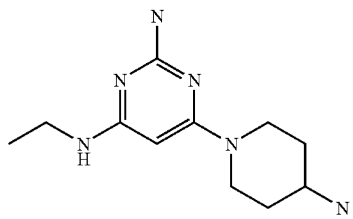 | 6-(4-Aminopiperidin-1-yl)-N$^4$-ethylpyrimidine-2,4-diamine | Neat/ 120° C. | 40 | Y | 237 |
| 140 | 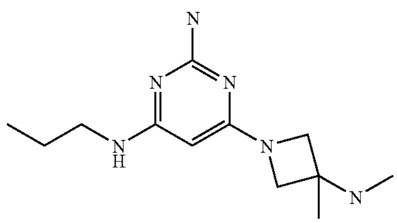 | 6-[3-Methyl-3-(methylamino)azetidin-1-yl]-N$^4$-propylpyrimidine-2,4-diamine | DMSO/ 120° C. | 41 | Y | 251 |
| 141 | 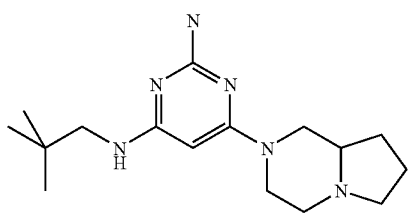 | N$^4$-(2,2-Dimethylpropyl)-6-(hexahydropyrrolo[1,2-a]pyrazin-2(1H)-yl)pyrimidine-2,4-diamine | NMP/ 145° C. | 42 | N | 305 |
| 142 | 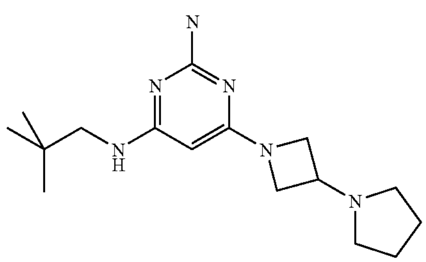 | N$^4$-(2,2-Dimethylpropyl)-6-(3-pyrrolidin-1-ylazetidin-1-yl)pyrimidine-2,4-diamine | NMP/ 150° C. | 19 | N | 305 |
| 143 | 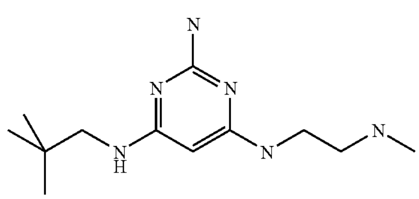 | N$^4$-(2,2-Dimethylpropyl)-N$^6$-[2-(methylamino)ethyl]pyrimidine-2,4,6-triamine | Neat/ 120° C. | 19 | Y | 253 |
| 144 | 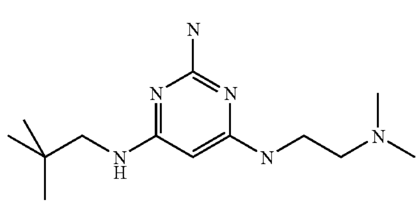 | N$^4$-[2-(Dimethylamino)ethyl]-N$^6$-(2,2-dimethylpropyl)pyrimidine-2,4,6-triamine | Neat/ 120° C. | 19 | N | 267 |
| 145 | 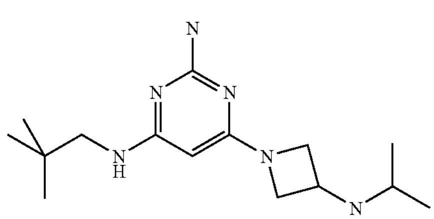 | N$^4$-(2,2-Dimethylpropyl)-6-[3-(isopropylamino)azetidin-1-yl]pyrimidine-2,4-diamine | NMP/ 150° C. | 19 | Y | 293 |

-continued

| No. | Structure | Name | Cond. | Prep. | Depr. | LRMS m/z |
|---|---|---|---|---|---|---|
| 146 | 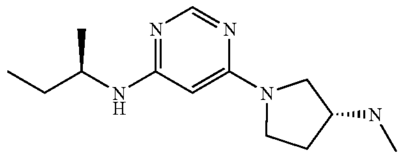 | 6-[(3R)-3-(Methylamino)pyrrolidin-1-yl]-N-[(1R)-1-methylpropyl]pyrimidin-4-amine | Neat/ 120° C. | 10 | Y | 250 |
| 147 | 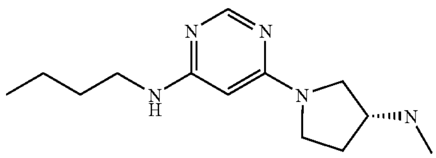 | N-Butyl-6-[(3R)-3-(methylamino)pyrrolidin-1-yl]pyrimidin-4-amine | Neat/ 120° C. | 10 | Y | 250 |
| 148 | 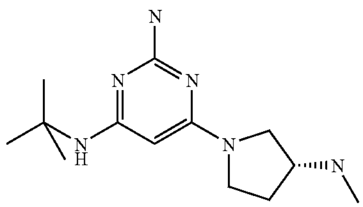 | $N^4$-(tert-Butyl)-6-[(3R)-3-(methylamino)pyrrolidin-1-yl]pyrimidine-2,4-diamine | NMP/ 160° C. | 43 | Y | 265 |
| 149 | 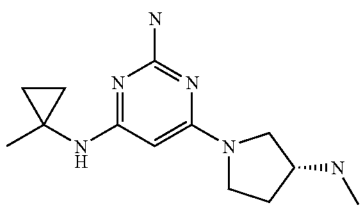 | 6-[(3R)-3-(Methylamino)pyrrolidin-1-yl]-$N^4$-(1-methylcyclopropyl)pyrimidine-2,4-diamine | DMSO/ 130° C. | 44 | Y | 263 |
| 150 | 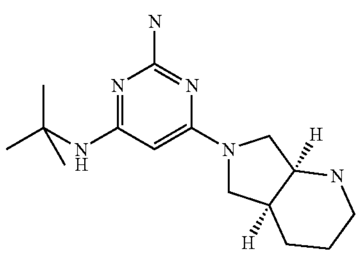 | $N^4$-(tert-Butyl)-6-[(4aS*,7aS*)-octahydro-6H-pyrrolo[3,4-b]pyridin-6-yl]pyrimidine-2,4-diamine | NMP/ 170° C. | 43 | Y | 291 |
| 151 | 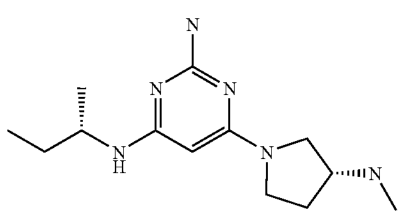 | 6-[(3R)-3-(Methylamino)pyrrolidin-1-yl]-$N^4$-[(1S)-1-methylpropyl]pyrimidine-2,4-diamine | DMSO/ 120° C. | 15 | Y | 265 |
| 152 | 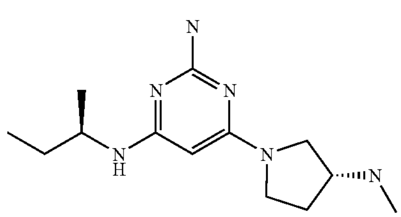 | 6-[(3R)-3-(Methylamino)pyrrolidin-1-yl]-$N^4$-[(1R)-1-methylpropyl]pyrimidine-2,4-diamine | DMSO/ 120° C. | 15 | Y | 265 |

| No. | Structure | Name | Cond. | Prep. | Depr. | LRMS m/z |
|---|---|---|---|---|---|---|
| 153 | 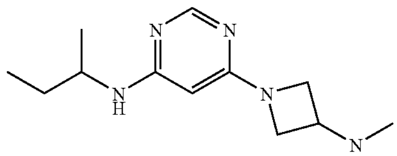 | N-(sec-Butyl)-6-[3-(methylamino)azetidin-1-yl]pyrimidin-4-amine | Neat/ 120° C. | 1 | Y | 235 |

The following compounds were prepared by similar method to those used to prepare the compounds above, using the appropriate pyrimidine starting material and the appropriate amine:

Example Name

154 $N^4$-(Cyclopropylmethyl)-6-piperazin-1-ylpyrimidine-2,4-diamine
155 $N^4$-(4-Fluorobenzyl)-6-[(3R)-3-(methylamino)pyrrolidin-1-yl]pyrimidine-2,4-diamine
156 $N^4$-(2,2-Dimethylpropyl)-6-piperazin-1-ylpyrimidine-2,4-diamine
157 $N^4$-(2,4-Difluorobenzyl)-6-[3-(methylamino)azetidin-1-yl]pyrimidine-2,4-diamine
158 6-[3-(Methylamino)azetidin-1-yl]-$N^4$-(1-methylbutyl)pyrimidine-2,4-diamine
159 $N^4$-(2,2-Dimethylpropyl)-6-[3-(methylamino)azetidin-1-yl]pyrimidine-2,4-diamine hydrochloride
160 $N^4$-[(1R)-1,2-Dimethylpropyl]-6-[3-(methylamino)azetidin-1-yl]pyrimidine-2,4-diamine
161 6-[3-(Methylamino)azetidin-1-yl]-$N^4$-[(1S)-1-methylpropyl]pyrimidine-2,4-diamine
162 $N^4$-(2,2-Dimethylpropyl)-6-[(3aR*,7aS*)-octahydro-5H-pyrrolo[3,2-c]pyridin-5-yl]pyrimidine-2,4-diamine
163 6-Piperazin-1-yl-$N^4$-propylpyrimidine-2,4-diamine
164 $N^4$-Ethyl-6-[3-(methylamino)azetidin-1-yl]pyrimidine-2,4-diamine
165 $N^4$-(Cyclopropylmethyl)-6-[(4aR,7aR)-octahydro-6H-pyrrolo[3,4-b]pyridin-6-yl]pyrimidine-2,4-diamine
166 $N^4$-(2,2-Dimethylpropyl)-6-[(4aS,7aS)-octahydro-6H-pyrrolo[3,4-b]pyridin-6-yl]pyrimidine-2,4-diamine
167 $N^4$-(Cyclopropylmethyl)-6-[(3R)-3-(methylamino)pyrrolidin-1-yl]pyrimidine-2,4-diamine
168 $N^4$-(tert-Butyl)-6-[3-(methylamino)azetidin-1-yl]pyrimidine-2,4-diamine
169 $N^4$-Isopropyl-6-[(4aS,7aS)-octahydro-6H-pyrrolo[3,4-b]pyridin-6-yl]pyrimidine-2,4-diamine
170 6-(3-Aminoazetidin-1-yl)-$N^4$-ethylpyrimidine-2,4-diamine
171 6-(3-Aminoazetidin-1-yl)-$N^4$-(cyclopropylmethyl)pyrimidine-2,4-diamine
172 $N^4$-Cycopropyl-6-[(3aR*,7aS*)-octahydro-5H-pyrrolo[3,2-c]pyridin-5-yl]pyrimidine-2,4-diamine
173 4-[3-(Methylamino)azetidin-1-yl]-6-(4-methylpiperidin-1-yl)pyrimidin-2-amine
174 $N^4$-(Cyclopentylmethyl)-6-[(3R)-3-(methylamino)pyrrolidin-1-yl]pyrimidine-2,4-diamine
175 6-(1,4-Diazepan-1-yl)-$N^4$-ethylpyrimidine-2,4-diamine
176 $N^4$-(Cyclopropylmethyl)-N6-[2-(dimethylamino)ethyl]pyrimidine-2,4,6-triamine
177 $N^4$-(2,2-Dimethylpropyl)-6-[(3S)-3-(methylamino)pyrrolidin-1-yl]pyrimidine-2,4-diamine
178 $N^4$-Cyclobutyl-6-[(4aS,7aS)-octahydro-6H-pyrrolo[3,4-b]pyridin-6-yl]pyrimidine-2,4-diamine
179 N-Cyclobutyl-6-[3-(methylamino)azetidin-1-yl]pyrimidin-4-amine
180 6-[(3R)-3-(Methylamino)pyrrolidin-1-yl]-$N^4$-propylpyrimidine-2,4-diamine
181 N-Cyclobutyl-6-[(3R)-3-(methylamino)pyrrolidin-1-yl]pyrimidin-4-amine
182 $N^4$-(2-Methoxyethyl)-6-[3-(methylamino)azetidin-1-yl]pyrimidine-2,4-diamine
183 N-(2,2-Dimethylpropyl)-6-[(3R)-3-(methylamino)pyrrolidin-1-yl]pyrimidin-4-amine
184 $N^4$-(Cyclopropylmethyl)-6-[(3S)-3-methylpiperazin-1-yl]pyrimidine-2,4-diamine
185 $N^4$-Ethyl-6-(4-methyl-1,4-diazepan-1-yl)pyrimidine-2,4-diamine
186 $N^4$-(2,2-Dimethylpropyl)-6-[3-methyl-3-(methylamino)azetidin-1-yl]pyrimidine-2,4-diamine
187 $N^4$-Isopropyl-6-piperazin-1-ylpyrimidine-2,4-diamine
188 $N^4$-(Cyclopropylmethyl)-6-[(3aR*,7aS*)-octahydro-5H-pyrrolo[3,2-c]pyridin-5-yl]pyrimidine-2,4-diamine
189 N-Cyclopropyl-6-[3-(methylamino)azetidin-1-yl]pyrimidin-4-amine
190 6-(3-Aminoazetidin-1-yl)-$N^4$-(2,2-dimethylpropyl)pyrimidine-2,4-diamine
191 $N^4$-(2,2-Dimethylpropyl)-6-[(1S,4S)-5-methyl-2,5-diazabicyclo[2.2.1]hept-2-yl]pyrimidine-2,4-diamine
192 N-(2,2-Dimethylpropyl)-6-(3-pyrrolidin-1-ylazetidin-1-yl)pyrimidin-4-amine
193 $N^4$-Ethyl-6-[(3aR*,7aS*)-octahydro-5H-pyrrolo[3,2-c]pyridin-5-yl]pyrimidine-2,4-diamine
194 N-(Cyclopropylmethyl)-N'-[2-(dimethylamino)ethyl]pyrimidine4,6-diamine
195 6-[(3R)-3-Aminopyrrolidin-1-yl]-$N^4$-(2-methylbutyl)pyrimidine-2,4-diamine
196 $N^4$-(Cyclopropylmethyl)-6-[3-methyl-3-(methylamino)azetidin-1-yl]pyrimidine-2,4-diamine
197 $N^4$-Ethyl-6-(3-pyrrolidin-1-ylazetidin-1-yl)pyrimidine-2,4-diamine
198 $N^4$-isoPropyl-6-(4-methyl-1,4-diazepan-1-yl)pyrimidine-2,4-diamine
199 $N^4$-Cyclobutyl-6-[(3R)-3-(methylamino)pyrrolidin-1-yl]pyrimidine-2,4-diamine
200 $N^4$Methyl-6-[(3aR*,7aS*)-octahydro-5H-pyrrolo[3,2-c]pyridin-5-yl]pyrimidine-2,4-diamine
201 6-(4-Aminopiperidin-1-yl)-$N^4$-(2,2-dimethylpropyl)pyrimidine-2,4-diamine
202 N-Isopropyl-6-[(3R)-3-(methylamino)pyrrolidin-1-yl]pyrimidin-4-amine
203 N-Cyclopropyl-6-[(3R)-3-(methylamino)pyrrolidin-1-yl]pyrimidin-4-amine
204 $N^4$-(Cyclopropylmethyl)-6-[(3S)-3-(methylamino)pyrrolidin-1-yl]pyrimidine-2,4-diamine 205 $N^4$-Ethyl-6-[(3S)-3-(methylamino)pyrrolidin-1-yl]pyrimidine-2,4-diamine
206 6-[3-(Methylamino)azetidin-1-yl]-N-propylpyrimidin-4-amine
207 $N^4$-(tert-Butyl)-6-[(3S)-3-(methylamino)pyrrolidin-1-yl]pyrimidine-2,4-diamine
208 $N^4$-Methyl-6-piperazin-1-ylpyrimidine-2,4-diamine
209 $N^4$-(2,2-Dimethylpropyl)-6-{3-[(methylamino)methyl]azetidin-1-yl}pyrimidine-2,4-diamine
210 $N^4$-(Cyclopropylmethyl)-6-[(4aS,7aS)-octahydro-6H-pyrrolo[3,4-b]pyridin-6-yl]pyrimidine-2,4-diamine
211 $N^4$-(3,3-Dimethylbutyl)-6-[(3S)-3-(methylamino)pyrrolidin-1-yl]pyrimidine-2,4-diamine
212 $N^4$-(2-Aminoethyl)-$N^6$-(cyclopropylmethyl)pyrimidine-2,4,6-triamine
213 $N^4$-(2-Fluorobenzyl)-6-[(3S)-3-methylpiperazin-1-yl]pyrimidine-2,4-diamine
214 $N^4$-Ethyl-6-piperazin-1-ylpyrimidine-2,4-diamine
215 6-[(3R)-3-Aminopyrrolidin-1-yl]-$N^4$-(cyclopropylmethyl)pyrimidine-2,4-diamine
216 6-[(3R)-3-Aminopyrrolidin-1-yl]-$N^4$-isobutylpyrimidine-2,4-diamine
217 6-[(3aR*,6aS*)-Hexahydropyrrolo[3,4-c]pyrrol-2(1H)-yl]-$N^4$-isobutylpyrimidine-2,4-diamine
218 6-[(3R)-3-Aminopyrrolidin-1-yl]-$N^4$-(cyclopentylmethyl)pyrimidine-2,4-diamine
219 6-[(3R)-3-Aminopyrrolidin-1-yl]-$N^4$-propylpyrimidine-2,4-diamine
220 N-(2-Aminoethyl)-N'-(cyclopropylmethyl)pyrimidine-4,6-diamine
221 $N^4$-Methyl-6-[(3R)-3-(methylamino)pyrrolidin-1-yl]pyrimidine-2,4-diamine
222 $N^4$-[(1R*,5S*,6s*)-3-Azabicyclo[3.1.0]hex-6-yl]-$N^6$-(2,2-dimethylpropyl)pyrimidine-2,4,6-triamine
223 $N^4$-(tert-Butyl)-6-(4-methylpiperazin-1-yl)pyrimidine-2,4-diamine
224 N-Cyclopropyl-6-(4-methyl-1,4-diazepan-1-yl)pyrimidin-4-amine
225 6-[(3R)-3-Aminopyrrolidin-1-yl]-$N^4$-(3,3-dimethylbutyl)pyrimidine-2,4-diamine
226 N-(2,2-Dimethylpropyl)-6-[3-(isopropylamino)azetidin-1-yl]pyrimidin-4-amine
227 $N^4$-(Cyclopropylmethyl)-6-{3-[(methylamino)methyl]azetidin-1-yl}pyrimidine-2,4-diamine
228 $N^4$-(3-Fluorobenzyl)-6-[(3S)-3-methylpiperazin-1-yl]pyrimidine-2,4-diamine
229 6-(4-Aminopiperidin-1-yl)-$N^4$-isobutylpyrimidine-2,4-diamine
230 $N^4$-Cyclobutyl-6-[(4aR,7aR)-octahydro-6H-pyrrolo[3,4-b]pyridin-6-yl]pyrimidine-2,4-diamine
231 $N^4$-Isopropyl-6-(octahydro-5H-pyrrolo[3,2-c]pyridin-5-yl)pyrimidine-2,4-diamine
232 6-(3-Aminoazetidin-1-yl)-$N^4$-propylpyrimidine-2,4-diamine
233 $N^4$-(3,4-Difluorobenzyl)-6-[3-(methylamino)azetidin-1-yl]pyrimidine-2,4-diamine
234 6-(4-Aminopiperidin-1-yl)-$N^4$-isopropylpyrimidine-2,4-diamine
235 6-[(3R)-3-(Methylamino)pyrrolidin-1-yl]-$N^4$-(3,3,3-trifluoropropyl)pyrimidine-2,4-diamine
236 4-(3,3-Difluoroazetidin-1-yl)-6-[3-(methylamino)azetidin-1-yl]pyrimidin-2-amine
237 $N^4$-(2-Fluorobenzyl)-6-[(3R)-3-methylpiperazin-1-yl]pyrimidine-2,4-diamine
238 6-[(3aR*,6aS*)-Hexahydropyrrolo[3,4-c]pyrrol-2(1H)-yl]-$N^4$-isopropylpyrimidine-2,4-diamine
239 N-(2,2-Dimethylpropyl)-6-(4-methyl-1,4-diazepan-1-yl)pyrimidin-4-amine
240 $N^4$-(4-Fluorobenzyl)-6-[(3S)-3-methyl piperazin-1-yl]pyrimidine-2,4-diamine
241 $N^4$-Isopropyl-6-[(3aR*,6aS*)-5-methylhexahydropyrrolo[3,4-c]pyrrol-2(1H)-yl]pyrimidine-2,4-diamine
242 4-[3-(Methylamino)azetidin-1-yl]-6-[(3S)-3-methylmorpholi$N^4$-yl]pyrimidin-2-amine
243 $N^4$-(Cyclobutylmethyl)-6-[(3R)-3-(methylamino)pyrrolidin-1-yl]pyrimidine-2,4-diamine
244 N-(3,3-Dimethylbutyl)-6-(3-pyrrolidin-1-ylazetidin-1-yl)pyrimidin-4-amine
245 $N^4$-(2,5-Difluorobenzyl)-6-[(3R)-3-(methylamino)pyrrolidin-1-yl]pyrimidine-2,4-diamine
246 6-(3-Amino-3-methylpyrrolidin-1-yl)-$N^4$-(cyclopropylmethyl)pyrimidine-2,4-diamine
247 $N^4$-(4-Fluorobenzyl)-6-[(3R)-3-methylpiperazin-1-yl]pyrimidine-2,4-diamine
248 $N^4$-Methyl-6-[3-methyl-3-(methylamino)azetidin-1-yl]pyrimidine-2,4-diamine
249 $N^4$-(3-Fluorobenzyl)-6-[(3R)-3-(methylamino)pyrrolidin-1-yl]pyrimidine-2,4-diamine
250 $N^4$-(2,2-Dimethylpropyl)-6-[3-(methylamino)piperidin-1-yl]pyrimidine-2,4-diamine
251 $N^4$-Benzyl-6-[(3S)-3-methylpiperazin-1-yl]pyrimidine-2,4-diamine
252 N-Cyclopropyl-6-[(3S)-3-methylpiperazin-1-yl]pyrimidin-4-amine
253 $N^4$-(2-Fluorobenzyl)-6-[(3R)-3-(methylamino)pyrrolidin-1-yl]pyrimidine-2,4-diamine
254 $N^4$-Benzyl-6-[(3R)-3-(methylamino)pyrrolidin-1-yl]pyrimidine-2,4-diamine
255 6-[(3R)-3-Aminopyrrolidin-1-yl]-$N^4$-(2,3-difluorobenzyl)pyrimidine-2,4-diamine
256 $N^4$-Cyclopropyl-6-[(3R)-3-(methylamino)pyrrolidin-1-yl]pyrimidine-2,4-diamine
257 $N^4$-Ethyl-6-[3-methyl-3-(methylamino)azetidin-1-yl]pyrimidine-2,4-diamine
258 6-[(3S)-3-Methylpiperazin-1-yl]-N-propylpyrimidin-4-amine
259 $N^4$-Benzyl-6-[(3R)-3-methylpiperazin-1-yl]pyrimidine-2,4-diamine
260 6-(4-Cyclohexylpiperazin-1-yl)-N-(2,2-dimethylpropyl)pyrimidin-4-amine
261 N-Isopropyl-6-[3-methyl-3-(methylamino)azetidin-1-yl]pyrimidin-4-amine
262 N-Methyl-6-[(3R)-3-(methylamino)pyrrolidin-1-yl]pyrimidin-4-amine
263 4-[3-(Methylamino)azetidin-1-yl]-6-[(3R)-3-methylmorpholi$N^4$-yl]pyrimidin-2-amine
264 6-(3-Amino-3-methylpyrrolidin-1-yl)-$N^4$-propylpyrimidine-2,4-diamine
265 6-(3-Amino-3-methylpyrrolidin-1-yl)-$N^4$-ethylpyrimidine-2,4-diamine
266 6-(4-Aminopiperidin-1-yl)-$N^4$-propylpyrimidine-2,4-diamine
267 $N^4$-(3-Fluorobenzyl)-6-[(3R)-3-methylpiperazin-1-yl]pyrimidine-2,4-diamine
268 4-[3-(Methylamino)azetidin-1-yl]-6-morpholin-4-ylpyrimidin-2-amine
269 6-(4-Aminopiperidin-1-yl)-$N^4$-cyclopropylpyrimidine-2,4-diamine
270 N-(3,3-Dimethylbutyl)-6-(4-ethylpiperazin-1-yl)pyrimidin-4-amine
271 $N^4$-(2,6-Difluorobenzyl)-6-[(3R)-3-(methylamino)pyrrolidin-1-yl]pyrimidine-2,4-diamine 272 N⁴-(2,3-Difluorobenzyl)-6-[(3R)-3-(methylamino)pyrrolidin-1-yl]pyrimidine-2,4-diamine
273 N⁴-(3,5-Difluorobenzyl)-6-[(3R)-3-(methylamino)pyrrolidin-1-yl]pyrimidine-2,4-diamine
274 (5-{[(3S)-3-({6-[(3,3-Dimethylbutyl)amino]pyrimidin-4yl}amino)pyrrolidin--1-yl]methyl}-2-furyl)methanol
275 4-(3,3-Difluoroazetidin-1-yl)-6-[(3R)-3-(methylamino)pyrrolidin-1-yl]pyrimidin-2-amine
276 N,N'-Bis(cyclopropylmethyl)-6-[3-(methylamino)azetidin-1-yl]pyrimidine-2,4-diamine
277 N⁴-(3,4-Difluorobenzyl)-6-[(3R)-3-(methylamino)pyrrolidin-1-yl]pyrimidine-2,4-diamine
278 N⁴-Isobutyl-6-[3-(methylamino)piperidin-1-yl]pyrimidine-2,4-diamine
279 N'-(3,3-Dimethylbutyl)-N-methyl-N-(1-methylpiperidin-4-yl)pyrimidine-4,6-diamine
280 6-(1,4-Diazepan-1-yl)-N-(3,3-dimethylbutyl)pyrimidin-4-amine
281 N-Benzyl-N'-[(3S)-pyrrolidin-3-yl]pyrimidine-4,6-diamine
282 4-[(3R)-3-(Methylamino)pyrrolidin-1-yl]-6-morpholin-4-ylpyrimidin-2-amine
283 6-(4-Aminopiperidin-1-yl)-N⁴-(cyclopropylmethyl)pyrimidine-2,4-diamine
284 6-(4-Aminopiperidin-1-yl)-N⁴-methylpyrimidine-2,4-diamine
285 N-(Cyclopropylmethyl)-6-piperazin-1-ylpyrimidin-4-amine
286 N⁴-lsopropyl-6-[(3R)-3-(methylamino)pyrrolidin-1-yl]pyrimidine-2,4-diamine
287 N⁴-(2,2-Dimethylpropyl)-6-(3-morpholin-4-ylazetidin-1-yl)pyrimidine-2,4-diamine
288 N-(3,3-Dimethylbutyl)-N'-(1-methylpiperidin-3-yl)pyrimidine-4,6-diamine
289 N-[(3S)-1-Benzylpyrrolidin-3-yl]-N'-(3,3-dimethylbutyl)pyrimidine-4,6-diamine
290 N-[(3S)-Pyrrolidin-3-yl]-N'-[(2S)-tetrahydrofuran-2-ylmethyl]pyrimidine-4,6-diamine
291 N-(Cyclopropylmethyl)-5-methyl-6-[(3R)-3-(methylamino)pyrrolidin-1-yl]pyrimidin-4-amine
292 6-(3-Aminopyrrolidin-1-yl)-N-(3,3-dimethylbutyl)pyrimidin-4-amine
293 4-[6-(4-Methylpiperazin-1-yl)pyrimidin-4-yl]morpholine
294 N⁴-(Cyclopropylmethyl)-6-[3-(methylamino)piperidin-1-yl]pyrimidine-2,4-diamine
295 4-[3-(Methylamino)azetidin-1-yl]-6-piperidin-1-ylpyrimidin-2-amine
296 N-(3,3-Dimethylbutyl)-N'-[(3S)-1-methylpyrrolidin-3-yl]pyrimidine-4,6-diamine
297 (1S,5R)-3-{6-[(2,2-Dimethyl propyl)amino]pyrimidin-4-yl}-3-azabicyclo[3.1.0]hexan-1-amine
298 N⁴-(3,3-Dimethylbutyl)-6-[3-methyl-3-(methylamino)azetidin-1-yl]pyrimidine-2,4-diamine
299 N-(3,3-Dimethylbutyl)-6-{4-[(1-methyl-1H-imidazol-2-yl)methyl]piperazin-1-yl}pyrimidin-4-amine
300 (1R*,5S*,6s*)-3-{6-[(3,3-Dimethylbutyl)amino]pyrimidin-4-yl}-N,N-dimethyl-3-azabicyclo[3.1.0]hexan-6-amine
301 N-(3,3-Dimethylbutyl)-6-(4-pyrrolidin-1-ylpiperidin-1-yl)pyrimidin-4-amine
302 6-[3-(Diethylamino)pyrrolidin-1-yl]-N-(2,2-dimethylpropyl)pyrimidin-4-amine
303 6-(4-Azetidin-3-ylpiperazin-1-yl)-N-(2,2-dimethylpropyl)pyrimidin-4-amine
304 (1S*,5R*)-3-{6-[(Cyclopropylmethyl)amino]pyrimidin-4-yl}-3-azabicyclo[3.1.0]hexan-1-amine
305 6-(4-Cyclohexylpiperazin-1-yl)-N-(cyclopropylmethyl)pyrimidin-4-amine
306 N'-(Cyclopropylmethyl)-N-[2-(diethylamino)ethyl]-N-methylpyrimidine-4,6-diamine
307 2-(4-{6-[(3,3-Dimethylbutyl)amino]pyrimidin-4-yl}piperazin-1-yl)ethanol
308 6-(4-Azetidin-3-ylpiperazin-1-yl)-N-(cyclopropylmethyl)pyrimidin-4-amine
309 N⁴-(3,3-Dimethylbutyl)-6-[(1R,5S,6s)-6-(methylamino)-3-azabicyclo[3.1.0]hex-3-yl]pyrimidine-2,4-diamine
310 N⁴-(Cyclopropylmethyl)-6-[(3R)-3-methylpiperazin-1-yl]pyrim idine-2,4-diamine
311 6-[(3R)-3-Aminopyrrolidin-1-yl]-N⁴-(2,5-difluorobenzyl)pyrimidine-2,4-diamine
312 N-(3,3-Dimethylbutyl)-6-(3-morpholin-4-ylazetidin-1-yl)pyrimidin-4-amine
313 6-[(3R)-3-Methylpiperazin-1-yl]-N-propylpyrimidin-4-amine
314 N-Cyclopropyl-6-(1,4-diazepan-1-yl)pyrimidin-4-amine
315 N-(2-Phenylethyl)-N'-[(3S)-pyrrolidin-3-yl]pyrimidine-4,6-diamine
316 N⁴-(3,5-Difluorobenzyl)-6-[3-(methylamino)azetidin-1-yl]pyrimidine-2,4-diamine
317 N⁴-(2,6-Difluorobenzyl)-6-[3-(methylamino)azetidin-1-yl]pyrimidine-2,4-diamine
318 N⁴-(2,2-Dimethylpropyl)-6-[(4aR,7aR)-octahydro-6H-pyrrolo[3,4-b]pyridin-6-yl]pyrimidine-2,4diamine
319 N-[(3S)-Pyrrolidin-3-yl]-N'-[(2R)-tetrahydrofuran-2-ylmethyl]pyrimidine-4,6-diamine
320 6-(3-Amino-3-methylpyrrolidin-1-yl)-N⁴-methylpyrimidine-2,4-diamine
321 N⁴-Methyl-6-[3-(methylamino)piperidin-1-yl]pyrimidine-2,4-diamine
322 N⁴-(Cyclopropylmethyl)-6-(3-morpholin-4-ylazetidin-1-yl)pyrimidine-2,4-diamine
323 6-[3-(Methylamino)piperidin-1-yl]-N⁴-propylpyrimidine-2,4-diamine
324 N⁴-Ethyl-6-[3-(methylamino)piperidin-1-yl]pyrimidine-2,4-diamine
325 N⁴-(2,4-Difluorobenzyl)-6-[(3R)-3-(methylamino)pyrrolidin-1-yl]pyrimidine-2,4-diamine
326 N-(2,2-Dimethylpropyl)-5-methyl-6-[(3R)-3-(methylamino)pyrrolidin-1-yl]pyrimidin-4-amine
327 6-[(3-S)-1,3'-Bipyrrolidin-1'-yl]-N⁴-(2,2-dimethylpropyl)pyrimidine-2,4-diamine
328 N-(3,3-Dimethylbutyl)-6-[(4aR*,7aR*)-octahydro-6H-pyrrolo[3,4-b]pyridin-6-yl]pyrimidin-4-amine
329 N-(3-Methylbutyl)-N'-[(3R)-pyrrolidin-3-yl]pyrimidine-4,6-diamine
330 N⁴-(3,3-Dimethylbutyl)-N²,N²-dimethyl-6-(4-methylpiperazin-1-yl)pyrimidine-2,4-diamine
331 N-isoPropyl-5-methyl-6-(4-methylpiperazin-1-yl)pyrimidin-4-amine
332 6-[(3'S)-1,3'-Bipyrrolidin-1'-yl]-N⁴-(3,3-dimethylbutyl)pyrimidine-2,4-diamine
333 6-[(1R*,5S*,6s*)-6-Amino-3-azabicyclo[3.1.0]hex-3-yl]-N⁴-(3,3-dimethylbutyl)pyrimidine-2,4-diamine
334 N-(Cyclopropylmethyl)-N-methyl-6-(4-methylpiperazin-1-yl)pyrimidin-4-amine
335 N-(2-Methoxyethyl)-N'-[(3R)-pyrrolidin-3-yl]pyrimidine-4,6-diamine
336 N-Methyl-1-(6-pyrrolidin-1-ylpyrimidin-4-yl)azetidin-3-amine
337 N-Benzyl-N'-[(3R)-pyrrolidin-3-yl]pyrimidine-4,6-diamine 338  N⁴-[(3S)-1-Benzylpyrrolidin-3-yl]-N6-(3,3-dimethylbutyl)pyrimidine-2,4,6-triamine
339  N⁴-(3,3-Dimethylbutyl)-N²-methyl-6-(4-methylpiperazin-1-yl)pyrimidine-2,4-diamine
340  6-(4-Aminopiperidin-1-yl)-N-(3,3-dimethylbutyl)pyrimidin-4-amine
341  N-[(3R)-Pyrrolidin-3-yl]-N'-[(2S)-tetrahydrofuran-2-ylmethyl]pyrimidine-4,6-diamine
342  6-[(3'S)-1,3'-Bipyrrolidin-1'-yl]-N-(3,3-dimethylbutyl)pyrimidin-4-amine
343  N-(3,3-Dimethylbutyl)-N'-(1-methylpiperidin-4-yl)pyrimidine-4,6-diamine
344  N-(2-Methoxyethyl)-N'-[(3S)-pyrrolidin-3-yl]pyrimidine-4,6-diamine
345  N-[(3R)-Pyrrolidin-3-yl]-N'-[(2R)-tetrahydrofuran-2-ylmethyl]pyrimidine-4,6-diamine
346  N-(2-Phenylethyl)-N'-[(3R)-pyrrolidin-3-yl]pyrimidine4,6-diamine
347  N-(Cyclopropylmethyl)-N'-[2-(methylamino)ethyl]pyrimidine-4,6-diamine
348  N-[(3R)-1-Benzylpyrrolidin-3-yl]-N'-(3,3-dimethylbutyl)pyrimidine-4,6-diamine
349  (5-{[(3R)-3-({6-[(3,3-Dimethylbutyl)amino]pyrimidin-4-yl}amino)pyrrolidin-1-yl]methyl}-2-furyl)methanol
350  N-(2,3-Dihydro-1H-inden-2-yl)-N'-[(3R)-pyrrolidin-3-yl]pyrimidine-4,6-diamine
351  6-(3,4-Dihydroisoquinolin-2(1H)-yl)-N-[(3R)-pyrrolidin-3-yl]pyrimidin-4-amine
352  N⁴-(3-Fluorobenzyl)-6-[3-(methylamino)azetidin-1-yl]pyrimidine-2,4-diamine
353  N-(2,2-Dimethylpropyl)-6-[(1R,5S)-1,2,4,5-tetrahydro-3H-1,5-epimino-3-benzazepin-3-yl]pyrimidin-4-amine
354  N⁴CyClobutyl-6-[(4aS,7aS)-octahydro-6H-pyrrolo[3,4-b]pyridin-6-yl]pyrimidine-2,4-diamine
355  N⁴-(Cyclopropylmethyl)-6-[(4aS,7aS)-octahydro-6H-pyrrolo[3,4-b]pyridin-6-yl]pyrimidine-2,4-diamine
356  N⁴-(tert-Butyl)-6-(4-methylpiperazin-1-yl)pyrimidine-2,4-diamine
357  N⁴-(tert-Butyl)-6-[(4aS,7aS)-octahydro-6H-pyrrolo[3,4-b]pyridin-6-yl]pyrimidine-2,4-diamine
358  N⁴-(2,2-Dimethylpropyl)-6-[(1R*,5S*,6s*)-6-(methylamino)-3-azabicyclo[3.1.0]hex-3-yl]pyrimidine-2,4-diamine
359  N⁴-Cyclopropyl-6-[(4aR,7aR)-octahydro-6H-pyrrolo[3,4-b]pyridin-6-yl]pyrimidine-2,4-diamine
360  2-({2-Amino-6-[3-(methylamino)azetidin-1-yl]pyrimidin-4-yl}amino)ethanol
361  6-(1,4-Diazepan-1-yl)-N⁴-isopropylpyrimidine-2,4-diamine
362  6-[(1R,4R)-2,5-Diazabicyclo[2.2.1]hept-2-yl]-N⁴-(2,2-dimethylpropyl)pyrimidine-2,4-diamine
363  6-[(3R)-3-Aminopyrrolidin-1-yl]-N⁴-(2,2-dimethylpropyl)pyrimidine-2,4-diamine
364  4-[(3R)-3-(Methylamino)pyrrolidin-1-yl]-6-(2-methyl-1H-imidazol-1-yl)pyrimidin-2-amine
365  6-[3-(Methylamino)azetidin-1-yl]-N⁴-[(1R)-1-methylpropyl]pyrimidine-2,4-diamine
366  6-[(3R)-3-Aminopyrrolidin-1-yl]-N⁴-ethylpyrimidine-2,4-diamine
367  6-[(3R)-3-Aminopyrrolidin-1-yl]-N⁴-(3,3,3-trifluoropropyl)pyrimidine-2,4-diamine
368  6-[(3R)-3-(Methylamino)pyrrolidin-1-yl]-N-[(i S)-i-methylpropyl]pyrimidin-4-amine
369  6-[3-(Methylamino)azetidin-1-yl]-N-[(1R)-1-methylpropyl]pyrimidin-4-amine
370  6-[(3R)-3-(Methylamino)pyrrolidin-1-yl]-N-propylpyrimidin-4-amine
371  6-(3-Aminoazetidin-1-yl)-N-(2,2-dimethylpropyl)pyrimidin-4-amine
372  N⁴-(Cyclopropylmethyl)-5-methyl-6-[(3R)-3-(methylamino)pyrrolidin-1-yl]pyrimidine-2,4-diamine
373  N⁴-(Cyclopropylmethyl)-6-(2,8-diazaspiro[4.5]dec-2-yl)pyrimidine-2,4-diamine
374  6-(2,8-Diazaspiro[4.5]dec-2-yl)-N⁴-isobutylpyrimidine-2,4-diamine
375  N⁴-(Cyclopropylmethyl)-6-(2,7-diazaspiro[4.4]non-2-yl)pyrimidine-2,4-diamine
376  6-(2,7-Diazaspiro[4.4]non-2-yl)-N⁴-isobutylpyrimidine-2,4-diamine Biology $H_4$ Binding Cell pellets from CHO cells expressing the histamine $H_4$ receptor were homogenised in ice-cold 50 mM Tris-HCl/0.5 mM $CaCl_2$ buffer containing a protease inhibitor cocktail (Roche®, United Kingdom) using a ground glass homogeniser. Homogenates were centrifuged at 48000 g for 30 min at 4° C. The membrane pellet was resuspended in fresh buffer and the centrifugation step was repeated as described above. The membrane pellet was resuspended in 50 mM Tris-HCl in the same volume as the original cell pellet. Aliquots of membrane preparations were stored at −80° C. and were used for [³H]-Histamine binding experiments.

Method 1

Cell membranes (20-35 µg/well) were incubated for 90 minutes shaking at room temperature with 3 nM [2,5-³H] Histamine dihydrochloride (30-60 Ci/mmol) in 50 mM Tris-HCl (pH 7.4), with or without competing $H_4$ ligands. The reaction was terminated by rapid filtration through 0.5% polyethylenimine-soaked Unifilter GF/B plates (Packard) followed by three washes with 1 ml ice-cold 50 mM Tris-HCl. Filters were dried for 45 min at 45° C. and bound radiolabel was determined using scintillation counting techniques. Non-specific binding was defined with 10 µM JNJ7777120. For competition binding studies, Ki values were calculated form the $IC_{50}$ value based on an experimentally determined ligand $K_d$ of 5.2 nM and a ligand concentration of 5 nM according to the Cheng-Prussoff equation where; $K_i=(IC_{50})/(1+([L]/K_d))$.

Method 2

Cell membranes (15 µg/well) were pre-incubated for 120 min shaking at 4° C. with Ysi WGA beads (250 µg/well) in 50 mM Tris-HCl (pH 7.4) followed by centrifugation at 1500 rpm for 5 minutes and resuspension in 50 mM Tris-HCl (pH 7.4). The membrane/bead mixture (15 µg membrane/250 µg beads well) was incubated for 90 minutes shaking at room temperature with 6.5 nM [2,5-³H] Histamine dihydrochloride (30-60 Ci/mmol) in 50 mM Tris-HCl (pH 7.4), with or without competing $H_4$ ligands. Non-specific binding was defined with 10 µM JNJ7777120. Bound radiolabel was determined using scintillation counting techniques after 90 minutes. For competition binding studies, Ki values were calculated from the $IC_{50}$ value based on an experimentally determined ligand $K_d$ of 5.2 nM and a ligand concentration of 5 nM according to the Cheng-Prussoff equation where; $K_i=(IC_{50})/(1+([L]/K_d))$.

The compounds of the Examples have been tested in the $H_4$ binding assay described above using either method 1 or method 2. Preferred examples have a $K_i$ value of less than 1 µM in the $H_4$ binding assay. Most preferred examples have a $K_i$ value of less than 500 nM in the $H_4$ binding assay (method 2). The specific $K_i$ values for the Example compounds that have been tested in method 1 and method 2 are given in the table below:

| Example | Method 2 (Ki (nM)) | Method 1 (Ki (nM)) | Example | Method 2 (Ki (nM)) | Method 1 (Ki (nM)) |
|---|---|---|---|---|---|
| 1 | 335 | 82.3 | 78 | 3.66 | NT |
| 2 | NT | 485 | 79 | 11.2 | NT |
| 3 | NT | 220 | 80 | 103 | NT |
| 4 | NT | 374 | 81 | 12.1 | NT |
| 5 | NT | 263 | 82 | 9.68 | NT |
| 6 | NT | 502 | 83 | 62.3 | NT |
| 7 | NT | 939 | 84 | 21.7 | NT |
| 8 | NT | 593 | 85 | 156 | NT |
| 9 | 19.3 | 2.7 | 86 | 142 | NT |
| 10 | 4.11 | 2.85 | 87 | 17.4 | NT |
| 11 | 31.6 | 10.6 | 88 | 35.8 | NT |
| 12 | 52.4 | NT | 89 | 1.93 | NT |
| 13 | 51.8 | NT | 90 | 6.42 | NT |
| 14 | 23.3 | 13.6 | 91 | 386 | NT |
| 15 | 19.2 | NT | 92 | 1350 | NT |
| 16 | 1740 | NT | 93 | 256 | NT |
| 17 | 483 | NT | 94 | 61.1 | NT |
| 18 | 387 | NT | 95 | 9.11 | NT |
| 19 | 132 | NT | 96 | 3.77 | NT |
| 20 | 58.1 | 30.5 | 97 | 43.7 | NT |
| 21 | 722 | NT | 98 | 56.2 | NT |
| 22 | 59.3 | 58.9 | 99 | 38.1 | 23.6 |
| 23 | 824 | NT | 100 | NT | 40.2 |
| 24 | 30.8 | NT | 101 | NT | 463 |
| 25 | 154 | NT | 102 | NT | 57.3 |
| 26 | 30 | NT | 103 | NT | 87.9 |
| 27 | 22.4 | NT | 104 | NT | 118 |
| 28 | 21.3 | NT | 105 | NT | 68.8 |
| 29 | 82.9 | NT | 106 | NT | 66.1 |
| 30 | 19.3 | 3.06 | 107 | NT | 271 |
| 31 | 21.1 | NT | 108 | 8.42 | NT |
| 32 | 20.9 | NT | 109 | 42.7 | NT |
| 33 | 84.1 | NT | 110 | 829 | NT |
| 34 | 452 | NT | 111 | 1800 | 201 |
| 35 | 662 | NT | 112 | 635 | NT |
| 36 | 1620 | NT | 113 | 1480 | NT |
| 37 | 181 | NT | 114 | 1030 | NT |
| 38 | 128 | NT | 115 | 494 | NT |
| 39 | 88.9 | NT | 116 | 426 | NT |
| 41 | 202 | NT | 117 | 1620 | NT |
| 40 | 192 | NT | 118 | 1090 | NT |
| 42 | 433 | NT | 119 | 7.8 | 3.44 |
| 43 | 236 | NT | 120 | 11.2 | 4.89 |
| 44 | 20.5 | NT | 121 | 6.64 | 2.18 |
| 45 | 420 | NT | 122 | 8.65 | 3.65 |
| 46 | 40.1 | NT | 123 | 103 | NT |
| 47 | 256 | NT | 124 | 537 | NT |
| 48 | 49.7 | NT | 125 | 223 | NT |
| 49 | 29.9 | 10.7 | 126 | 611 | NT |
| 50 | 279 | NT | 127 | 65.8 | NT |
| 51 | 161 | NT | 128 | NT | 0.805 |
| 52 | 99.7 | NT | 129 | NT | 3.78 |
| 53 | 1940 | NT | 130 | NT | 9.69 |
| 54 | 414 | NT | 131 | NT | 17.8 |
| 55 | 28.9 | NT | 132 | NT | 0.791 |
| 56 | 1590 | NT | 133 | NT | 0.653 |
| 57 | 20.3 | NT | 134 | NT | 4.15 |
| 58 | 301 | NT | 135 | NT | 1.13 |
| 59 | 59.2 | 37.7 | 136 | NT | 7.21 |
| 60 | 28.8 | 3.57 | 137 | NT | 8.25 |
| 61 | 1.33 | 1.66 | 138 | NT | 5.8 |
| 62 | 14.1 | 8.94 | 139 | NT | 12.1 |
| 63 | 12.2 | 1.95 | 140 | NT | 12.1 |
| 64 | 4.43 | 4.63 | 141 | 4.97 | |
| 65 | 19.8 | 17.5 | 142 | NT | 3.04 |
| 66 | 61.1 | NT | 143 | NT | 72.4 |
| 67 | 1.6 | 0.278 | 144 | NT | 16.8 |
| 68 | 6.26 | 0.979 | 145 | NT | 14.3 |
| 69 | 9.38 | NT | 146 | NT | 13.7 |
| 70 | 2.14 | 3.79 | 147 | NT | 17.3 |
| 71 | 14 | 1.29 | 148 | NT | 4.89 |
| 72 | 11.9 | NT | 149 | NT | 5.2 |
| 73 | NT | 0.88 | 150 | NT | 11.8 |
| 74 | 16.8 | 0.58 | 151 | NT | 12.4 |
| 75 | NT | 1.07 | 152 | NT | 16.9 |
| 76 | 125 | NT | 153 | NT | 11.5 |
| 77 | 255 | NT | 154 | NT | 1.71 |

| Example | Method 2 (Ki (nM)) | Method 1 (Ki (nM)) |
| --- | --- | --- |
| 155 | NT | 1.78 |
| 156 | NT | 2.44 |
| 157 | NT | 2.49 |
| 158 | NT | 2.59 |
| 159 | NT | 2.62 |
| 160 | NT | 2.65 |
| 161 | NT | 2.75 |
| 162 | NT | 2.91 |
| 163 | NT | 3.78 |
| 164 | 24.5 | 3.82 |
| 165 | NT | 3.83 |
| 166 | NT | 3.99 |
| 167 | NT | 6.3 |
| 168 | NT | 6.5 |
| 169 | NT | 6.77 |
| 170 | NT | 8.55 |
| 171 | NT | 9.21 |
| 172 | NT | 9.3 |
| 173 | NT | 10.1 |
| 174 | NT | 10.6 |
| 175 | NT | 12.3 |
| 176 | NT | 15.1 |
| 177 | NT | 16 |
| 178 | NT | 16.1 |
| 179 | NT | 16.5 |
| 180 | NT | 17.4 |
| 181 | NT | 17.6 |
| 182 | NT | 19.8 |
| 183 | NT | 20 |
| 184 | NT | 20.4 |
| 185 | NT | 20.5 |
| 186 | NT | 22.2 |
| 187 | NT | 22.4 |
| 188 | NT | 25.5 |
| 189 | NT | 25.8 |
| 190 | NT | 27.7 |
| 191 | NT | 28.2 |
| 192 | NT | 28.7 |
| 193 | NT | 31 |
| 194 | NT | 32.4 |
| 195 | NT | 32.6 |
| 196 | NT | 33.1 |
| 197 | NT | 33.2 |
| 198 | NT | 33.6 |
| 199 | NT | 33.9 |
| 200 | NT | 34 |
| 201 | NT | 35 |
| 202 | NT | 36.5 |
| 203 | NT | 37.9 |
| 204 | NT | 39 |
| 205 | NT | 39.3 |
| 206 | NT | 39.9 |
| 207 | NT | 43.3 |
| 208 | NT | 45.1 |
| 209 | NT | 46.4 |
| 210 | NT | 48.9 |
| 211 | NT | 49.3 |
| 212 | NT | 50 |
| 213 | NT | 52.9 |
| 214 | NT | 54.4 |
| 215 | NT | 57.3 |
| 216 | NT | 70.6 |
| 217 | NT | 80.6 |
| 218 | NT | 80.7 |
| 219 | NT | 82.3 |
| 220 | NT | 88 |
| 221 | NT | 90.3 |
| 222 | NT | 95.2 |
| 223 | NT | 13% at 10 µM |
| 224 | NT | 101 |
| 225 | NT | 102 |
| 226 | NT | 113 |
| 227 | NT | 115 |
| 228 | NT | 117 |
| 229 | NT | 127 |
| 230 | NT | 127 |
| 231 | NT | 131 |
| 232 | NT | 13.88 |
| 233 | NT | 30.4 |
| 234 | NT | 177 |
| 235 | NT | 198 |
| 236 | NT | 205 |
| 237 | NT | 211 |
| 238 | NT | 222 |
| 239 | NT | 235 |
| 240 | NT | 238 |
| 241 | NT | 45% at 1 µM |
| 242 | NT | 258 |
| 243 | NT | 266 |
| 244 | NT | 297 |
| 245 | NT | 298 |
| 246 | NT | 301 |
| 247 | NT | 312 |
| 248 | NT | 329 |
| 249 | NT | 343 |
| 250 | NT | 353 |
| 251 | NT | 355 |
| 252 | NT | 370 |
| 253 | NT | 380 |
| 254 | NT | 380 |
| 255 | NT | 452 |
| 256 | NT | 501 |
| 257 | NT | 100% at 10 µM |
| 258 | NT | 509 |
| 259 | NT | 577 |
| 260 | NT | 100% at 10 µM |
| 261 | NT | 617 |
| 262 | NT | 623 |
| 263 | NT | 626 |
| 264 | NT | 704 |
| 265 | NT | 705 |
| 266 | NT | 708 |
| 267 | NT | 715 |
| 268 | NT | 16% at 10 µM |
| 269 | NT | 839 |
| 270 | >16200 | 839 |
| 271 | NT | 870 |
| 272 | NT | 901 |
| 273 | NT | 950 |
| 274 | NT | 1070 |
| 275 | NT | 1160 |
| 276 | NT | 14% at 3.16 µM |
| 277 | NT | 1230 |
| 278 | NT | 1260 |
| 279 | >9130 | 1370 |
| 280 | NT | 1430 |
| 281 | NT | 1550 |
| 282 | NT | 1660 |
| 283 | NT | 1700 |
| 284 | NT | 1720 |
| 285 | NT | 1800 |
| 286 | NT | 1940 |
| 287 | NT | 2000 |
| 288 | NT | 2400 |
| 289 | NT | 44% at 10 µM |
| 290 | NT | 24% at 10 µM |
| 291 | NT | No activity at top dose (6.3 µM) |
| 292 | NT | 2590 |
| 293 | NT | 3040 |
| 294 | NT | 91% at 20 µM |
| 295 | NT | 3180 |
| 296 | NT | 3300 |
| 297 | NT | 30% at 10 µM |
| 298 | NT | No activity at top dose (10 µM) |
| 299 | NT | No activity at top dose (10 µM) |
| 300 | NT | 35% at 10 µM |
| 301 | NT | No activity at top dose (10 µM) |
| 302 | NT | 20% at 10 µM |
| 303 | NT | 38% at 10 µM |
| 304 | NT | 19% at 10 µM |

-continued

| Example | Method 2 (Ki (nM)) | Method 1 (Ki (nM)) |
|---|---|---|
| 305 | NT | No activity at top dose (10 μM) |
| 306 | NT | 18% at 10 μM |
| 307 | NT | 24% at 10 μM |
| 308 | NT | No activity at top dose (10 μM) |
| 309 | NT | 26% at 10 μM |
| 310 | NT | No activity at top dose (10 μM) |
| 311 | NT | 80% at 20 μM |
| 312 | NT | 21% at 20 μM |
| 313 | NT | 70% at 20 μM |
| 314 | NT | No activity at top dose (10 μM) |
| 315 | NT | 5190 |
| 316 | NT | No activity at top dose (10 μM) |
| 317 | NT | No activity at top dose (10 μM) |
| 318 | NT | No activity at top dose (10 μM) |
| 319 | NT | 6010 |
| 320 | NT | 46% at 6.3 μM |
| 321 | NT | 15% at 20 μM |
| 322 | NT | 57% at 20 μM |
| 323 | NT | 85% at 20 μM |
| 324 | NT | 55% at 20 μM |
| 325 | NT | 43% at 20 μM |
| 326 | NT | 48% at 20 μM |
| 327 | 376 | NT |
| 328 | 554 | NT |
| 329 | 1420 | NT |
| 330 | 1440 | NT |
| 331 | 2670 | NT |
| 332 | 2690 | NT |
| 333 | 3120 | NT |
| 334 | 5070 | NT |
| 335 | 5350 | NT |
| 336 | 6330 | NT |
| 337 | 7220 | NT |
| 338 | 7930 | NT |
| 339 | 9070 | NT |
| 340 | 50% at 40 μM | NT |
| 341 | 16300 | NT |
| 342 | 13% at 40 μM | NT |
| 343 | 53% at 40 μM | NT |
| 344 | 40% at 40 μM | NT |
| 345 | 49% at 40 μM | NT |
| 346 | 38400 | NT |
| 347 | NT | NT |
| 348 | NT | NT |
| 349 | NT | NT |
| 350 | NT | NT |
| 351 | NT | NT |
| 352 | NT | NT |
| 353 | NT | NT |
| 354 | NT | NT |
| 355 | NT | NT |
| 356 | NT | NT |
| 357 | NT | NT |
| 358 | NT | NT |
| 359 | NT | NT |
| 360 | NT | NT |
| 361 | NT | NT |
| 362 | NT | NT |
| 363 | NT | NT |
| 364 | NT | NT |
| 365 | NT | NT |
| 366 | NT | NT |
| 367 | NT | NT |
| 368 | NT | NT |
| 369 | NT | NT |
| 370 | NT | NT |
| 371 | NT | NT |
| 372 | NT | NT |
| 373 | NT | NT |
| 374 | NT | NT |
| 375 | NT | NT |
| 376 | NT | NT |

NT: not tested

What is claimed is:

1. A compound of Formula (I):

or a pharmaceutically or veterinarily acceptable salt thereof, wherein:

$R^1$ is $C_{3-7}$cycloalkyl-$C_{0-6}$alkyl- optionally substituted with methyl $R^3$ and $R^2$ together with the nitrogen atom to which they are bound form a 5 membered non-aromatic heterocyclic group, said group being optionally substituted by one or more substituents independently selected from $C_{1-6}$alkyl, $NR^6R^7$, $(CH_2)_aC_{3-7}$cycloalkyl, alkoxyalkyl containing 2 to 8 carbon atoms, $(CH_2)_b$het$^1$, $(CH_2)_cCF_3$, $(CH_2)_yOCF_3$, $(CH_2)_d$aryl and $C_{1-6}$hydroxyalkyl, provided that the ring system is substituted by a group which contains at least one nitrogen atom;

$R^4$ is H;

$R^5$ is $NR^{11}R^{12}$;

$R^6$ and $R^7$ are each independently selected from H, $C_{1-6}$alkyl and $(CH_2)_jC_{3-7}$cycloalkyl; or $R^6$ and $R^7$, together with the nitrogen atom to which they are bound, form a 4, 5 or 6 membered heterocyclic group;

$R^8$ is H or $C_{1-3}$alkyl;

$R^{11}$ and $R^{12}$ are each independently selected from H, $C_{1-6}$alkyl and $(CH_2)_lC_{3-7}$cycloalkyl;

a, b, c, d, j, and l are each independently selected from 0, 1, 2 and 3;

z is selected from 1, 2 and 3;

aryl is phenyl, naphthyl, anthracyl or phenanthryl, each optionally substituted by one or more groups independently selected from $C_{1-8}$alkyl, $C_{1-8}$alkoxy, OH, halo, $CF_3$, $CHF_2$, $OCF_3$, $OCHF_2$, $SCF_3$, hydroxy-$C_{1-6}$alkyl, $C_{1-4}$alkoxy-$C_{1-6}$alkyl, $C_{1-4}$alkyl-S—$C_{1-4}$alkyl, aryl$^1$, het$^1$, Oaryl$^1$, Ohet$^1$, Saryl$^1$, Shet$^1$, $CF_2CF_3$, $CH_2CF_3$, $CF_2CH_3$, $C(O)NR^{13}R^{14}$, $C_{3-8}$cycloalkyl, $C_{3-7}$cycloalkyl-$C_{1-4}$alkyl, $C_{3-7}$cycloalkyl-$C_{1-4}$alkoxy, $C_{3-7}$cycloalkyl-O—$C_{1-4}$alkyl, $C_{3-7}$cycloalkyl-$C_{1-4}$alkoxy-$C_{1-4}$alkyl, $OC_{3-7}$cycloalkyl and $SC_{3-7}$cycloalkyl, wherein the aryl$^1$ and het$^1$ groups are optionally substituted by at least one group selected from $C_{1-6}$alkyl, $C_{3-7}$cycloalkyl, $C_{1-6}$alkoxy, $OC_{3-7}$cycloalkyl, halo, CN, OH, $CF_3$, $CHF_2$, $OCF_3$, $OCHF_2$, hydroxy$C_{1-6}$alkyl, $C_{1-4}$alkoxy-$C_{1-4}$alkyl, $SC_{1-6}$alkyl and $SCF_3$;

aryl$^1$ is phenyl, naphthyl, anthracyl or phenanthryl; and het$^1$ is an aromatic or non-aromatic 4-, 5- or 6- membered heterocycle which contains at least one N, O or S heteroatom, optionally fused to a 4-, 5- or 6- membered carbocyclic group or a second 4-, 5- or 6- membered heterocycle which contains at least one N, O or S heteroatom.

2. A compound according to claim 1, or a pharmaceutically or veterinarily acceptable salt thereof, wherein $R^8$ is hydrogen.

3. A compound according to claim 1, or a pharmaceutically and/or veterinarily acceptable salt thereof, wherein $R^1$ is $C_{3-5}$cycloalkyl-$C_{0-1}$alkyl- optionally substituted with methyl.

4. A compound according to claims 3, or a pharmaceutically or veterinarily acceptable salt thereof, wherein $R^1$ is cyclopropyl, cyclopropyl-methyl or methyl-cyclopropyl.

5. A compound according to claim 1, or a pharmaceutically or veterinarily acceptable salt thereof, wherein $R^2$ and $R^3$, together with the nitrogen atom to which they are bound, form:

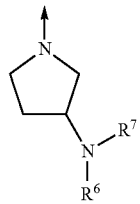

wherein the ring system as a whole may be substituted by one or more $C_{1-6}$alkyl or $(CH_2)_aC_{3-7}$cycloalkyl groups.

6. A compound according to claim 5, or a pharmaceutically or veterinarily acceptable salt thereof, wherein $R^6$ and $R^7$ are independently selected from H or $CH_3$.

7. A compound according to claim 1, or a pharmaceutically or veterinarily acceptable salt thereof, said compound being selected from $N^4$-(Cyclopropylmethyl)-6-[(3R)-3-(methylamino)pyrrolidin-1-yl]pyrimidine-2,4-diamine, $N^4$-(Cyclopropylmethyl)-6-[(3R)-3-(methylamino)pyrrolidin-1-yl]pyrimidine-2,4-diamine tartrate, N-(Cyclopropylmethyl)-6-[(3R)-3-(methylamino)pyrrolidin-1-yl]pyrimidin-4-amine, $N^4$-Bicyclo[1.1.1]pent-1-yl-6-[(3R)-3-(methylamino)pyrrolidin-1-yl]pyrimidine-2,4-diamine, 6-[(3R)-3-(Methylamino)pyrrolidin-1yl]-$N^4$-(1-methylcyclopropyl)pyrmidine-2,4-diamine, $N^4$-(Cyclopropylmethyl)-6-[(3R)-3-(methylamino)pyrrolidin-1-yl]pyrimidine-2,4-diamine, and $N^4$-(Cyclopentylmethyl)-6-[(3R)-3-(methylamino)pyrrolidin-1-yl]pyrimidine-2,4-diamine.

8. A pharmaceutical composition comprising a compound according to claim 1, or a pharmaceutically or veterinarily acceptable salt thereof, together with a pharmaceutically acceptable excipient.

9. $N^4$-(Cyclopropylmethyl)-6-[(3R)-3-(methylamino)pyrrolidin-1-yl]pyrimidine-2,4-diamine, or a pharmaceutically or veterinarily acceptable salt thereof.

10. $N^4$-(Cyclopropylmethyl)-6-[(3R)-3-(methylamino)pyrrolidin-1-yl]pyrimidine-2,4-diamine, tartrate.

11. A method for treating adult respiratory distress syndrome, acute respiratory distress syndrome, bronchitis, chronic bronchitis, chronic obstructive pulmonary disease, cystic fibrosis, asthma, emphysema, rhinitis or chronic sinusitis in a mammal, said method comprising administering to said mammal an effective amount of a compound according to claim 1 or a pharmaceutically or veterinarily acceptable salt thereof.

* * * * *